United States Patent
Metz et al.

(10) Patent No.: US 9,315,724 B2
(45) Date of Patent: Apr. 19, 2016

(54) METAL COMPLEXES COMPRISING AZABENZIMIDAZOLE CARBENE LIGANDS AND THE USE THEREOF IN OLEDS

(75) Inventors: Stefan Metz, Mannheim (DE); Evelyn Fuchs, Mannheim (DE); Korinna Dormann, Bad Dürkheim (DE); Oliver Molt, Weinheim (DE); Christian Lennartz, Schifferstadt (DE); Gerhard Wagenblast, Wachenheim (DE); Thomas Geβner, Heidelberg (DE); Christian Schildknecht, San Diego, CA (US); Soichi Watanabe, Mannheim (DE)

(73) Assignee: BASF SE, Ludwigshafen (DE)

( * ) Notice: Subject to any disclaimer, the term of this patent is extended or adjusted under 35 U.S.C. 154(b) by 835 days.

(21) Appl. No.: 13/494,563

(22) Filed: Jun. 12, 2012

(65) Prior Publication Data

US 2012/0319050 A1     Dec. 20, 2012

Related U.S. Application Data

(60) Provisional application No. 61/496,646, filed on Jun. 14, 2011.

(51) Int. Cl.
| | | |
|---|---|---|
| C07F 15/00 | (2006.01) | |
| C09K 11/06 | (2006.01) | |
| H01L 51/00 | (2006.01) | |
| H01L 51/50 | (2006.01) | |

(52) U.S. Cl.
CPC ............. *C09K 11/06* (2013.01); *C07F 15/0033* (2013.01); *H01L 51/0085* (2013.01); *C09K 2211/1007* (2013.01); *C09K 2211/1029* (2013.01); *C09K 2211/1044* (2013.01); *C09K 2211/1059* (2013.01); *C09K 2211/1074* (2013.01); *C09K 2211/185* (2013.01); *H01L 51/5016* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 7,154,114 B2 | 12/2006 | Brooks et al. | |
| 7,279,704 B2 | 10/2007 | Walters et al. | |
| 7,393,599 B2 | 7/2008 | Thompson et al. | |
| 7,445,855 B2 | 11/2008 | Mackenzie et al. | |
| 7,491,823 B2 | 2/2009 | Thompson et al. | |
| 7,534,505 B2 | 5/2009 | Lin et al. | |
| 7,582,365 B2 | 9/2009 | Walters et al. | |
| 7,598,388 B2 | 10/2009 | Tsai et al. | |
| 7,601,436 B2 | 10/2009 | Djurovich et al. | |
| 7,655,322 B2 | 2/2010 | Forrest et al. | |
| 7,655,323 B2 | 2/2010 | Walters et al. | |
| 7,795,430 B2 | 9/2010 | Walters et al. | |
| 7,956,192 B2 | 6/2011 | Tsai et al. | |
| 8,007,926 B2 | 8/2011 | Thompson et al. | |
| 8,114,533 B2 | 2/2012 | Djurovich et al. | |
| 2005/0258433 A1 | 11/2005 | Djurovich et al. | |
| 2005/0258742 A1 | 11/2005 | Tsai et al. | |
| 2005/0260441 A1 | 11/2005 | Thompson et al. | |
| 2005/0260444 A1 | 11/2005 | Forrest et al. | |
| 2005/0260445 A1 | 11/2005 | Walters et al. | |
| 2005/0260446 A1 | 11/2005 | Mackenzie et al. | |
| 2005/0260447 A1 | 11/2005 | Brooks et al. | |
| 2005/0260448 A1 | 11/2005 | Lin et al. | |
| 2005/0260449 A1 | 11/2005 | Walters et al. | |
| 2006/0024522 A1 | 2/2006 | Thompson et al. | |
| 2006/0154106 A1 | 7/2006 | Walters et al. | |
| 2006/0258043 A1 | 11/2006 | Bold et al. | |
| 2007/0224446 A1 | 9/2007 | Nakano et al. | |
| 2008/0018221 A1 | 1/2008 | Egen et al. | |
| 2009/0017331 A1 | 1/2009 | Iwakuma et al. | |
| 2009/0134784 A1 | 5/2009 | Lin et al. | |
| 2009/0140640 A1 | 6/2009 | Thompson et al. | |
| 2009/0153034 A1 | 6/2009 | Lin et al. | |
| 2009/0284138 A1 | 11/2009 | Yasukawa et al. | |
| 2009/0302754 A1 | 12/2009 | Tsai et al. | |
| 2009/0306385 A1 | 12/2009 | Walters et al. | |
| 2010/0007273 A1 | 1/2010 | Djurovich et al. | |
| 2010/0219403 A1 | 9/2010 | Langer et al. | |
| 2012/0012821 A1 | 1/2012 | Langer et al. | |
| 2012/0104378 A1 | 5/2012 | Djurovich et al. | |

(Continued)

FOREIGN PATENT DOCUMENTS

| | | |
|---|---|---|
| EP | 1 097 981 A2 | 5/2001 |
| EP | 1 658 343 A2 | 5/2006 |

(Continued)

OTHER PUBLICATIONS

International Search Report and Written Opinion issued Nov. 8, 2012, in International Application No. PCT/IB2012/052963.

(Continued)

*Primary Examiner* — Bijan Ahvazi
*Assistant Examiner* — Catherine S Branch
(74) *Attorney, Agent, or Firm* — Oblon, McClelland, Maier & Neustadt, L.L.P.

(57) ABSTRACT

The present invention relates to metal-carbene complexes comprising a central atom selected from iridium and platinum, and specific azabenzimidazolocarbene ligands, to OLEDs (Organic Light Emitting Diode, OLED) which comprise such complexes, to a device selected from the group consisting of illuminating elements, stationary visual display units and mobile visual display units comprising such an OLED, to the use of such a metal-carbene complex in OLEDs, for example as emitter, matrix material, charge transport material and/or charge or exciton blocker.

16 Claims, No Drawings

(56) References Cited

U.S. PATENT DOCUMENTS

| | | | | |
|---|---|---|---|---|
| 2012/0212126 A1* | 8/2012 | Tsai et al. | | 313/504 |
| 2012/0228583 A1* | 9/2012 | Wu et al. | | 257/40 |
| 2013/0032766 A1* | 2/2013 | Molt et al. | | 252/519.2 |
| 2014/0110691 A1* | 4/2014 | Lin et al. | | 257/40 |

FOREIGN PATENT DOCUMENTS

| | | |
|---|---|---|
| EP | 1 786 050 A1 | 5/2007 |
| EP | 1 837 926 B1 | 5/2008 |
| EP | 1 970 371 A1 | 9/2008 |
| EP | 1 988 587 A1 | 11/2008 |
| EP | 2 180 029 A1 | 4/2010 |
| JP | 2008-21687 A | 1/2008 |
| JP | 2008-66569 A | 3/2008 |
| JP | 2008-74939 A | 4/2008 |
| JP | 2008-84913 A | 4/2008 |
| JP | 2008-127326 A | 6/2008 |
| JP | 2008-207520 A | 9/2008 |
| JP | 2009-21336 A | 1/2009 |
| JP | 2009-59767 A | 3/2009 |
| JP | 2009-114369 A | 5/2009 |
| JP | 2009-114370 A | 5/2009 |
| JP | 2009-135183 A | 6/2009 |
| JP | 2009-170764 A | 7/2009 |
| JP | 2009-182298 A | 8/2009 |
| JP | WO 2009/104488 A1 | 8/2009 |
| JP | 2009-267255 A | 11/2009 |
| JP | 2010-21336 A | 1/2010 |
| JP | 2010-40830 A | 2/2010 |
| JP | 2010-114180 A | 5/2010 |
| JP | 2010-135467 A | 6/2010 |
| WO | WO 00/32717 A1 | 6/2000 |
| WO | WO 00/70655 A2 | 11/2000 |
| WO | WO 02/15645 A1 | 2/2002 |
| WO | WO 2005/019365 A2 | 3/2005 |
| WO | WO 2005/019373 A2 | 3/2005 |
| WO | WO 2005/113704 A2 | 12/2005 |
| WO | WO 2006/056418 A2 | 6/2006 |
| WO | WO 2005/121811 A1 | 11/2006 |
| WO | WO 2006/128800 A1 | 12/2006 |
| WO | WO 2007/077810 A1 | 7/2007 |
| WO | WO 2007/108362 A1 | 9/2007 |
| WO | WO 2007/108459 A1 | 9/2007 |
| WO | WO 2007/114244 A1 | 10/2007 |
| WO | WO 2007/115970 A1 | 10/2007 |
| WO | WO 2007/115981 A1 | 10/2007 |
| WO | WO 2007/119816 A1 | 10/2007 |
| WO | WO 2008/000727 A1 | 1/2008 |
| WO | WO 2008/029652 A1 | 3/2008 |
| WO | WO 2008/029729 A1 | 3/2008 |
| WO | WO 2008/034758 A2 | 3/2008 |
| WO | WO 2008/034758 A3 | 3/2008 |
| WO | WO 2008/035571 A1 | 3/2008 |
| WO | WO 2008/075296 A1 | 6/2008 |
| WO | WO 2008/090912 A1 | 7/2008 |
| WO | WO 2008/140114 A1 | 11/2008 |
| WO | WO 2008/146838 A1 | 12/2008 |
| WO | WO 2008/156105 A1 | 12/2008 |
| WO | WO 2009/003898 A1 | 1/2009 |
| WO | WO 2009/003919 A1 | 1/2009 |
| WO | WO 2009/008099 A1 | 1/2009 |
| WO | WO 2009/008100 A1 | 1/2009 |
| WO | WO 2009/046266 A1 | 4/2009 |
| WO | WO 2009/060742 A1 | 5/2009 |
| WO | WO 2009/060757 A1 | 5/2009 |
| WO | WO 2009/060779 A1 | 5/2009 |
| WO | WO 2009/060780 A1 | 5/2009 |
| WO | WO 2009/063757 A1 | 5/2009 |
| WO | WO 2009/084413 A1 | 7/2009 |
| WO | WO 2009/086028 A2 | 7/2009 |
| WO | WO 2009/086028 A3 | 7/2009 |
| WO | WO 2010/001830 A1 | 1/2010 |
| WO | WO 2010/004877 A1 | 1/2010 |
| WO | WO 2010/040777 A1 | 4/2010 |
| WO | WO 2010/044342 A1 | 4/2010 |
| WO | WO 2010/067746 A1 | 6/2010 |
| WO | WO 2010/079051 A1 | 7/2010 |
| WO | WO 2010/079678 A1 | 7/2010 |
| WO | WO 2010/087222 A1 | 8/2010 |
| WO | WO 2010/090077 A1 | 8/2010 |
| WO | WO 2010/095564 A1 | 8/2010 |
| WO | WO 2011/051404 A1 | 5/2011 |
| WO | WO 2011/073149 A1 | 6/2011 |

OTHER PUBLICATIONS

U.S. Appl. No. 13/516,117, filed Aug. 27, 2012, Molt, et al.
U.S. Appl. No. 14/238,382, filed Feb. 11, 2014, Suraru et al.

* cited by examiner

METAL COMPLEXES COMPRISING AZABENZIMIDAZOLE CARBENE LIGANDS AND THE USE THEREOF IN OLEDS

CROSS-REFERENCE TO RELATED APPLICATIONS

This application is based upon and claims the benefit of priority to U.S. Provisional Application No. 61/496,646 filed on Jun. 14, 2011.

DESCRIPTION

The present invention relates to metal-carbene complexes comprising a central atom selected from iridium and platinum, and specific azabenzimidazole carbene ligands, to OLEDs (Organic Light-Emitting Diodes) which comprise such complexes, to a device selected from the group consisting of illuminating elements, stationary visual display units and mobile visual display units comprising such an OLED, to the use of such a metal-carbene complex in OLEDs, for example as emitter, matrix material, charge transport material and/or charge or exciton blocker.

Organic light-emitting diodes (OLEDs) exploit the propensity of materials to emit light when they are excited by electrical current. OLEDs are of particular interest as an alternative to cathode ray tubes and liquid-crystal displays for production of flat visual display units. Owing to the very compact design and the intrinsically low power consumption, devices comprising OLEDs are suitable especially for mobile applications, for example for applications in cellphones, smartphones, digital cameras, mp3 players, laptops, etc. In addition, white OLEDs give great advantages over the illumination technologies known to date, especially a particularly high efficiency.

The prior art proposes numerous materials which emit light on excitation by electrical current.

WO 2005/019373 discloses the use of transition metal complexes comprising at least one carbene ligand in OLEDs. According to WO2005/019373, a new compound class has been found, which is suitable for electroluminescence in the blue, red and green region of the electromagnetic spectrum, which enables the production of full-color displays.

WO 2006/056418 A2 discloses the use of transition metal-carbene complexes having at least one unsymmetrically substituted carbene ligand in organic light-emitting diodes. The transition metal-carbene complexes are suitable for electroluminescence in the blue, red and green region of the electromagnetic spectrum. Among the disclosed carbene complexes with numerous different carbene ligands, a homoleptic carbene complex with a specific azabenzimidazole carbene ligand is mentioned, though it is not described as advantageous over the further carbene complexes disclosed. However, this carbene complex differs from the carbene complexes according to the present application.

WO 2005/113704 A2 relates to luminescent compounds having carbene ligands. WO 2005/113704 A2 discloses numerous different types of carbene ligands. Among the disclosed carbene complexes with numerous different carbene ligands, a homoleptic carbene complex with a specific azabenzimidazole carbene ligand is mentioned, though this is not described as advantageous over the further carbene complexes disclosed. However, this carbene complex differs from the carbene complexes according to the present application.

WO 2009/046266 A1 discloses complexes with tridentate ligands. The tridentate ligands mentioned include tridentate carbene ligands, and these tridentate carbene ligands may bear, for example, two azabenzimidazole substituents. The carbene complexes according to the present application differ from the carbene complexes disclosed in WO 2009/046266 A1 especially in that they do not comprise any tridentate carbene ligands.

Even though there are already known carbene complexes based on azabenzimidazole carbene ligands which are suitable for use in OLEDs, especially as light-emitting substances, it is desirable to provide more stable and/or more efficient compounds which are usable in industry. In addition, the light-emitting substances which emit in the blue region of the electromagnetic spectrum (400 nm to 500 nm), especially in the deep blue region of the electromagnetic spectrum (400 nm to 470 nm), are desirable. In the context of the present invention, electroluminescence is understood to mean both electrofluorescence and electrophosphorescence.

It is therefore an object of the present invention to provide iridium and platinum complexes which are suitable for use in organic electronic components. More particularly, the iridium and platinum complexes shall be suitable for use in OLEDs as emitters, matrix material, charge transport material, or charge blockers. The complexes shall be particularly suitable for electroluminescence in the blue region, more particularly in the deep blue region, of the electromagnetic spectrum, which enables, for example, the production of full-color displays and white OLEDs. It is a further object of the present invention to provide corresponding complexes which can be used as a mixture with a host compound (matrix material) or as a pure layer as a light-emitting layer in OLEDs. More particularly, it is desirable to provide transition metal complexes which exhibit a spectrum of properties improved over known transition metal complexes, for example improved efficiencies, improved CIE color coordinates and/or improved lifetime/stability.

These objects are achieved in accordance with the invention by the production of metal-carbene complexes of the general formula (I)

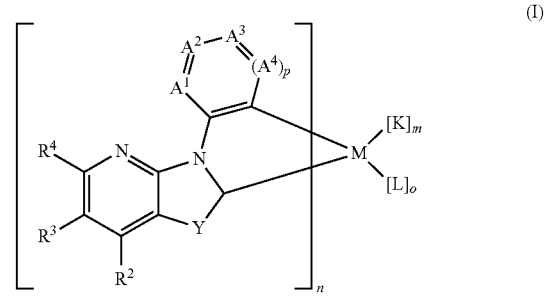

where M, n, Y, $R^2$, $R^3$, $R^4$, $A^1$, $A^2$, $A^3$, $A^4$, p, K, L, m and o are each defined as follows:

M is Ir or Pt,
n is an integer selected from 1, 2 and 3, where the ligand(s)

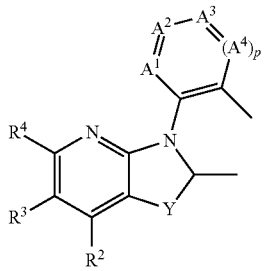

are each bidentate ligands;
Y is $NR^1$, O, S or $C(R^{10})_2$,
$R^1$ is a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms,
$R^2$, $R^3$, $R^4$ are each independently hydrogen, a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action,
or
$R^2$ and $R^3$ or $R^3$ and $R^4$ together with the carbon atoms to which they are bonded form an optionally substituted, saturated or unsaturated or aromatic ring optionally interrupted by at least one further heteroatom and having a total of 5 to 18 carbon atoms and/or heteroatoms, and may optionally be fused to at least one further optionally substituted saturated or unsaturated or aromatic ring optionally interrupted by at least one further heteroatom and having a total of 5 to 18 carbon atoms and/or heteroatoms,
$A^1$ is $CR^6$ or N;
$A^2$ is $CR^7$ or N;
$A^3$ is $CR^8$ or N;
$A^4$ is $CR^9$ or N;
$R^6$, $R^7$, $R^8$, $R^9$ are each independently hydrogen, a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted heterocycloalkyl radical optionally interrupted by at least one heteroatom, optionally bearing at least one functional group and having 3 to 20 carbon atoms and/or heteroatoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action,
or
$R^6$ and $R^7$, $R^7$ and $R^8$ or $R^8$ and $R^9$, together with the carbon atoms to which they are bonded, form a saturated, unsaturated or aromatic, optionally substituted ring which is optionally interrupted by at least one heteroatom, has a total of 5 to 18 carbon atoms and/or heteroatoms, and may optionally be fused to at least one further optionally substituted saturated or unsaturated or aromatic ring optionally interrupted by at least one further heteroatom and having a total of 5 to 18 carbon atoms and/or heteroatoms,
p is 0 or 1;
$R^{10}$ is independently a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms,
or
the two $R^{19}$ radicals form, together with the carbon atom to which they are bonded, a saturated or unsaturated optionally substituted ring optionally interrupted by at least one heteroatom and having a total of 5 to 18 carbon atoms and/or heteroatoms;
K is an uncharged mono- or bidentate ligand,
L is a mono- or dianionic ligand, preferably monoanionic ligand, which may be mono- or bidentate,
m is 0, 1 or 2, where, when m is 2, the K ligands may be the same or different,
o is 0, 1 or 2, where, when o is 2, the L ligands may be the same or different, excluding ligands L of the following general formula (A):

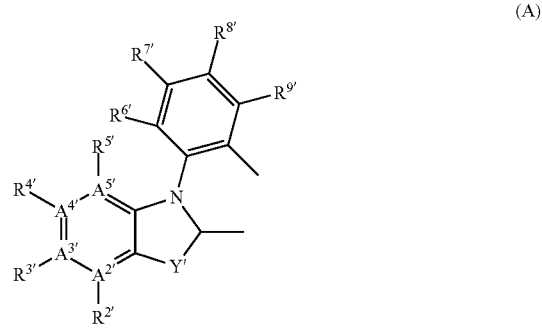

(A)

where Y', $A^{2'}$, $A^{3'}$, $A^{4'}$, $A^{5'}$, $R^{1'}$, $R^{2'}$, $R^{3'}$, $R^{4'}$, $R^{5'}$, $R^{6'}$, $R^{7'}$, $R^{8'}$, $R^{9'}$ and $R^{10'}$ are each defined as follows:

Y' is $NR^{1'}$, O, S or $C(R^{10'})_2$, $A^{2'}$, $A^{3'}$, $A^{4'}$, $A^{5'}$ are each independently N or C, where 2 A'=nitrogen atoms and at least one carbon atom is present between two nitrogen atoms in the ring, $R^{1'}$ is a linear or branched alkyl radical optionally bearing at least one functional group, optionally interrupted by at least one heteroatom and having 1 to 20 carbon atoms, cycloalkyl radical having 3 to 20 carbon atoms, substituted or unsubstituted aryl radical having 6 to 30 carbon atoms, substituted or unsubstituted heteroaryl radical having a total of 5 to 18 carbon atoms and/or heteroatoms, $R^{2'}$, $R^{3'}$, $R^{4'}$, $R^{5'}$, if $A^{2'}$, $A^{3'}$, $A^{4'}$ and/or $A^{5'}$ is N, are each a free electron pair or, if $A^{2'}$, $A^{3'}$, $A^{4'}$ and/or $A^{5'}$ is C, are each independently hydrogen, a linear or branched alkyl radical optionally bearing at least one functional group, optionally interrupted by at least one heteroatom and having 1 to 20 carbon atoms, cycloalkyl radical having 3 to 20 carbon atoms, substituted or unsubstituted aryl radical having 6 to 30 carbon atoms, substituted or unsubstituted heteroaryl radical having a total of 5 to 18 carbon atoms and/or heteroatoms, group with donor or acceptor action or $R^{3'}$ and $R^{4'}$ form, together with $A^{3'}$ and $A^{4'}$, an optionally substituted, unsaturated ring optionally interrupted by at least one further heteroatom and having a total of 5 to 18 carbon atoms and/or heteroatoms, $R^{6'}$, $R^{7'}$, $R^{8'}$, $R^{9'}$ are each independently hydrogen, a linear or branched alkyl radical optionally bearing at least one functional group, optionally interrupted by at least one heteroatom and having 1 to 20 carbon atoms, cycloalkyl radical having 3 to 20 carbon atoms, cycloheteroalkyl radical having 3 to 20 carbon atoms, substituted or unsubstituted aryl radical having 6 to 30 carbon atoms, substituted or unsubstituted heteroaryl radical having a total of 5 to 18 carbon atoms and/or heteroatoms, group with donor or acceptor action or $R^{6'}$ and $R^{7'}$, $R^{7'}$ and $R^{8'}$ or $R^{8'}$ and $R^{9'}$, together with the carbon atoms to which they are bonded, form an unsaturated or aromatic, optionally substituted ring optionally interrupted by at least one heteroatom and having a total of 5 to 18 carbon atoms and/or heteroatoms, and/or if $A^{5'}$ is C, $R^{5'}$ and $R^{6'}$ together form a saturated or unsaturated, linear or branched bridge optionally comprising heteroatoms, aromatic unit, heteroaromatic unit and/or functional groups and having a total of 1 to 30 carbon atoms and/or heteroatoms, to which is optionally fused a substituted or unsubstituted, five- to eight-membered ring comprising carbon atoms and/or heteroatoms, $R^{10'}$ is independently a linear or branched alkyl radical optionally bearing at least one functional group, optionally interrupted by at least one heteroatom and having 1 to 20 carbon atoms, cycloalkyl radical having 3 to 20 carbon atoms, substituted or unsubstituted aryl radical having 6 to 30 carbon atoms, substituted or unsubstituted heteroaryl radical having a total of 5 to 18 carbon atoms and/or heteroatoms.

Preferably, in the metal-carbene complexes of the general formula (I), p is 1, which means that preferred metal-carbene complexes of the formula (I) have the following formula:

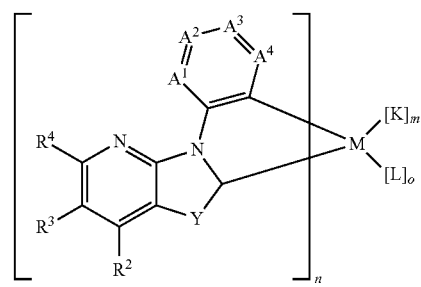

where the radicals and indices mentioned are each as defined above and below for the formula (I).

In a particularly preferred embodiment, m and o in formula (I) are each 0 and the n carbene ligands of the formula

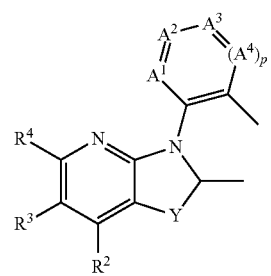

in the metal-carbene complex of the general formula (I) are identical, which means that the complexes are homoleptic metal-carbene complexes of the general formula (I). This means that n is 3 in the case when M is Ir, and n is 2 in the case when M is Pt.

In principle—in a preferred embodiment—the n carbene ligands in the metal-carbene complex of the general formula (I) may also be different. In this case, the complex is a heteroleptic pure carbene complex of the formula (I) when m and n are each 0.

In a further preferred embodiment, o is 1 or 2 and L is a carbene ligand, suitable carbene ligands having been specified above. In this case, the complex is likewise a heteroleptic pure carbene complex of the formula (I).

In the context of the present invention, the terms aryl radical, unit or group, heteroaryl radical, unit or group, alkyl radical, unit or group, cycloalkyl radical, unit or group, cycloheteroalkyl radical, unit or group, and groups with donor or acceptor action are each defined as follows—unless stated otherwise:

Aryl radicals or substituted or unsubstituted aryl radicals having 6 to 30 carbon atoms ($C_6$-$C_{30}$-aryl radicals) refer in the present invention to radicals which are derived from monocyclic, bicyclic or tricyclic aromatics which do not comprise any ring heteroatoms. When the systems are not monocyclic systems, the term "aryl" for the second ring also includes the saturated form (perhydro form) or the partly unsaturated form (for example the dihydro form or tetrahydro form), provided that the particular forms are known and stable. This means that the term "aryl" in the present invention encompasses, for example, also bicyclic or tricyclic radicals in which either both or all three radicals are aromatic, and bicyclic or tricyclic radicals in which only one ring is aromatic, and also tricyclic radicals in which two rings are aromatic. Examples of aryl are: phenyl, naphthyl, indanyl, 1,2-dihydronaphthenyl, 1,4-dihydronaphthenyl, indenyl, anthracenyl, phenanthrenyl or 1,2,3,4-tetrahydronaphthyl. Particular preference is given to $C_6$-$C_{10}$-aryl radicals, for example phenyl or naphthyl, very particular preference to $C_6$-aryl radicals, for example phenyl.

The aryl radicals or $C_6$-$C_{30}$-aryl radicals may be unsubstituted or substituted by one or more further radicals. Suitable further radicals are selected from the group consisting of $C_1$-$C_{20}$-alkyl, $C_6$-$C_{30}$-aryl and substituents with donor or acceptor action, suitable substituents with donor or acceptor action having been specified above. The $C_6$-$C_{30}$-aryl radicals are preferably unsubstituted or substituted by one or more $C_1$-$C_{20}$-alkyl groups, $C_1$-$C_{20}$-alkoxy groups, CN, $CF_3$, F or amino groups ($NR^{32}R^{33}$ where suitable $R^{32}$ and $R^{33}$ radicals are specified below).

Heteroaryl radicals or substituted or unsubstituted heteroaryl radicals having a total of 5 to 18 carbon atoms and/or heteroatoms are understood to mean monocyclic, bicyclic or tricyclic heteroaromatics, some of which can be derived from the aforementioned aryl, in which at least one carbon atom in the aryl base structure has been replaced by a heteroatom. Preferred heteroatoms are N, O and S. The heteroaryl radicals more preferably have 5 to 13 ring atoms. The base structure of the heteroaryl radicals is especially preferably selected from systems such as pyridine and five-membered heteroaromatics such as thiophene, pyrrole, imidazole, thiazole, oxazole or furan. These base structures may optionally be fused to one or two six-membered aromatic radicals. Suitable fused heteroaromatics are carbazolyl, benzimidazolyl, benzofuryl, benzothiazole, benzoxazole, dibenzofuryl or dibenzothiophenyl.

The base structure may be substituted at one, more than one or all substitutable positions, suitable substituents being the same as those already specified under the definition of $C_6$-$C_{30}$-aryl. However, the heteroaryl radicals are preferably unsubstituted. Suitable heteroaryl radicals are, for example, pyridin-2-yl, pyridin-3-yl, pyridin-4-yl, thiophen-2-yl, thiophen-3-yl, furan-2-yl, furan-3-yl, thiazol-2-yl, oxazol-2-yl and imidazol-2-yl, and the corresponding benzofused radicals, especially carbazolyl, benzimidazolyl, benzofuryl, benzothiazole, benzoxazole, dibenzofuryl or dibenzothiophenyl.

An alkyl radical in the context of the present application is a linear or branched alkyl radical optionally bearing at least one functional group, optionally interrupted by at least one heteroatom and having 1 to 20 carbon atoms. Preference is given to $C_1$- to $C_{10}$-alkyl radicals, particular preference to $C_1$- to $C_6$-alkyl radicals. In addition, the alkyl radicals may be substituted by one or more functional groups, preferably selected from the group consisting of $C_1$-$C_{20}$-alkyl, $C_1$-$C_{20}$-alkoxy, halogen, preferably F, $C_1$-$C_{20}$-haloalkyl, e.g. $CF_3$, and $C_6$-$C_{30}$-aryl which may in turn be substituted or unsubstituted. Suitable aryl substituents and suitable alkoxy and halogen substituents are specified below. Examples of suitable alkyl groups are methyl, ethyl, propyl, butyl, pentyl, hexyl, heptyl and octyl, and also $C_1$-$C_{20}$-alkyl-, $C_1$-$C_{20}$-haloalkyl-, $C_6$-$C_{30}$-aryl-, $C_1$-$C_{20}$-alkoxy- and/or halogen-substituted, especially F-substituted, derivatives of the alkyl groups mentioned, for example $CF_3$. This comprises both the n-isomers of the radicals mentioned and branched isomers such as isopropyl, isobutyl, isopentyl, sec-butyl, tert-butyl, neopentyl, 3,3-dimethylbutyl, 3-ethylhexyl, etc. Preferred alkyl groups are methyl, ethyl, isopropyl, tert-butyl and $CF_3$.

A cycloalkyl radical or a substituted or unsubstituted cycloalkyl radical having 3 to 20 carbon atoms is understood in the context of the present application to mean a substituted or unsubstituted $C_3$-$C_{20}$-cycloalkyl radical. Preferred are cycloalkyl radicals having 5 to 20, more preferably 5 to 10 and most preferably 5 to 8 carbon atoms in the base structure (ring) to understand. Suitable substituents are the substituents mentioned for the alkyl groups. Examples of suitable cycloalkyl groups, which may be unsubstituted or substituted by the radicals mentioned above for the alkyl groups, are cyclopentyl, cyclohexyl, cycloheptyl, cyclooctyl, cyclononyl and cyclodecyl. They may also be polycyclic ring systems such as decalinyl, norbornyl, bornanyl or adamantyl.

A heterocycloalkyl radical or a substituted or unsubstituted heterocycloalkyl radical having 3 to 20 carbon atoms and/or heteroatoms is understood to mean heterocycloalkyl radicals having 3 to 20, preferably 5 to 10 and more preferably 5 to 8 ring atoms, where at least one carbon atom in the heterocycloalkyl base structure has been replaced by a heteroatom. Preferred heteroatoms are N, O and S. Suitable substituents are the substituents mentioned for the alkyl groups. Examples of suitable heterocycloalkyl groups, which may be unsubstituted or substituted by the radicals mentioned above for the alkyl groups, are radicals derived from the following heterocycles: pyrrolidine, thiolane, tetrahydrofuran, 1,2-oxathiolane, oxazolidine, piperidine, thiane, oxane, dioxane, 1,3-dithiane, morpholine, piperazine. They may also be polycyclic ring systems.

Suitable alkoxy radicals and alkylthio radicals derive correspondingly from the aforementioned alkyl radicals. Examples here include $OCH_3$, $OC_2H_5$, $OC_3H_7$, $OC_4H_9$ and $OC_8H_{17}$, and also $SCH_3$, $SC_2H_5$, $SC_3H_7$, $SC_4H_9$ and $SC_8H_{17}$. In this context, $C_3H_7$, $C_4H_9$ and $C_8H_{17}$ comprise both the n-isomers and branched isomers such as isopropyl, isobutyl, sec-butyl, tert-butyl and 2-ethylhexyl. Particularly preferred alkoxy or alkylthio groups are methoxy, ethoxy, n-octyloxy, 2-ethylhexyloxy and $SCH_3$.

Suitable halogen radicals or halogen substituents in the context of the present application are fluorine, chlorine, bromine and iodine, preferably fluorine, chlorine and bromine, more preferably fluorine and chlorine, most preferably fluorine.

In the context of the present application, groups with donor or acceptor action are understood to mean the following groups:

$C_1$-$C_{20}$-alkoxy, $C_6$-$C_{30}$-aryloxy, $C_1$-$C_{20}$-alkylthio, $C_6$-$C_{30}$-arylthio, $SiR^{32}R^{33}R^{34}$, halogen radicals, halogenated $C_1$-$C_{20}$-alkyl radicals, carbonyl (—CO($R^{32}$)), carbonylthio (—C=O ($SR^{32}$)), carbonyloxy (—C=O($OR^{32}$)), oxycarbonyl (—OC=O($R^{32}$)), thiocarbonyl (—SC=O ($R^{32}$)), amino (—$NR^{32}R^{33}$), OH, pseudohalogen radicals, amido (—C=O($NR^{32}R^{33}$)), —$NR^{32}$C=O($R^{33}$), phosphonate (—P(O)($OR^{32}$)$_2$, phosphate (—OP(O)($OR^{32}$)$_2$), phosphine (—$PR^{32}R^{33}$), phosphine oxide (—P(O)$R^{32}{}_2$), sulfate (—OS(O)$_2$$OR^{32}$), sulfoxide (—S(O)$R^{32}$), sulfonate (—S(O)$_2$$OR^{32}$), sulfonyl (—S(O)$_2$$R^{32}$), sulfonamide (—S(O)$_2$$NR^{32}R^{33}$), $NO_2$, boronic esters (—OB($OR^{32}$)$_2$), imino (—C=$NR^{32}R^{33}$)), borane radicals, stannate radicals, hydrazine radicals, hydrazone radicals, oxime radicals, nitroso groups, diazo groups, vinyl groups, sulfoximines, alanes, germanes, boroxines and borazines.

Preferred substituents with donor or acceptor action are selected from the group consisting of:

$C_1$- to $C_{20}$-alkoxy, preferably $C_1$-$C_6$-alkoxy, more preferably ethoxy or methoxy; $C_6$-$C_{30}$-aryloxy, preferably $C_6$-$C_{10}$-aryloxy, more preferably phenyloxy; $SiR^{32}R^{33}R^{34}$, where $R^{32}$, $R^{33}$ and $R^{34}$ are preferably each independently substituted or unsubstituted alkyl or substituted or unsubstituted phenyl, suitable substituents having been specified above; halogen radicals, preferably F, Cl, Br, more preferably F or Cl, most preferably F, halogenated $C_1$-$C_{20}$-alkyl radicals, preferably halogenated $C_1$-$C_6$-alkyl radicals, most preferably fluorinated $C_1$-$C_6$-alkyl radicals, e.g. $CF_3$, $CH_2F$, $CHF_2$ or $C_2F_5$; amino, preferably dimethylamino, diethylamino or diphenylamino; OH, pseudohalogen radicals, preferably CN, SCN or OCN, more preferably CN, —C(O)OC$_1$-C$_4$-alkyl, preferably —C(O)OMe, P(O)R$_2$, preferably P(O)Ph$_2$, and SO$_2$R$_2$, preferably SO$_2$Ph.

Very particularly preferred substituents with donor or acceptor action are selected from the group consisting of methoxy, phenyloxy, halogenated C$_1$-C$_4$-alkyl, preferably CF$_3$, CH$_2$F, CHF$_2$, C$_2$F$_5$, halogen, preferably F, CN, SiR$^{32}$R$^{33}$R$^{34}$, where suitable R$^{32}$, R$^{33}$ and R$^{34}$ radicals have been specified above, diphenylamino, —C(O)OC$_1$-C$_4$-alkyl, preferably —C(O)OMe, P(O)Ph$_2$ and SO$_2$Ph.

The aforementioned groups with donor or acceptor action are not intended to rule out the possibility that further radicals and groups among those specified above may also have donor or acceptor action. For example, the aforementioned heteroaryl radicals are likewise groups with donor or acceptor action, and the C$_1$-C$_{20}$-alkyl radicals are groups with donor action.

The R$^{32}$, R$^{33}$ and R$^{34}$ radicals mentioned in the aforementioned groups with donor or acceptor action have the definitions already mentioned above, which means that R$^{32}$, R$^{33}$ and R$^{34}$ are each independently:

Hydrogen, substituted or unsubstituted C$_1$-C$_{20}$-alkyl or substituted or unsubstituted C$_6$-C$_{30}$-aryl or substituted or unsubstituted heteroaryl having 5 to 30 ring atoms, suitable and preferred alkyl and aryl radicals having been specified above. More preferably, the R$^{32}$, R$^{33}$ and R$^{34}$ radicals are C$_1$-C$_6$-alkyl, e.g. methyl, ethyl, i-propyl or tert-butyl, or phenyl or pyridyl.

K in the general formula (I) is an uncharged mono- or bidentate ligand, and L in the general formula (I) is a mono- or dianionic ligand, preferably a monoanionic ligand which may be mono- or bidentate.

Ligands L with the following general formula (A) are excluded according to the present application:

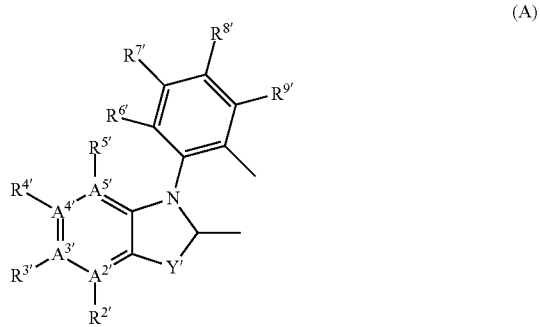

(A)

where Y', A$^{2'}$, A$^{3'}$, A$^{4'}$, A$^{5'}$, R$^{1'}$, R$^{2'}$, R$^{3'}$, R$^{4'}$, R$^{5'}$, R$^{6'}$, R$^{7'}$, R$^{8'}$, R$^{9'}$ and R$^{10'}$ are each defined as follows:

Y' is NR$^{1'}$, O, S or C(R$^{10'}$)$_2$,

A$^{2'}$, A$^{3'}$, A$^{4'}$, A$^{5'}$ are each independently N or C, where 2 A'=nitrogen atoms and at least one carbon atom is present between two nitrogen atoms in the ring, R$^{1'}$ is a linear or branched alkyl radical optionally bearing at least one functional group, optionally interrupted by at least one heteroatom and having 1 to 20 carbon atoms, cycloalkyl radical having 3 to 20 carbon atoms, substituted or unsubstituted aryl radical having 6 to 30 carbon atoms, substituted or unsubstituted heteroaryl radical having a total of 5 to 18 carbon atoms and/or heteroatoms, R$^{2'}$, R$^{3'}$, R$^{4'}$, R$^{5'}$, if A$^{2'}$, A$^{3'}$, A$^{4'}$ and/or A$^{5'}$ is N, are each a free electron pair or, if A$^{2'}$, A$^{3'}$, A$^{4'}$ and/or A$^{5'}$ is C, are each independently hydrogen, a linear or branched alkyl radical optionally bearing at least one functional group, optionally interrupted by at least one heteroatom and having 1 to 20 carbon atoms, cycloalkyl radical having 3 to 20 carbon atoms, substituted or unsubstituted aryl radical having 6 to 30 carbon atoms, substituted or unsubstituted heteroaryl radical having a total of 5 to 18 carbon atoms and/or heteroatoms, group with donor or acceptor action or R$^{3'}$ and R$^{4'}$ form, together with A$^{3'}$ and A$^{4'}$, an optionally substituted, unsaturated ring optionally interrupted by at least one further heteroatom and having a total of 5 to 18 carbon atoms and/or heteroatoms, R$^{6'}$, R$^{7'}$, R$^{8'}$, R$^{9'}$ are each independently hydrogen, a linear or branched alkyl radical optionally bearing at least one functional group, optionally interrupted by at least one heteroatom and having 1 to 20 carbon atoms, cycloalkyl radical having 3 to 20 carbon atoms, cycloheteroalkyl radical having 3 to 20 carbon atoms, substituted or unsubstituted aryl radical having 6 to 30 carbon atoms, substituted or unsubstituted heteroaryl radical having a total of 5 to 18 carbon atoms and/or heteroatoms, group with donor or acceptor action or R$^{6'}$ and R$^{7'}$, R$^{7'}$ and R$^{8'}$ or R$^{8'}$ and R$^{9'}$, together with the carbon atoms to which they are bonded, form a saturated, unsaturated or aromatic, optionally substituted ring optionally interrupted by at least one heteroatom and having a total of 5 to 18 carbon atoms and/or heteroatoms, and/or if A$^{5'}$ is C, R$^{5'}$ and R$^{6'}$ together form a saturated or unsaturated, linear or branched bridge optionally comprising heteroatoms, aromatic unit, heteroaromatic unit and/or functional groups and having a total of 1 to 30 carbon atoms and/or heteroatoms, to which is optionally fused a substituted or unsubstituted, five- to eight-membered ring comprising carbon atoms and/or heteroatoms, R$^{10'}$ is independently a linear or branched alkyl radical optionally bearing at least one functional group, optionally interrupted by at least one heteroatom and having 1 to 20 carbon atoms, cycloalkyl radical having 3 to 20 carbon atoms, substituted or unsubstituted aryl radical having 6 to 30 carbon atoms, substituted or unsubstituted heteroaryl radical having a total of 5 to 18 carbon atoms and/or heteroatoms.

A bidentate ligand is understood to mean a ligand coordinated at two sites to the transition metal atom M. A monodentate ligand is understood to mean a ligand coordinated at one site on the ligand to the transition metal atom M.

According to the invention, the n carbene ligands

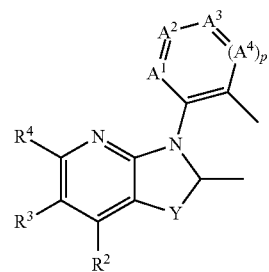

in the metal-carbene complexes of the formula (I) are bidentate ligands.

Suitable uncharged mono- or bidentate ligands K are preferably selected from the group consisting of phosphines, both mono- and bisphosphines; phosphonates, both mono- and bisphosphonates, and derivatives thereof, arsenates, both mono- and bisarsenates, and derivatives thereof; phosphites, both mono- and bisphosphites; CO; pyridines, both mono- and bispyridines; nitriles, dinitriles, allyl, diimines, nonconjugated dienes and conjugated dienes which form a π complex with $M^1$. Particularly preferred uncharged mono- or bidentate ligands K are selected from the group consisting of phosphines, both mono- and bisphosphines, preferably trialkyl-, triaryl- or alkylaryiphosphines, more preferably $PAr_3$ where Ar is a substituted or unsubstituted aryl radical and the three aryl radicals in $PAr_3$ may be the same or different, more preferably $PPh_3$, $PEt_3$, $PnBu_3$, $PEt_2Ph$, $PMe_2Ph$, $PnBu_2Ph$; phosphonates and derivatives thereof, arsenates and derivatives thereof, phosphites, CO; pyridines, both mono- and bispyridines, where the pyridines may be substituted by alkyl or aryl groups; nitriles and dienes which form a π complex with $M^1$, preferably $\eta^4$-diphenyl-1,3-butadiene, $\eta^4$-1,3-pentadiene, $\eta^4$-1-phenyl-1,3-pentadiene, $\eta^4$-1,4-dibenzyl-1,3-butadiene, $\eta^4$-2,4-hexadiene, $\eta^4$-3-methyl-1,3-pentadiene, $\eta^4$-1,4-ditolyl-1,3-butadiene, $\eta^4$-1,4-bis(trimethylsilyl)-1,3-butadiene and $\eta^2$- or $\eta^4$-cyclooctadiene (each 1,3 and each 1,5), more preferably 1,4-diphenyl-1,3-butadiene, 1-phenyl-1,3-pentadiene, 2,4-hexadiene, butadiene, $\eta^2$-cyclooctene, $\eta^4$-cyclooctadiene and $\eta^4$-1,5-cyclooctadiene. Very particularly preferred uncharged monodentate ligands are selected from the group consisting of $PPh_3$, $P(OPh)_3$, $AsPh_3$, CO, pyridine, nitriles and derivatives thereof. Suitable uncharged mono- or bidentate ligands are preferably 1,4-diphenyl-1,3-butadiene, 1-phenyl-1,3-pentadiene, 2,4-hexadiene, $\eta^4$-cyclooctadiene and $\eta^2$-cyclooctadiene (each 1,3 and each 1,5).

Suitable mono- or dianionic ligands L, preferably monoanionic ligands L which may be mono- or bidentate, are the ligands typically used as mono- or bidentate mono- or dianionic ligands, excluding ligands of the aforementioned general formula (A).

Suitable monoanionic monodentate ligands are, for example, halides, especially $Cl^-$ and $Br^-$, pseudohalides, especially $CN^-$, cyclopentadienyl ($Cp^-$), hydride, alkyl radicals joined to the transition metal M via a sigma bond, for example $CH_3$, alkylaryl radicals joined to the transition metal M via a sigma bond, for example benzyl.

Suitable monoanionic bidentate ligands are, for example, ligands of the formula (B)

(B)

in which
R$^{51}$ is in each case independently a linear or branched alkyl radical having 1 to 6 carbons atoms, preferably methyl, ethyl, isopropyl, tert-butyl, $CF_3$; substituted or unsubstituted aryl radical having 6 to 20 carbon atoms, preferably unsubstituted phenyl or 2,6-dialkylphenyl; substituted or unsubstituted heteroaryl radical having a total of 5 to 18 carbon atoms and/or heteroatoms,
R$^{52}$ is hydrogen, a linear or branched alkyl radical having 1 to 6 carbon atoms, substituted or unsubstituted aryl radical having 6 to 20 carbon atoms, preferably hydrogen;
where the ligand of the formula (B) is, for example, acetylacetonato or hexafluoro-acetylacetonato;

picolinato, salicylato, 8-hydroxyquinolato ligands derived from Schiff bases, ligands derived from amino acids, heterocyclic noncarbene ligands of the general formula (III) specified below, e.g. arylpyridines, e.g. phenylpyridine, and the further bidentate monoanionic ligands specified in WO 02/15645, carbene ligands of the general formula (II) specified below, and also carbene ligands as specified in WO2006056418 and in EP1658343, and arylazoles, e.g. 2-arylimidazoles.

Suitable dianionic bidentate ligands are, for example, dialkoxides, dicarbonates, dicarboxylates, diamides, diimides, dithiolates, biscyclopentadienyls, bisphosphonates, bissulfonates and 3-phenylpyrazole.

In a preferred embodiment, the present invention relates to an inventive metal-carbene complex where L in the general formula (I) is a carbene ligand of the general formula (II)

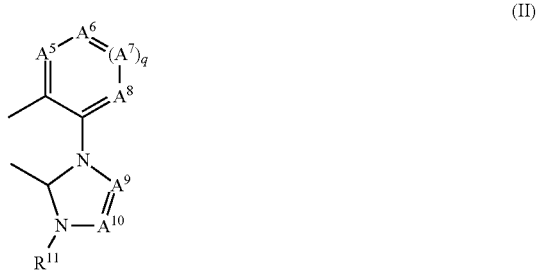

(II)

where
$A^9$ is $CR^{12}$ or N;
$A^{10}$ is $CR^{13}$ or N;
$R^{11}$ is a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted heterocycloalkyl radical optionally interrupted by at least one heteroatom, optionally bearing at least one functional group and having 3 to 20 carbon atoms and/or heteroatoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms,
$R^{12}$, $R^{13}$ are each independently hydrogen, a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted heterocycloalkyl radical optionally interrupted by at least one heteroatom, optionally bearing at least one functional group and having 3 to 20 carbon atoms and/or heteroatoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, $A^5$ is $CR^{14}$ or N;
$A^6$ is $CR^{15}$ or N;
$A^7$ is $CR^{16}$ or N;
$A^8$ is $CR^{17}$ or N;
$R^{14}$, $R^{15}$, $R^{16}$, $R^{17}$ are each independently hydrogen, a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted heterocycloalkyl radical optionally interrupted by at least one heteroatom, optionally bearing at least one functional group and having 3 to 20 carbon atoms and/or heteroatoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action,
or
$R^{14}$ and $R^{15}$, $R^{15}$ and $R^{16}$ or $R^{16}$ and $R^{17}$ form, together with the carbon atoms to which they are bonded, an unsaturated or aromatic, optionally substituted ring optionally interrupted by at least one heteroatom and having a total of 5 to 18 carbon atoms and/or heteroatoms,
and/or
$R^{12}$ and $R^{13}$ form, together with $A^9$ and $A^{19}$ to which they are bonded, an unsaturated or aromatic, optionally substituted ring optionally interrupted by exactly one heteroatom or two adjacent heteroatoms and having a total of 5 to 18 ring atoms,
and/or
if $A^9$ is $CR^{12}$, $R^{12}$ and $R^{17}$ together form a saturated or unsaturated, linear or branched bridge optionally comprising heteroatoms, aromatic units, heteroaromatic units and/or functional groups and having a total of 1 to 30 carbon atoms and/or heteroatoms, to which is optionally fused a substituted or unsubstituted, five- to eight-membered ring comprising carbon atoms and/or heteroatoms;
q is 0 or 1;
where—when o in formula (I) is 2, the carbene ligands L of the formula (II) may be the same or different.

In the case that the inventive metal-carbene complex of the formula (I) has two ligands L, the ligands L may each be an identical ligand of the formula (II) or different ligands of the formula (II). It is also possible that one of the ligands L is a ligand of the formula (II) and the second ligand is any ligand L. In a preferred embodiment, in the case that the inventive metal-carbene complex of the formula (I) has two ligands L, the ligands L are each an identical ligand of the formula (II).

In a preferred embodiment, the present invention relates to a metal-carbene complex of the general formula (I) which has exclusively carbene ligands.

In one embodiment, m and o in the metal-carbene complex of the general formula (I) are each 0. In this case, n is preferably 3 (when M is Ir(III)) or 2 (when M is Pt(II)). The n azabenzimidazole carbene ligands may each be the same or different in the metal-carbene complexes of the general formula (I). They are preferably the same, which means that, in a preferred embodiment, the present application relates to homoleptic metal-carbene complexes of the general formula (I).

In a further embodiment, m is 0, n is 1 or 2 and o is 1 or 2, where the o ligand(s) L is/are ligand(s) of the general formula (II). If n or o is 2, the particular n azabenzimidazole carbene ligands or o ligands L may be the same or different. In this case, the complexes are heteroleptic metal-carbene complexes having exclusively carbene ligands.

It has been found that metal-carbene complexes of the general formula (I) having exclusively carbene ligands are generally notable for light emission in the deep blue region of the electromagnetic spectrum.

The inventive metal-carbene complexes of the general formula (I) are therefore notable, in a preferred embodiment, for the following CIE values: CIE: y: generally <0.40, preferably 0.08 to 0.30, most preferably 0.15 to 0.25; x: generally <0.25, preferably 0.10 to 0.20, more preferably 0.14 to 0.20.

The metal-carbene complexes of the general formula (I) having exclusively carbene ligands are therefore suitable with particular preference as emitter material in OLEDs.

More preferably, M in the metal-carbene complexes of the formula (I) having exclusively carbene ligands is Ir.

In a further preferred embodiment, the present invention relates to an inventive metal-carbene complex where in the general formula (I), L is selected from the group consisting of a ligand of the formula (B)

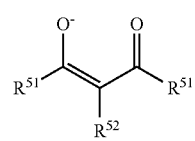

(B)

in which
$R^{51}$ is in each case independently a linear or branched alkyl radical having 1 to 6 carbons atoms, preferably methyl, ethyl, isopropyl, tert-butyl, $CF_3$; substituted or unsubstituted aryl radical having 6 to 20 carbon atoms, preferably unsubstituted phenyl or 2,6-dialkylphenyl; substituted or unsubstituted heteroaryl radical having a total of 5 to 18 carbon atoms and/or heteroatoms,
$R^{52}$ is hydrogen, a linear or branched alkyl radical having 1 to 6 carbon atoms, substituted or unsubstituted aryl radical having 6 to 20 carbon atoms, preferably hydrogen;
where the ligand of the formula (B) is, for example, acetylacetonato or hexafluoro-acetylacetonato;
picolinato, salicylato, 8-hydroxyquinolato and
heterocyclic noncarbene ligands of the general formula (III)

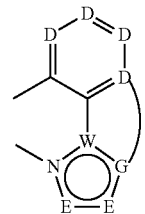

(III)

in which the symbols in the ligand of the general formula (III) are each defined as follows:

D are each independently $CR^{18}$ or N, preferably $CR^{18}$;

W is C, N, preferably C;

E are each independently $CR^{19}$, N, $NR^{20}$, preferably $CR^{19}$ or N;

G is $CR^{21}$, N, $NR^{22}$, S, O, preferably $NR^{21}$ $R^{18}$, $R^{19}$ $R^{21}$ are each independently hydrogen, a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted heterocycloalkyl radical optionally interrupted by at least one heteroatom, optionally bearing at least one functional group and having 3 to 20 carbon atoms and/or heteroatoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or in each case 2 $R^{18}$, $R^{19}$ and $R^{21}$ radicals, together with the carbon atoms to which they are bonded, form a saturated, unsaturated or aromatic, optionally substituted ring optionally interrupted by at least one heteroatom and having a total of 5 to 18 carbon atoms and/or heteroatoms, $R^{20}$, $R^{22}$ are each independently a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted heterocycloalkyl radical optionally interrupted by at least one heteroatom, optionally bearing at least one functional group and having 3 to 20 carbon atoms and/or heteroatoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action; preferably o,o'-dialkylated aryl radical, where the solid curved line is an optional bridge between one of the D groups and the G group; where the bridge may be defined as follows:

alkylene, arylene, heteroarylene, alkynylene, alkenylene, $NR^{23}$, O, S, $SiR^{24}R^{25}$, $CR^{50}$=N and $(CR^{26}R^{27})_d$, where one or more nonadjacent $(CR^{26}R^{27})$ groups may be replaced by $NR^{23}$, O, S, $SiR^{24}R^{25}$, where d is 2 to 10;

and $R^{24}$, $R^{25}$, $R^{26}$, $R^{27}$, $R^{50}$ are each H, alkyl, aryl, heteroaryl, alkenyl, alkynyl;

where—when o in formula (I) is 2, the ligands L may be the same or different.

For the inventive embodiment wherein in each case 2 $R^{18}$, $R^{19}$ and $R^{21}$ radicals, together with the carbon atoms to which they are bonded, form a saturated, unsaturated or aromatic, optionally substituted ring optionally interrupted by at least one heteroatom and having a total of 5 to 18 carbon atoms and/or heteroatoms, for example, two $R^{18}$ radicals, two $R^{19}$ radicals or one $R^{19}$ radical and one $R^{21}$ radical form a corresponding ring.

In the case that the inventive metal-carbene complex of the formula (I) has two ligands L (when M=Ir), the ligands L may each be an identical ligand of the formula (III) or different ligands of the formula (III). It is also possible that one of the ligands L is a ligand of the formula (III) and the second ligand is any ligand L. In a further preferred embodiment, in the case that the inventive metal-carbene complex of the formula (I) has two ligands L, the ligands L are each an identical ligand of the formula (III).

In a further embodiment, m is 0, n is 1 or 2 and o is 1 or 2, where the o ligand(s) L is/are ligand(s) of the general formula (III). If n or o is 2, the particular n azabenzimidazole carbene ligands or o ligands L may be the same or different. In this case, the complexes are heteroleptic metal-carbene complexes which, as well as n azabenzimidazole carbene ligands, have o ligands of the general formula (III). It has been found that the aforementioned metal-carbene complexes of the general formula (I) are especially suitable as emitter material in the light-emitting layer of an OLED.

More preferably, M in the heteroleptic metal-carbene complexes of the formula (I) is Pt, where, in the case that M=Pt, preferably m is 0, n is 1 and o is 1.

Thus, L is preferably selected from the group consisting of carbene ligands of the general formula (II), ligands of the formula (B), more preferably acetylacetonato or hexafluoroacetylacetonato; picolinato, salicylato, 8-hydroxyquinolato and heterocyclic noncarbene ligands of the general formula (III).

Ligands L which are very particularly preferred in accordance with the invention are depicted below:

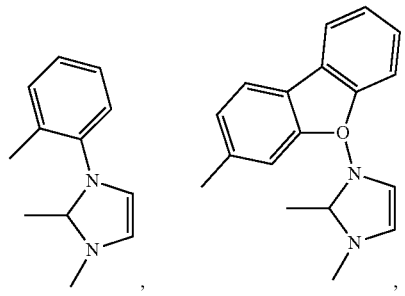

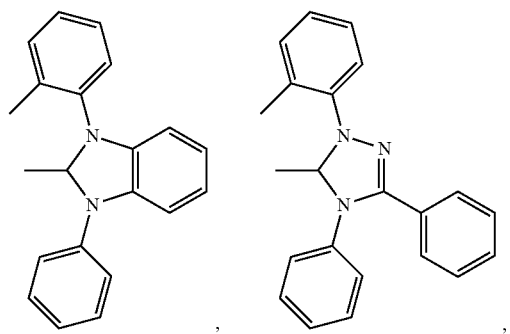

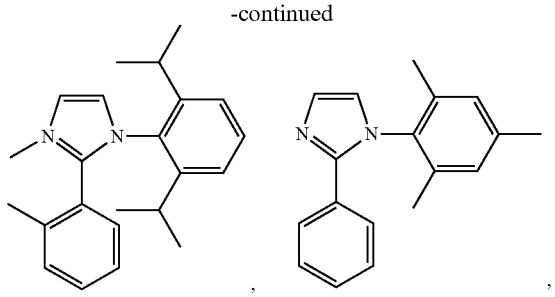
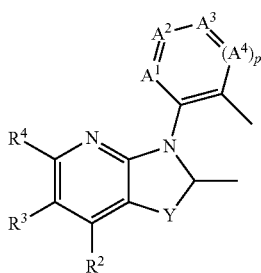

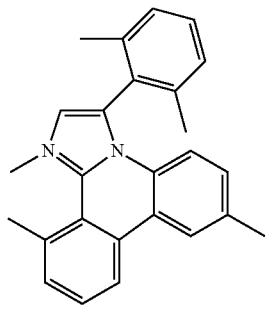

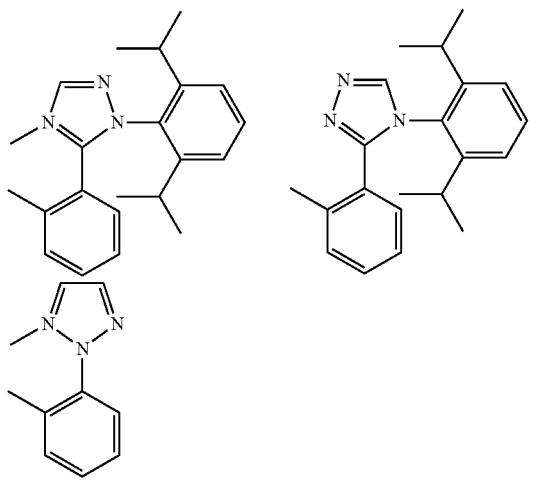

Further preferred ligands L are:

The number o of monoanionic ligands L in the aforementioned case is 0, 1, 2. When o>1, the L ligands may be the same or different, and are preferably the same.

The number m of uncharged ligands K depends on whether the coordination number 6 of the Ir(III) or 4 of the Pt(II) has already been attained with the aid of the carbene ligands and of the ligands L. When—in the case that Ir(III) is used—n is three and three monoanionic bidentate carbene ligands are used, m in the aforementioned case is 0. When—in the case that Pt(II) is used—n is two and two monoanionic bidentate carbene ligands are used, m in this case is likewise 0.

In a preferred embodiment, M, n, Y, $R^2$, $R^3$, $R^4$, $A^1$, $A^2$, $A^3$, $A^4$, p, K, L, n and o in the general formula (I) are each defined as follows:

According to the invention, M is Ir or Pt, preferably Ir. Ir is present in the inventive complexes preferably in the +3 oxidation state (Ir(III)). Pt is present in the inventive complexes in the +2 oxidation state (Pt(II)).

n is generally 1, 2 or 3. If M is Ir(III), n is preferably 3, where all n carbene ligands are more preferably the same (homoleptic carbene complexes). m and o in this case are preferably each 0.

If M is Pt(II), n is preferably 1. In this case, o in formula (I) is preferably likewise 1 and m=0, Suitable ligands L have been specified above, where L in this case is more preferably a ligand of the formula (B).

According to the invention, Y is $NR^1$, O, S or $O(R^{10})_2$, preferably $NR^1$.

In the preferred case that Y is $NR^1$, $R^1$ in a preferred embodiment is a linear or branched alkyl radical having 1 to 6 carbon atoms, substituted or unsubstituted cycloalkyl radical having 5 to 20 carbon atoms, substituted or unsubstituted aryl radical having 6 to 30 carbon atoms, substituted or unsubstituted heteroaryl radical having a total of 5 to 18 carbon atoms and/or heteroatoms.

$R^1$ is more preferably linear or branched alkyl radical having 1 to 6 carbon atoms, substituted or unsubstituted phenyl radical, substituted or unsubstituted heteroaryl radical having a total of 5 or 6 carbon atoms and/or heteroatoms.

$R^1$ is most preferably selected from phenyl, tolyl, mesityl, thiophenyl, furanyl, pyridyl, methyl, isopropyl and neopentyl.

The present invention therefore relates especially to an inventive metal-carbene complex of the formula (I) in which Y is $NR^1$ where $R^1$ is selected from the group consisting of phenyl, tolyl, mesityl, thiophenyl, furanyl, pyridyl, methyl, isopropyl and neopentyl.

In a preferred embodiment, $R^2$, $R^3$, $R^4$ are each independently hydrogen, a linear or branched alkyl radical having 1 to 20 carbon atoms, a substituted or unsubstituted cycloalkyl radical having 5 to 20 carbon atoms, a substituted or unsubstituted aryl radical having 6 to 30 carbon atoms, a substituted or unsubstituted heteroaryl radical having 5 to 18 carbon atoms and/or heteroatoms or a group with donor or acceptor action.

In a preferred embodiment, $R^2$, $R^3$, $R^4$ are each independently hydrogen, a linear or branched alkyl radical having 1 to 6 carbon atoms, substituted or unsubstituted aryl radical having 6 to 30 carbon atoms, substituted or unsubstituted heteroaryl radical having a total of 5 to 18 carbon atoms and/or heteroatoms or a group with donor or acceptor action selected from halogen radicals, preferably F, Cl, more preferably F, $CF_3$, CN and $SiMe_3$;

or $R^3$ and $R^4$, together with the carbon atoms to which they are bonded, may form an optionally substituted, unsaturated ring which is optionally interrupted by at least one further heteroatom, has a total of 5 to 18 carbon atoms and/or heteroatoms and may optionally be fused to at least one further optionally substituted unsaturated ring interrupted by at least one further heteroatom and having a total of 5 to 18 carbon atoms and/or heteroatoms.

According to the invention, an unsaturated ring is a mono-, di- or polyunsaturated, preferably monounsaturated, ring.

$R^2$ is more preferably hydrogen.

$R^3$ is more preferably hydrogen or linear or branched alkyl radical having 1 to 20 carbon atoms or optionally substituted, saturated, unsaturated or aromatic ring having a total of 5 to 18 carbon atoms and/or heteroatoms, more preferably branched alkyl radical or o,o'-dialkylated phenyl ring.

$R^4$ is more preferably hydrogen or linear or branched alkyl radical having 1 to 20 carbon atoms or optionally substituted, saturated, unsaturated or aromatic ring having a total of 5 to 18 carbon atoms and/or heteroatoms, more preferably branched alkyl radical or o,o'-dialkylated phenyl ring.

In a further embodiment, $R^3$ and $R^4$ form, together with the carbon atoms to which they are bonded, an optionally substituted, unsaturated ring having a total of 5 to 18 carbon atoms.

p in a preferred embodiment is 1.

In one embodiment, the $A^1$ group is $CR^6$ or N, preferably $CR^6$, the $A^2$ group is $CR^7$ or N, preferably $CR^7$, the $A^3$ group is $CR^8$ or N, preferably $CR^8$, and the $A^4$ group is $CR^9$ or N, preferably $CR^9$. In a further embodiment, 0, 1 or 2 of the $A^1$, $A^2$, $A^3$ or $A^4$ groups are N, more preferably 0 or 1 groups are N, most preferably 0 groups are N.

In a further preferred embodiment, $R^6$, $R^7$, $R^8$, $R^9$ are each independently hydrogen or linear or branched alkyl radical having 1 to 20 carbon atoms, a $C_6$- to C-aryl radical, preferably a phenyl radical or an o,o'-dialkylated phenyl radical or a group with donor or acceptor action, preferably a group with donor or acceptor action selected from halogen radicals, preferably F, Cl, more preferably F, $CF_3$, CN and $SiMe_3$; more preferably hydrogen.

In a further preferred embodiment, $R^6$ and $R^7$ or $R^7$ and $R^8$ or $R^8$ and $R^9$ form, together with the phenyl ring, i.e. $R^6$ and $R^7$ or $R^7$ and $R^8$ or $R^8$ and $R^9$ form, with the carbon atoms to which the radicals are attached, an unsaturated or aromatic, optionally substituted ring which is optionally interrupted by at least one heteroatom, has a total of 5, 6 or 7 carbon atoms and/or heteroatoms and may optionally be fused to at least one further optionally substituted unsaturated ring interrupted by at least one further heteroatom and having a total of 5 to 18 carbon atoms and/or heteroatoms. The two particular radicals more preferably form, together with the phenyl ring, the following heterocycles: dibenzofuran, dibenzothiophene, fluorene, acridane, xanthene, thioxanthene, phenazine or phenoxazine.

$R^{10}$ is, if present, preferably independently in accordance with the invention, a linear or branched alkyl radical having 1 to 20 carbon atoms, a substituted or unsubstituted aryl radical having 6 to 30 carbon atoms, a substituted or unsubstituted heteroaryl radical having 5 to 18 carbon atoms and/or heteroatoms, more preferably a linear alkyl radical or a substituted or unsubstituted phenyl radical;

or the two $R^{10}$ radicals form, together with the carbon atom to which they are bonded, a saturated or unsaturated optionally substituted ring optionally interrupted by at least one heteroatom and having a total of 5 to 18 carbon atoms and/or heteroatoms.

In a particularly preferred embodiment, the present invention relates to an inventive metal-carbene complex where M, n, Y, $R^2$, $R^3$, $R^4$, $A^1$, $A^2$, $A^3$, $A^4$, p, L, m and o are each defined as follows:

M is Ir, n is 1, 2 or 3, preferably 3, the ligand(s)

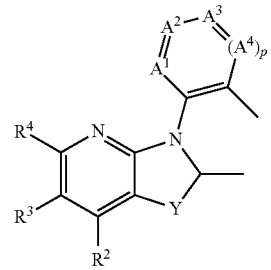

in each case being bidentate ligands; and all n ligands being more preferably the same;

Y is $NR^1$, $R^1$ is a linear or branched alkyl radical having 1 to 6 carbon atoms, substituted or unsubstituted cycloalkyl radical having from 5 to 20 carbon atoms, substituted or unsubstituted aryl radical having 6 to 30 carbon atoms, substituted or unsubstituted heteroaryl radical having a total of 5 to 18 carbon atoms and/or heteroatoms, $R^2$, $R^3$, $R^4$ are independently hydrogen, a linear or branched alkyl radical having 1 to 6 carbon atoms, substituted or unsubstituted aryl radical having 6 to 30 carbon atoms, substituted or unsubstituted heteroaryl radical having a total of 5 to 18 carbon atoms and/or heteroatoms, group with donor or acceptor action selected from halogen radicals, preferably F, Cl, more preferably F; $CF_3$, CN and $SiMe_3$;

or $R^2$ and $R^3$ or $R^3$ and $R^4$, together with the carbon atoms to which they are bonded, form an optionally substituted, unsaturated, saturated or aromatic ring which is optionally interrupted by at least one further heteroatom, has a total of 5 to 18 carbon atoms and/or heteroatoms, and may optionally be fused to at least one further optionally substituted saturated or unsaturated or aromatic ring optionally interrupted by at least one further heteroatom and having a total of 5 to 18 carbon atoms and/or heteroatoms, p is 1;

$A^1$ is $CR^6$;

$A^2$ is $CR^7$;

$A^3$ is $CR^8$;

$A^4$ is $CR^9$;

$R^6$, $R^7$, $R^8$, $R^9$ are each independently hydrogen, a linear or branched alkyl radical optionally interrupted by at least one heteroatom, optionally bearing at least one functional group and having 1 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action selected from halogen radicals, preferably F, Cl, more preferably F; $CF_3$, CN and $SiMe_3$;

or $R^6$ and $R^7$, $R^7$ and $R^8$ or $R^8$ and $R^9$ form, together with the carbon atoms to which they are bonded, a saturated, unsaturated or aromatic, optionally substituted ring which is optionally interrupted by at least one heteroatom, has a total of 5 to 18 carbon atoms and/or heteroatoms and may optionally be fused to at least one further optionally substituted saturated or unsaturated or aromatic ring optionally interrupted by at least one further heteroatom and having a total of 5 to 18 carbon atoms and/or heteroatoms, L is a monoanionic bidentate ligand, preferably selected from the group consisting of carbene ligands of the general formula (II) according to claim 2, a ligand of the formula (B)

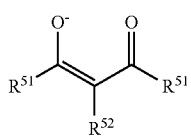

(B)

in which $R^{51}$ is in each case independently a linear or branched alkyl radical having 1 to 6 carbons atoms, preferably methyl, ethyl, isopropyl, tert-butyl, $CF_3$; substituted or unsubstituted aryl radical having 6 to 20 carbon atoms, preferably unsubstituted phenyl or 2,6-dialkylphenyl; substituted or unsubstituted heteroaryl radical having a total of 5 to 18 carbon atoms and/or heteroatoms, $R^{52}$ is hydrogen, a linear or branched alkyl radical having 1 to 6 carbon atoms, substituted or unsubstituted aryl radical having 6 to 20 carbon atoms, preferably hydrogen;

where the ligand of the formula (B) is, for example, acetylacetonato or hexafluoro-acetylacetonato;

picolinato, salicylato, 8-hydroxyquinolato and heterocyclic noncarbene ligands of the general formula (III);

m is 0, o is 0, 1 or 2, preferably 0;

excluding ligands L of the following general formula (A):

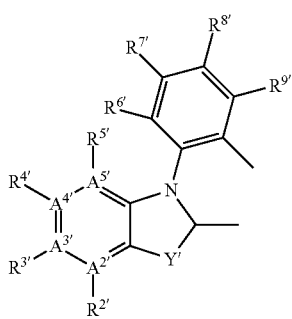

(A)

where Y', $A^{2'}$, $A^{3'}$, $A^{4'}$, $A^{5'}$, $R^{1'}$, $R^{2'}$, $R^{3'}$, $R^{4'}$, $R^{5'}$, $R^{6'}$, $R^{7'}$, $R^{8'}$, $R^{9'}$ and $R^{10'}$ are each defined as follows:

Y' is $NR^{1'}$, O, S or $C(R^{10'})_2$, $A^{2'}$, $A^{3'}$, $A^{4'}$, $A^{5'}$ are each independently N or C, where 2 A'=nitrogen atoms and at least one carbon atom is present between two nitrogen atoms in the ring, $R^{1'}$ is a linear or branched alkyl radical optionally bearing at least one functional group, optionally interrupted by at least one heteroatom and having 1 to 20 carbon atoms, cycloalkyl radical having 3 to 20 carbon atoms, substituted or unsubstituted aryl radical having 6 to 30 carbon atoms, substituted or unsubstituted heteroaryl radical having a total of 5 to 18 carbon atoms and/or heteroatoms, $R^{2'}$, $R^{3'}$, $R^{4'}$, $R^{5'}$, if $A^{2'}$, $A^{3'}$, $A^{4'}$ and/or $A^{5'}$ is N, are each a free electron pair or, if $A^{2'}$, $A^{3'}$, $A^{4'}$ and/or $A^{5'}$ is C, are each independently hydrogen, a linear or branched alkyl radical optionally bearing at least one functional group, optionally interrupted by at least one heteroatom and having 1 to 20 carbon atoms, cycloalkyl radical having 3 to 20 carbon atoms, substituted or unsubstituted aryl radical having 6 to 30 carbon atoms, substituted or unsubstituted heteroaryl radical having a total of 5 to 18 carbon atoms and/or heteroatoms, group with donor or acceptor action or $R^{3'}$ and $R^{4'}$ form, together with $A^{3'}$ and $A^{4'}$, an optionally substituted, unsaturated ring optionally interrupted by at least one further heteroatom and having a total of 5 to 18 carbon atoms and/or heteroatoms, $R^{6'}$, $R^{7'}$, $R^{8'}$, $R^{9'}$ are each independently hydrogen, a linear or branched alkyl radical optionally bearing at least one functional group, optionally interrupted by at least one heteroatom and having 1 to 20 carbon atoms, cycloalkyl radical having 3 to 20 carbon atoms, cycloheteroalkyl radical having 3 to 20 carbon atoms, substituted or unsubstituted aryl radical having 6 to 30 carbon atoms, substituted or unsubstituted heteroaryl radical having a total of 5 to 18 carbon atoms and/or heteroatoms, group with donor or acceptor action, or $R^{6'}$ and $R^{7'}$, $R^{7'}$ and $R^{8'}$ or $R^{8'}$ and $R^{9'}$, together with the carbon atoms to which they are bonded, form a saturated, unsaturated or aromatic, optionally substituted ring optionally interrupted by at least one heteroatom and having a total of 5 to 18 carbon atoms and/or heteroatoms, and/or if $A^5$ is C, $R^5$ and $R^{6'}$ together form a saturated or unsaturated, linear or branched bridge optionally comprising heteroatoms, aromatic unit, heteroaromatic unit and/or functional groups and having a total of 1 to 30 carbon atoms and/or heteroatoms, to which is optionally fused a substituted or unsubstituted, five- to eight-membered ring comprising carbon atoms and/or heteroatoms, $R^{10'}$ is independently a linear or branched alkyl radical optionally bearing at least one functional group, optionally interrupted by at least one heteroatom and having 1 to 20 carbon atoms, cycloalkyl radical having 3 to 20 carbon atoms, substituted or unsubstituted aryl radical having 6 to 30 carbon atoms, substituted or unsubstituted heteroaryl radical having a total of 5 to 18 carbon atoms and/or heteroatoms.

Carbene ligands of the general formula (II) and heterocyclic noncarbene ligands of the general formula (III) have been defined above.

The present invention more preferably relates to an inventive metal-carbene complex where M, n, Y, $R^2$, $R^3$, $R^4$, A1, $A^2$, $A3^7$, $A^{48}$, p, L, m and o are each defined as follows:

M is Ir, n is 3, where the ligand(s)

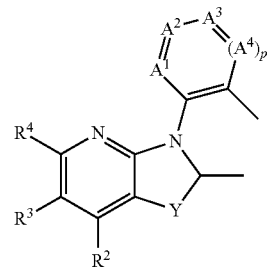

are each bidentate ligands, and where all n ligands are more preferably the same;

Y is NR$^1$,

R$^1$ is a linear or branched alkyl radical having 1 to 6 carbon atoms, substituted or unsubstituted cycloalkyl radical having 5 to 20 carbon atoms, substituted or unsubstituted aryl radical having 6 to 30 carbon atoms, substituted or unsubstituted heteroaryl radical having a total of 5 to 18 carbon atoms and/or heteroatoms,

R$^2$, R$^3$,

R$^4$ are each independently hydrogen, a linear or branched alkyl radical having 1 to 6 carbon atoms, substituted or unsubstituted aryl radical having 6 to 30 carbon atoms, especially o,o'-dialkylated or unsubstituted phenyl radical, substituted or unsubstituted heteroaryl radical having a total of 5 to 18 carbon atoms and/or heteroatoms, group with donor or acceptor action selected from halogen radicals, preferably F, Cl, more preferably F; CF$_3$, CN and SiMe$_3$;

or

R$^2$ and R$^3$ or R$^3$ and R$^4$ form, together with the carbon atoms to which they are bonded, an optionally substituted unsaturated, saturated or aromatic ring which is optionally interrupted by at least one further heteroatom, has a total of 5 to 7 carbon atoms and/or heteroatoms and may optionally be fused to at least one further optionally substituted saturated or unsaturated or aromatic ring optionally interrupted by at least one further heteroatom and having a total of 5 to 7 carbon atoms and/or heteroatoms, p is 1;

A$^1$ is CR$^6$;

A$^2$ is CR$^7$;

A$^3$ is CR$^8$;

A$^4$ is CR$^9$;

R$^6$, R$^7$,

R$^8$, R$^9$ are each independently hydrogen, a linear or branched alkyl radical having 1 to 20 carbon atoms, aryl radical having 6 to 30 carbon atoms, group with donor or acceptor action selected from halogen radicals, preferably F, Cl, more preferably F; CF$_3$, CN and SiMe$_3$;

or

R$^6$ and R$^7$,

R$^7$ and R$^8$ or

R$^8$ and R$^9$ form, together with the carbon atoms to which they are bonded, an aromatic, optionally substituted ring which is optionally interrupted by one nitrogen or oxygen atom, has a total of 5 to 18 carbon atoms and/or heteroatoms and may optionally be fused to at least one further optionally substituted aromatic ring optionally interrupted by one nitrogen or oxygen atom and having a total of 5 to 18 carbon atoms and/or heteroatoms, L is a monoanionic bidentate ligand, selected from the group consisting of carbene ligands of the general formula (II), a ligand of the formula (B)

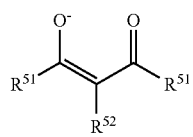
(B)

in which

R$^{51}$ is in each case independently a linear or branched alkyl radical having 1 to 6 carbons atoms, preferably methyl, ethyl, isopropyl, tert-butyl, CF$_3$; substituted or unsubstituted aryl radical having 6 to 20 carbon atoms, preferably unsubstituted phenyl or 2,6-dialkylphenyl; substituted or unsubstituted heteroaryl radical having a total of 5 to 18 carbon atoms and/or heteroatoms, R$^{52}$ is hydrogen, a linear or branched alkyl radical having 1 to 6 carbon atoms, substituted or unsubstituted aryl radical having 6 to 20 carbon atoms, preferably hydrogen;

where the ligand of the formula (B) is, for example, acetylacetonato or hexafluoro-acetylacetonato;

picolinato, salicylato, 8-hydroxyquinolato and heterocyclic noncarbene ligands of the general formula (III);

m is 0, o is 0, 1 or 2.

The further abovementioned preferred and particularly preferred embodiments apply correspondingly.

Very particularly preferred inventive metal-carbene complexes of the general formula (I) are shown below.

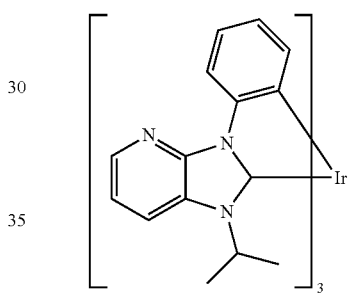

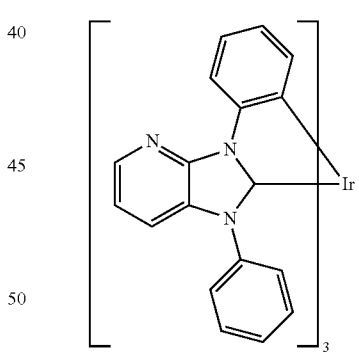

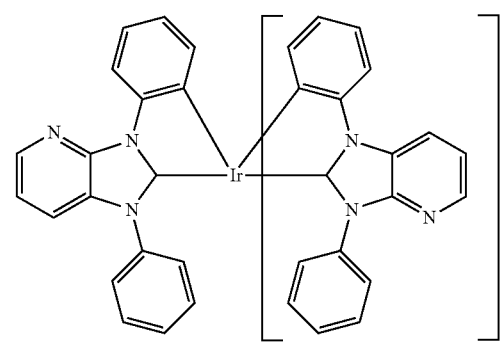

25
-continued
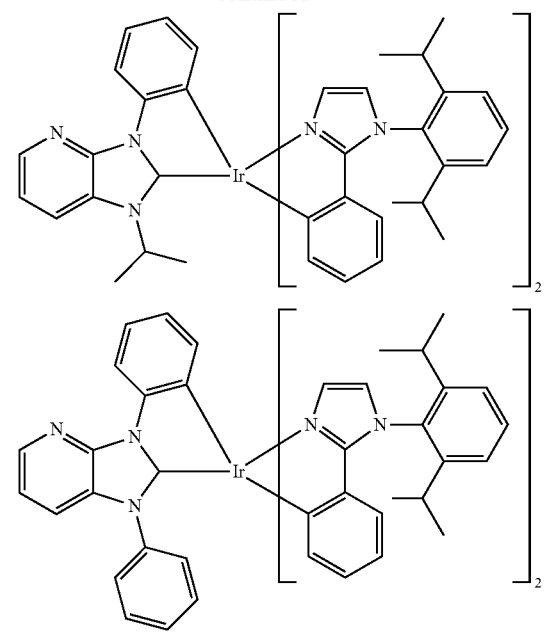
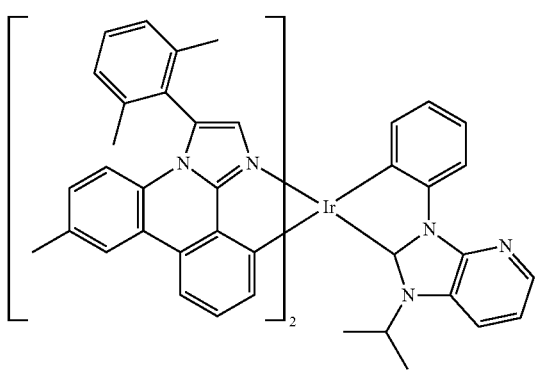
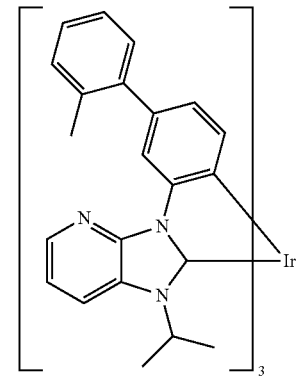
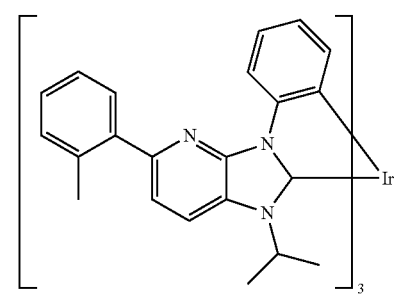
26
-continued
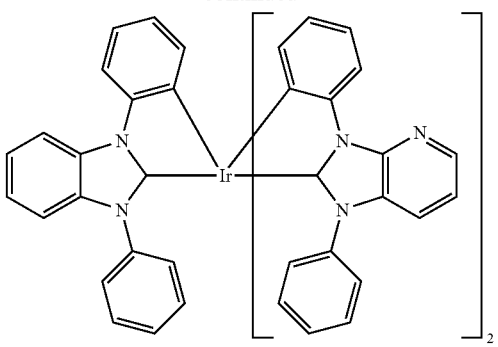
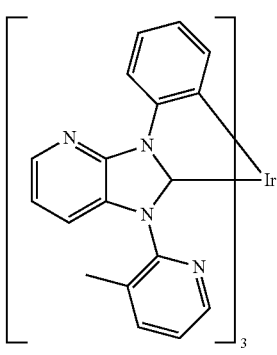
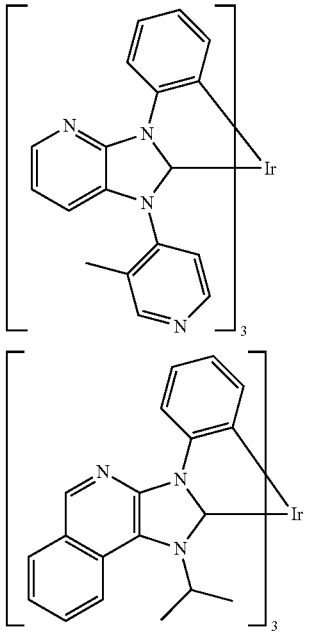
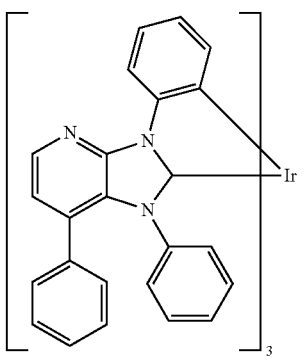

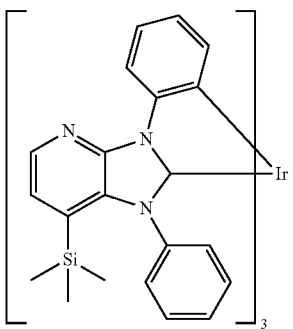
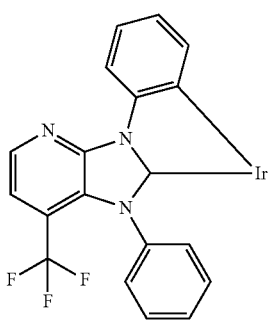
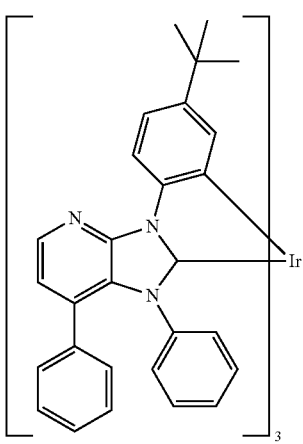
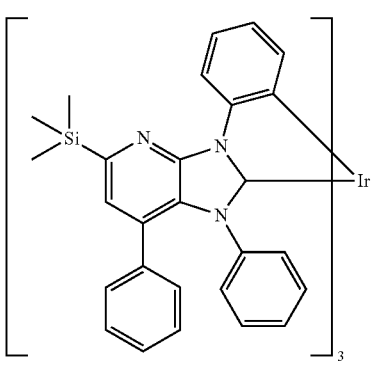
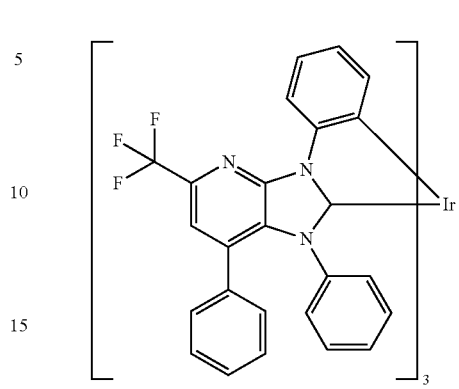
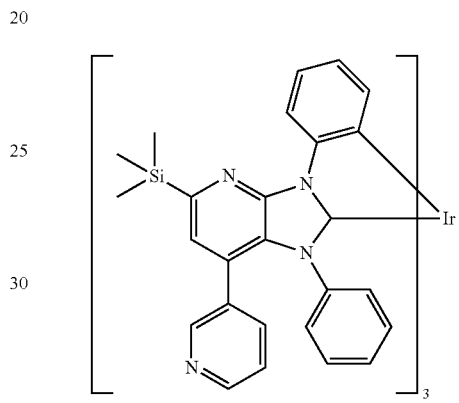
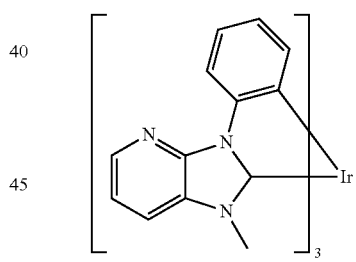
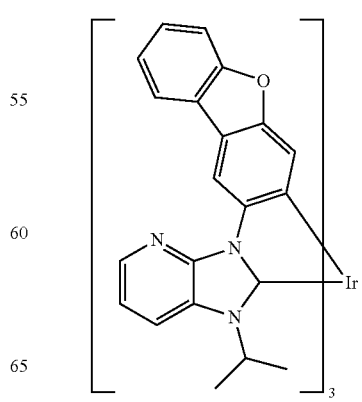

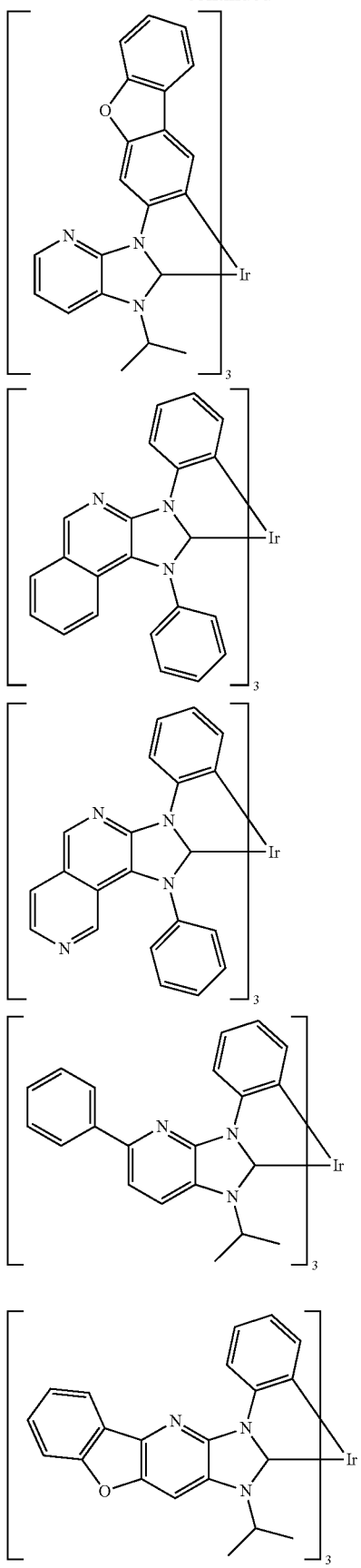

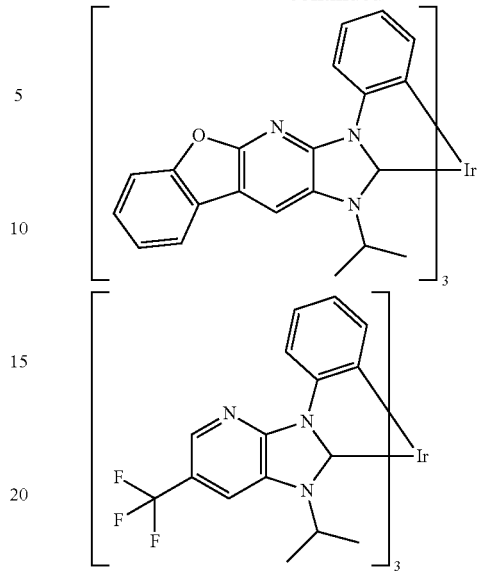

The inventive homoleptic metal-carbene complexes may be present in the form of facial or meridional isomers.

Especially in the case of the preferred homoleptic metal-carbene complexes (n=3 where all n carbene ligands are the same) of the general formula (I), the facial isomers can preferably be used as matrix material in the light-emitting layer of an OLED or as charge blockers, and the meridional isomers can preferably be used as emitter materials in OLEDs.

A particularly preferred embodiment of the present application therefore relates to an OLED comprising at least one homoleptic metal-carbene complex of the general formula (I) as emitter material, the homoleptic metal-carbene complex of the formula (I) preferably being used in the form of the meridional isomer thereof. In principle, however, mixtures of facial and meridional isomers of the formula (I) or facial isomers of the formula (I) are suitable as emitter material in OLEDs.

In the case of the heteroleptic metal-carbene complexes, four different isomers may be present. The heteroleptic complexes are preferably used as emitter materials and/or charge transport material.

The present invention additionally also relates to a process for preparing the inventive metal-carbene complexes by contacting suitable compounds comprising M with the appropriate ligands or ligand precursors.

In a preferred embodiment of the process according to the invention, a suitable compound comprising the appropriate metal M, i.e. iridium or platinum, preferably iridium, and appropriate carbene ligands, preferably in deprotonated form as the free carbene or in the form of a protected carbene, for example as the silver-carbene complex, are contacted. Suitable precursor compounds comprise the appropriate substituents $R^1$ to $R^4$ and $R^6$ to $R^9$ and $R^{10}$ which should be present in the complexes of the general formula (I).

The present invention therefore relates more particularly to the process according to the invention wherein the ligand precursor used is a corresponding Ag-carbene complex.

In a further preferred embodiment of the process according to the invention, the ligand precursors used are organic compounds which are reacted with suitable M-comprising compounds. The carbene can be released from precursors of the carbene ligands by removing volatile substances, for example lower alcohols such as methanol, ethanol, for example at elevated temperature and/or under reduced pressure and/or using molecular sieves which bind the alcohol molecules eliminated.

The present invention also relates to a process according to the invention for preparing the metal-carbene complexes of the general formula (I) by contacting suitable M-comprising compounds with compounds of the general formula (IV) or (V)

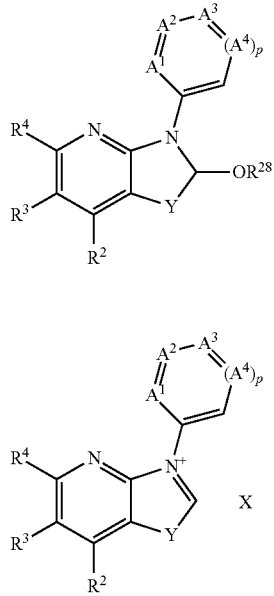

where Y, $R^2$, $R^3$, $R^4$, $A^1$, $A^2$, $A^3$, $A^4$ and p are each as already defined for the compounds of the general formula (I), and $R^{28}$ or X are defined as follows:

$R^{28}$ is independently $SiR^{29}R^{30}R^{31}$, aryl, heteroaryl, alkyl, cycloalkyl or heterocycloalkyl, X is F, Cl, Br, I, $PF_6$, $BF_4$, $R^{29}$, $R^{30}$, $R^{31}$ are each independently aryl, heteroaryl, alkyl, cycloalkyl or heterocycloalkyl.

The definitions of aryl, heteroaryl, alkyl, cycloalkyl and heterocycloalkyl have been specified above.

In a particularly preferred embodiment, $R^{28}$ is alkyl, especially $C_1$-$C_{20}$-alkyl, preferably $C_1$-$C_{10}$-alkyl, more preferably $C_1$-$C_8$-alkyl, for example methyl, ethyl, propyl such as n-propyl, isopropyl, butyl such as n-butyl, isobutyl, tert-butyl, pentyl, hexyl, heptyl or octyl.

$R^{28}$ in the compound of the general formula (IV) is most preferably methyl or ethyl.

Compounds of the general formulae (IV) and (V) are generally obtainable by processes known to those skilled in the art.

In the case, which is particularly preferred in accordance with the invention, that Y is $NR^1$, $A^1$ is $R^6$, $A^2$ is $R^7$, $A^3$ is $R^8$, $A^4$ is $R^9$ and p is 1, for example, corresponding compounds of the general formula (IV) can be obtained by reacting compounds of the general formula (V')

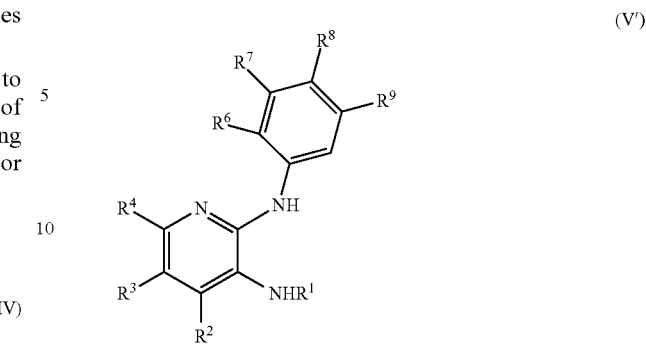

with compounds of the general formula (VI)

$$HC(OR^{28})_3 \quad (VI),$$

where $R^2$, $R^3$, $R^4$, $R^6$, $R^7$, $R^8$, $R^9$ and $R^{28}$ are each as already defined above for the compounds of the general formula (I) or (IV).

This preparation of the compounds of the general formula (IV) can be effected in the presence or in the absence of a solvent. Suitable solvents are specified below. In a preferred embodiment, the compounds of the general formula (IV) are prepared in substance, or the compound of the general formula (VI) is added in an excess, such that it functions as a solvent.

Compounds of the general formulae (V') and (VI) are commercially available and/or obtainable by processes known to those skilled in the art; for example, compounds of the general formula (V') are obtainable by reacting the appropriate chlorides with the appropriate amines.

The compounds of the general formula (IV) are prepared generally at a temperature of 10 to 150° C., preferably 40 to 120° C., more preferably 60 to 110° C.

The reaction time is generally 2 to 48 hours, preferably 6 to 24 hours, more preferably 8 to 16 hours.

After the reaction has ended, the desired product can be isolated and purified by customary processes known to those skilled in the art, for example filtration, recrystallization, column chromatography, etc.

Appropriate compounds, especially complexes, comprising the appropriate metal M, preferably iridium, are known to those skilled in the art. Particularly suitable compounds comprising platinum or iridium comprise, for example, ligands such as halides, preferably chloride, 1,5-cyclooctadiene (COD), cyclooctene (COE), phosphines, cyanides, alkoxides, pseudohalides and/or alkyl.

Particularly preferred complexes comprising the appropriate metal, especially iridium, are selected from the group consisting of $[Ir(COD)Cl]_2$, $[Ir(COE)_2Cl]_2$ $IrCl_3 \times H_2O$, $Ir(acac)_3$, $Ir(COD)_2BF_4$, $Ir(COD)_2BARF$ (BARF=tetrakis[3,5-bis(trifluoromethyl)phenyl]borate)), $Pt(COD)Cl_2$, $Pt(acac)_2$, $[Pt(C_6H_{10})Cl_2]_2$, $K_2PtCl_6$ and mixtures thereof.

The carbene ligand precursors are deprotonated, preferably before the reaction, for example, by basic compounds known to those skilled in the art, for example basic metalates, basic metal acetates, acetylacetonates or alkoxides, or bases such as $KO^tBu$, $NaO^tBu$, $LiO^tBu$, NaH, silylamides, $Ag_2O$ and phosphazene bases. Particular preference is given to deprotonating with $Ag_2O$ to obtain the corresponding Ag-carbene, which is reacted with the compound comprising M to give the inventive complexes.

The process according to the invention for preparing the complexes of the general formula (I) using the compounds of the general formulae (IV) or (V) has the advantage that the compounds of the general formulae (IV) and (V) are stable intermediates which can be handled readily and can be isolated under standard laboratory conditions. In addition, the compounds of the general formulae (IV) and (V) are soluble in customary organic solvents, such that the preparation of the inventive complexes of the general formula (I) in homogeneous solution is possible, such that a workup of the desired product, i.e. of the complexes of the general formula (I) is more readily possible, for example for isolation and/or purification.

The contacting is preferably effected in a solvent. Suitable solvents are known per se to those skilled in the art and are preferably selected from the group consisting of aromatic or aliphatic solvents, for example benzene, toluene, xylene or mesitylene, cyclic or acyclic ethers, for example dioxane or THF, alcohols, esters, amides, ketones, nitriles, halogenated compounds and mixtures thereof. Particularly preferred solvents are toluene, xylenes, mesitylene and dioxane.

The molar ratio of metal-noncarbene complex used to carbene ligand precursor used is generally 1:10 to 10:1, preferably 1:1 to 1:6, more preferably 1:2 to 1:5.

The contacting is generally effected at a temperature of 20 to 200° C., preferably 50 to 150° C., more preferably 60 to 130° C.

The reaction time depends on the desired carbene complex and is generally 0.02 to 50 hours, preferably 0.1 to 24 hours, more preferably 1 to 12 hours.

The complexes of the general formula (I) obtained after the reaction can optionally be purified by processes known to those skilled in the art, for example washing, crystallization or chromatography, and optionally isomerized under conditions likewise known to those skilled in the art, for example with acid mediation, thermally or photochemically.

The inventive metal-carbene complexes of the formula (I) can be used in electronic components, for example organic electronic components selected from switching elements such as organic light-emitting diodes (OLEDs), organic photovoltaic cells (OPVs), organic field-effect transistors (OFETs) and light-emitting electrochemical cells (LEECs), preference being given to using the metal-carbene complexes of the formula (I) in OLEDs.

In a preferred embodiment, the organic electronic component is an OLED comprising a light-emitting layer comprising at least one inventive metal-carbene complex of the formula (I).

The aforementioned metal-carbene complexes of the formula (I) and mixtures thereof are outstandingly suitable as emitter molecules in organic light-emitting diodes (OLEDs). Variations in the ligands make it possible to provide corresponding complexes which exhibit electroluminescence in the red, green and especially in the blue region of the electromagnetic spectrum. The inventive metal-carbene complexes of the general formula (I) are therefore outstandingly suitable as emitter substances, since they have emission (electroluminescence) in the visible region of the electromagnetic spectrum, for example at 400 to 800 nm, preferably 400 to 600 nm. The inventive complexes make it possible to provide compounds which have electroluminescence in the red, green and in the blue region of the electromagnetic spectrum. It is thus possible, with the aid of the inventive complexes as emitter substances, to provide industrially usable OLEDs.

In addition, the inventive metal-carbene complexes of the general formula (I) can be used as matrix material, charge transport material, especially hole transport material, and/or charge blocker.

The inventive metal-carbene complexes of the general formula (I) are preferably used as an emitter and/or charge transport material and/or matrix material, more preferably as an emitter.

Particular properties of the inventive metal-carbene complexes of the general formula (I) are particularly good efficiencies, good CIE color loci and long lifetimes when used in OLEDs.

The present application therefore further provides an OLED comprising at least one inventive metal-carbene complex of the general formula (I). The inventive metal-carbene complex of the general formula (I) is used in the OLED preferably as an emitter, matrix material, charge transport material, especially hole transport material, and/or charge blocker, more preferably as an emitter and/or hole transport material, most preferably as an emitter.

The present application also provides for the use of the metal-carbene complexes of the general formula (I) in OLEDs, preferably as an emitter, matrix material, charge transport material, especially hole transport material, and/or charge blocker, more preferably as an emitter and/or hole transport material, most preferably as an emitter.

Organic light diodes are in principle formed from a plurality of layers, e.g.:
anode (1)
hole-transporting layer (2)
light-emitting layer (3)
electron-transporting layer (4)
cathode (5)

It is, however, also possible that the OLED does not have all of the layers mentioned; for example, an OLED comprising layers (1) (anode), (3) (light-emitting layer) and (5) (cathode) is likewise suitable, in which case the functions of layers (2) (hole-transporting layer) and (4) (electron-transporting layer) are assumed by the adjoining layers. OLEDs having layers (1), (2), (3) and (5) or layers (1), (3), (4) and (5) are likewise suitable.

The metal-carbene complexes of the general formula (I) are preferably used as emitter molecules and/or matrix materials in the light-emitting layer (3). The inventive metal-carbene complexes of the general formula (I) may also—in addition to use as emitter molecules and/or matrix materials in the light-emitting layer (3) or instead of use in the light-emitting layer—also be used as a charge transport material in the hole-transporting layer (2) or in the electron-transporting layer (4) and/or as a charge blocker, preference being given to use as a charge transport material in the hole-transporting layer (2) (hole transport material).

The present application therefore further provides a light-emitting layer comprising at least one of the inventive metal-carbene complexes of the general formula (I), preferably as emitter material and/or matrix material, more preferably as emitter material. Preferred metal-carbene complexes of the general formula (I) have already been specified above.

In a further embodiment, the present invention relates to a light-emitting layer consisting of at least one inventive metal-carbene complex of the general formula (I).

The metal-carbene complexes of the general formula (I) used in accordance with the invention may be present in the light-emitting layer in substance, i.e. without further additions. However, it is also possible that, in addition to the metal-carbene complexes of the general formula (I) used in accordance with the invention, further compounds are present in the light-emitting layer. In addition, a diluent material (matrix material) may be used. This diluent material may be a polymer, for example poly(N-vinylcarbazole) or polysilane. The diluent material may, however, likewise be a small molecule, for example 4,4'-N,N'-dicarbazolebiphenyl (CDP) or tertiary aromatic amines. When a diluent material is used, the proportion of the inventive metal-carbene complexes of the general formula (I) in the light-emitting layer is generally less than 40% by weight, preferably 3 to 30% by weight. The inventive metal-carbene complexes of the general formula (I) are preferably used in a matrix. The light-emitting layer thus preferably comprises at least one inventive metal-carbene complex of the general formula (I) and at least one matrix material.

Suitable matrix materials are—in addition to the aforementioned dilution materials—in principle the materials specified hereinafter as hole and electron transport materials, and also carbon complexes, for example the carbene complexes of the formula (I) or the carbene complexes mentioned in WO 2005/019373. Particularly suitable are carbazole derivatives, for example 4,4'-bis(carbazol-9-yl)-2,2'-dimethylbiphenyl (CDBP), 4,4'-bis(carbazol-9-yl)biphenyl (CBP), 1,3-bis(N-carbazolyl)benzene (mCP), and the matrix materials specified in the following applications: WO2008/034758, WO2009/003919.

Further suitable matrix materials, which may be small molecules or (co)polymers of the small molecules mentioned, are specified in the following publications: WO2007108459 (H-1 to H-37), preferably H-20 to H-22 and H-32 to H-37, most preferably H-20, H-32, H-36, H-37, WO2008035571 A1 (Host 1 to Host 6), JP2010135467 (compounds 1 to 46 and Host-1 to Host-39 and Host-43), WO2009008100 compounds No. 1 to No. 67, preferably No. 3, No. 4, No. 7 to No. 12, No. 55, No. 59, No. 63 to No. 67, more preferably No. 4, No. 8 to No. 12, No. 55, No. 59, No. 64, No. 65, and No. 67, WO2009008099 compounds No. 1 to No. 110, WO2008140114 compounds 1-1 to 1-50, WO2008090912 compounds OC-7 to OC-36 and the polymers of Mo-42 to Mo-51, JP2008084913 H-1 to H-70, WO2007077810 compounds 1 to 44, preferably 1, 2, 4-6, 8, 19-22, 26, 28-30, 32, 36, 39-44, WO201001830 the polymers of monomers 1-1 to 1-9, preferably of 1-3, 1-7, and 1-9, WO2008029729 the (polymers of) compounds 1-1 to 1-36, WO20100443342 HS-1 to HS-101 and BH-1 to BH-17, preferably BH-1 to BH-17, JP2009182298 the (co)polymers based on the monomers 1 to 75, JP2009170764, JP2009135183 the (co)polymers based on the monomers 1-14, WO2009063757 preferably the (co) polymers based on the monomers 1-1 to 1-26, WO2008146838 the compounds a-1 to a-43 and 1-1 to 1-46, JP2008207520 the (co)polymers based on the monomers 1-1 to 1-26, JP2008066569 the (co)polymers based on the monomers 1-1 to 1-16, WO2008029652 the (co) polymers based on the monomers 1-1 to 1-52, WO2007114244 the (co)polymers based on the monomers 1-1 to 1-18, JP2010040830 the compounds HA-1 to HA-20, HB-1 to HB-16, HC-1 to HC-23 and the (co) polymers based on the monomers HD-1 to HD-12, JP2009021336, WO2010090077 the compounds 1 to 55, WO2010079678 the compounds H1 to H42, WO2010067746, WO2010044342 the compounds HS-1 to HS-101 and Poly-1 to Poly-4, JP2010114180 the compounds PH-1 to PH-36, US2009284138 the compounds 1 to 111 and H1 to H71, WO2008072596 the compounds 1 to 45, JP2010021336 the compounds H-1 to H-38, preferably H-1, WO2010004877 the compounds H-1 to H-60, JP2009267255 the compounds 1-1 to 1-105, WO2009104488 the compounds 1-1 to 1-38, WO2009086028, US2009153034, US2009134784, WO2009084413 the compounds 2-1 to 2-56, JP2009114369 the compounds 2-1 to 2-40, JP2009114370 the compounds 1 to 67, WO2009060742 the compounds 2-1 to 2-56, WO2009060757 the compounds 1-1 to 1-76, WO2009060780 the compounds 1-1 to 1-70, WO2009060779 the compounds 1-1 to 1-42, WO2008156105 the compounds 1 to 54, JP2009059767 the compounds 1 to 20, JP2008074939 the compounds 1 to 256, JP2008021687 the compounds 1 to 50, WO2007119816 the compounds 1 to 37, WO2010087222 the compounds H-1 to H-31, WO2010095564 the compounds HOST-1 to HOST-61, WO2007108362, WO2009003898, WO2009003919, WO2010040777, US2007224446 and WO06128800.

In a particularly preferred embodiment, one or more compounds of the general formula (X) specified hereinafter are used as matrix material. Preferred embodiments of the compounds of the general formula (X) are likewise specified hereinafter.

The individual layers among the aforementioned layers of the OLED may in turn be formed from two or more layers. For example, the hole-transporting layer may be formed from one layer, into which holes are injected from the electrode, and a layer which transports the holes away from the hole-injecting layer into the light-emitting layer. The electron-transporting layer may likewise consist of a plurality of layers, for example of a layer in which electrons are injected through the electrode and a layer which receives electrons from the electron-injecting layer and transports them into the light-emitting layer. These layers mentioned are each selected according to factors such as energy level, thermal resistance and charge carrier mobility, and also energy difference of the layers mentioned with the organic layers or the metal electrodes. The person skilled in the art is capable of selecting the construction of the OLEDs such that it is matched optimally to the heteroleptic complexes according to the present invention used as emitter substances in accordance with the invention.

In order to obtain particularly efficient OLEDs, the HOMO (highest occupied molecular orbital) of the hole-transporting layer should be aligned to the work function of the anode, and the LUMO (lowest unoccupied molecular orbital) of the electron-transporting layer should be aligned to the work function of the cathode.

The present application further provides an OLED comprising at least one inventive light-emitting layer. The further layers in the OLED may be formed from any material which is typically used in such layers and is known to those skilled in the art.

Suitable materials for the aforementioned layers (anode, cathode, hole and electron injection materials, hole and electron transport materials and hole and electron blocker materials, matrix materials, fluorescence and phosphorescence emitters) are known to those skilled in the art and are specified, for example, in H. Meng, N. Herron, *Organic Small Molecule Materials for Organic Light-Emitting Devices* in *Organic Light-Emitting Materials and Devices*, eds: Z. Li, H. Meng, Taylor & Francis, 2007, Chapter 3, pages 295 to 411.

The anode is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (1) comprises an organic material, for example polyaniline, as described, for example, in Nature, Vol. 357, pages 477 to 479 (Jun. 11, 1992). At least either the anode or the cathode should be at least partly transparent in order to be able to emit the light formed.

Suitable hole transport materials for layer (2) of the inventive OLED are disclosed, for example, in Kirk-Othmer Encyclopedia of Chemical Technology, 4th Edition, Vol. 18, pages 837 to 860, 1996. Either hole-transporting molecules or polymers may be used as the hole transport material. Customarily used hole-transporting molecules are selected from the group consisting of 4,4'-bis[N-(1-naphthyl)-N-phenylamino]biphenyl (α-NPD), N,N'-diphenyl-N,N'-bis(3-methylphenyl)-[1,1'-biphenyl]-4,4'-diamine (TPD), 1,1-bis[di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)-cyclobutane (DCZB), N,N,N',N'-tetrakis(4-methylphenyl)-(1,1'-biphenyl)-4,4'-diamine (TTB), fluorine compounds such as 2,2',7,7'-tetra(N,N-di-tolyl)amino-9,9-spirobifluorene (spiro-TTB), N,N'-bis(naphthalen-1-yl)-N,N'-bis(phenyl)-9,9-spirobifluorene (spiro-NPB) and 9,9-bis(4-(N,N-bis-biphenyl-4-yl-amino)phenyl-9H-fluorene, benzidine compounds such as N,N'-bis(naphthalen-1-yl)-N,N'-bis(phenyl)benzidine and porphyrin compounds such as copper phthalocyanines. Customarily used hole-transporting polymers are selected from the group consisting of polyvinylcarbazoles, (phenylmethyl)polysilanes and polyanilines. It is likewise possible to obtain hole-transporting polymers by doping hole-transporting molecules into polymers such as polystyrene and polycarbonate. Suitable hole-transporting molecules are the molecules already mentioned above.

In addition—in one embodiment—it is possible to use carbene complexes as hole conductor materials, in which case the band gap of the at least one hole conductor material is generally greater than the band gap of the emitter material used. In the context of the present application, band gap is understood to mean the triplet energy. Suitable carbene complexes are, for example, the inventive carbine complexes of the general formula (I), carbene complexes as described in WO 2005/019373 A2, WO 2006/056418 A2, WO 2005/113704, WO 2007/115970, WO 2007/115981 and WO 2008/000727. One example of a suitable carbene complex is Ir(D-PBIC)$_3$ with the formula:

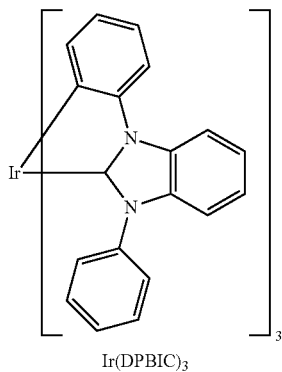

Ir(DPBIC)$_3$

The hole-transporting layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example it is possible to use mixtures in the hole-transporting layer, in particular mixtures which lead to electrical p-doping of the hole-transporting layer. p-Doping is achieved by the addition of oxidizing materials. These mixtures may, for example, be the following mixtures: mixtures of the abovementioned hole transport materials with at least one metal oxide, for example $MoO_2$, $MoO_3$, $WO_x$, $ReO_3$ and/or $V_2O_5$, preferably $MoO_3$ and/or $ReO_3$, more preferably $ReO_3$ or mixtures comprising the aforementioned hole transport materials and one or more compounds selected from 7,7,8,8-tetracyanoquinodimethane (TCNQ), 2,3,5,6-tetrafluoro-7,7,8,8-tetracyanoquinodimethane ($F_4$-TCNQ), 2,5-bis(2-hydroxyethoxy)-7,7,8,8-tetracyanoquinodimethane, bis(tetra-n-butylammonium)tetracyanodipheno-quinodimethane, 2,5-dimethyl-7,7,8,8-tetracyanoquinodimethane, tetracyanoethylene, 11,11,12,12-tetracyanonaphtho-2,6-quinodimethane, 2-fluoro-7,7,8,8-tetracyanoquino-dimethane, 2,5-difluoro-7,7,8,8-tetracyanoquinodimethane, dicyanomethylene-1,3,4,5,7,8-hexafluoro-6H-naphthalen-2-ylidene)malononitrile ($F_6$-TNAP), Mo(tfd)$_3$ (from Kahn et al., J. Am. Chem. Soc. 2009, 131 (35), 12530-12531), compounds as described in EP1988587 and in EP2180029 and quinone compounds as mentioned in EP 09153776.1.

Suitable electron-transporting materials for layer (4) of the inventive OLEDs comprise metals chelated with oxinoid compounds, such as tris(8-hydroxyquinolato)aluminum (Alq$_3$), compounds based on phenanthroline such as 2,9-dimethyl-4,7-diphenyl-1,10-phenanthroline (DDPA=BCP), 4,7-diphenyl-1,10-phenanthroline (Bphen), 2,4,7,9-tetraphenyl-1,10-phenanthroline, 4,7-diphenyl-1,10-phenanthroline (DPA) or phenanthroline derivatives disclosed in EP1786050, in EP1970371, or in EP1097981, and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). Layer (4) may serve both to ease the electron transport and as a buffer layer or as a barrier layer in order to prevent quenching of the exciton at the interfaces of the layers of the OLED. Layer (4) preferably improves the mobility of the electrons and reduces quenching of the exciton.

It is likewise possible to use mixtures of at least two materials in the electron-transporting layer, in which case at least one material is electron-conducting. Preferably, in such mixed electron-transporting layers, at least one phenanthroline compound is used, preferably BCP, or at least one pyridine compound according to the formula (VIII) below, preferably a compound of the formula (VIIIaa) below. More preferably, in mixed electron-transporting layers, in addition to at least one phenanthroline compound, alkaline earth metal or alkali metal hydroxyquinolate complexes, for example Liq, are used. Suitable alkaline earth metal or alkali metal hydroxyquinolate complexes are specified below (formula VII).

The electron-transporting layer may also be electronically doped in order to improve the transport properties of the materials used, in order firstly to make the layer thicknesses more generous (avoidance of pinholes/short circuits) and in order secondly to minimize the operating voltage of the device. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo, Appl. Phys. Lett., Vol. 82, No. 25, 23 Jun. 2003 and Pfeiffer et al., Organic Electronics 2003, 4, 89-103 and K. Walzer, B. Maennig, M. Pfeiffer, K. Leo, Chem. Soc. Rev. 2007, 107, 1233. For example, it is possible to use mixtures which lead to electrical n-doping of the electron-transporting layer. n-Doping is achieved by the addition of reducing materials. These mixtures may, for example, be mixtures of the abovementioned electron transport materials with alkali/alkaline earth metals or alkali/alkaline earth metal salts, for example Li, Cs, Ca, Sr, $Cs_2CO_3$, with alkali metal complexes, for example 8-hydroxyquinolatolithium (Liq), and with Y, Ce, Sm, Gd, Tb, Er, Tm, Yb, $Li_3N$, $Rb_2CO_3$, dipotassium phthalate, $W(hpp)_4$ from EP 1786050, or with compounds as described in EP1837926 B1.

The present invention therefore also relates to an inventive OLED which comprises an electron-transporting layer comprising at least two different materials, of which at least one material is electron-conducting.

In a preferred embodiment, the electron-transporting layer comprises at least one compound of the general formula (VII)

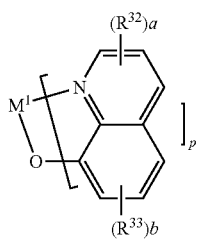

in which $R^{32}$ and $R^{33}$ are each independently F, $C_1$-$C_8$-alkyl, or $C_6$-$C_{14}$-aryl, which is optionally substituted by one or more $C_1$-$C_8$-alkyl groups, or two $R^{32}$ and/or $R^{33}$ substituents together form a fused benzene ring which is optionally substituted by one or more $C_1$-$C_8$-alkyl groups;

a and b are each independently 0, or 1, 2 or 3, $M^1$ is an alkaline metal atom or alkaline earth metal atom, p is 1 when $M^1$ is an alkali metal atom, p is 2 when $M^1$ is an alkaline earth metal atom.

A very particularly preferred compound of the formula (VII) is

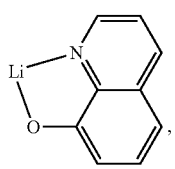

(Liq)

which may be present as a single species, or in other forms such as $Li_gQ_g$ in which g is an integer, for example $Li_6Q_6$. Q is an 8-hydroxyquinolate ligand or an 8-hydroxyquinolate derivative.

In a further preferred embodiment, the electron-transporting layer comprises at least one compound of the formula (VIII),

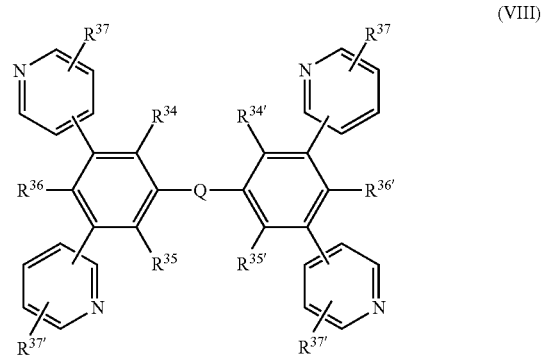

(VIII)

in which $R^{34}$, $R^{35}$, $R^{36}$, $R^{37}$, $R^{34'}$, $R^{35'}$, $R^{36'}$ and $R^{37'}$
are each independently H, $C_1$-$C_{18}$-alkyl, $C_1$-$C_{18}$-alkyl which is substituted by E and/or interrupted by D, $C_6$-$C_{24}$-aryl, $C_6$-$C_{24}$-aryl which is substituted by G, $C_2$-$C_{20}$-heteroaryl or $C_2$-$C_{20}$-heteroaryl which is substituted by G, Q is an arylene or heteroarylene group, each of which is optionally substituted by G;

D is —CO—; —COO—; —S—; —SO—; —$SO_2$—; —O—; —$NR^{40}$—; —$SiR^{45}R^{46}$—; —$POR^{47}$—; —$CR^{38}$=$CR^{39}$—; or —C≡C—; and E is —$OR^{44}$; —$SR^{44}$; —$NR^{40}R^{41}$; —$COR^{43}$; —$COOR^{42}$; —$CONR^{40}R^{41}$; —CN; or F;

G is E, $C_1$-$C_{18}$-alkyl, $C_1$-$C_{18}$-alkyl which is interrupted by D, $C_1$-$C_{18}$-perfluoroalkyl, $C_1$-$C_{18}$-alkoxy, or $C_1$-$C_{18}$-alkoxy which is substituted by E and/or interrupted by D, in which $R^{38}$ and $R^{39}$ are each independently H, $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—;

$R^{40}$ and $R^{41}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—; or $R^{40}$ and $R^{41}$ together form a 6-membered ring;

$R^{42}$ and $R^{43}$ are each independently $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—, $R^{44}$ is $C_6$-$C_{18}$-aryl; $C_6$-$C_{18}$-aryl which is substituted by $C_1$-$C_{18}$-alkyl or $C_1$-$C_{18}$-alkoxy; $C_1$-$C_{18}$-alkyl; or $C_1$-$C_{18}$-alkyl which is interrupted by —O—, $R^{45}$ and $R^{46}$ are each independently $C_1$-$C_{18}$-alkyl, $C_6$-$C_{18}$-aryl or $C_6$-$C_{18}$-aryl which is substituted by $C_1$-$C_{18}$-alkyl, $R^{47}$ is $C_1$-$C_{18}$-alkyl, $C_6$-$C_{18}$-aryl or $C_6$-$C_{18}$-aryl which is substituted by $C_1$-$C_{18}$-alkyl.

Preferred compounds of the formula (VIII) are compounds of the formula (VIIIa)

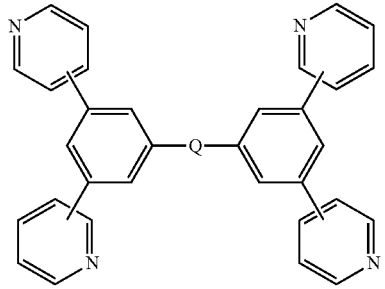
(VIIIa)

in which Q is:

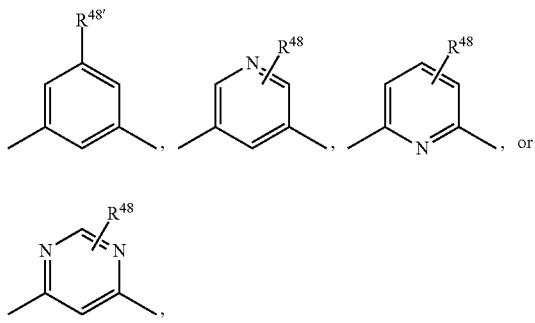

$R^{48}$ is H or $C_1$-$C_{18}$-alkyl and
$R^{48'}$ is H, $C_1$-$C_{18}$-alkyl or

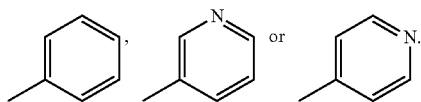

Particular preference is given to a compound of the formula (VIIIaa)

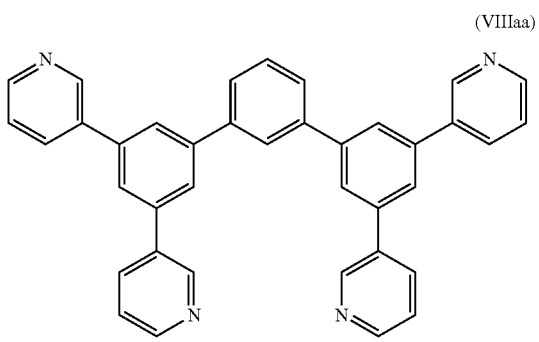 [SMILES: c1cncc(-c2cc(-c3cccnc3)cc(-c3cccc(-c4cc(-c5cccnc5)cc(-c5cccnc5)c4)c3)c2)c1]
(VIIIaa)

In a further, very particularly preferred embodiment, the electron-transporting layer comprises a compound of the formula

(Liq)

and a compound of the formula

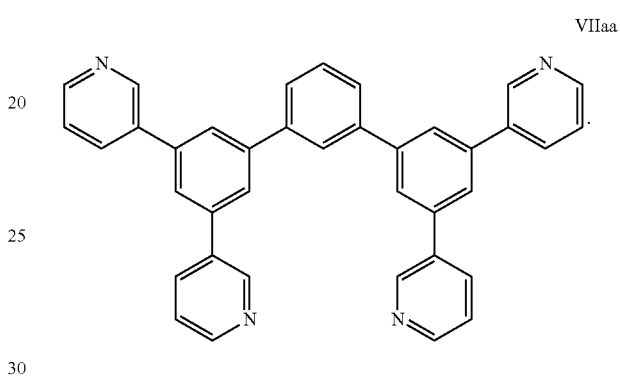
VIIaa

In a preferred embodiment, the electron-transporting layer comprises the compound of the formula (VII) in an amount of 99 to 1% by weight, preferably 75 to 25% by weight, more preferably about 50% by weight, where the amount of the compounds of the formulae (VII) and the amount of the compounds of the formulae (VIII) adds up to a total of 100% by weight.

The preparation of the compounds of the formula (VIII) is described in J. Kido et al., Chem. Commun. (2008) 5821-5823, J. Kido et al., Chem. Mater. 20 (2008) 5951-5953 and JP2008-127326, or the compounds can be prepared analogously to the processes disclosed in the aforementioned documents.

The preparation of the compounds of the formula (VII) is described, for example, in Christoph Schmitz et al. Chem. Mater. 12 (2000) 3012-3019 and WO00/32717, or the compounds can be prepared analogously to the processes disclosed in the aforementioned documents.

In a preferred embodiment, the invention relates to an inventive OLED wherein the electron-transporting layer comprises at least one phenanthroline derivative and/or pyridine derivative.

In a further preferred embodiment, the invention relates to an inventive OLED wherein the electron-transporting layer comprises at least one phenanthroline derivative and/or pyridine derivative and at least one alkali metal hydroxyquinolate complex.

In a further preferred embodiment, the invention relates to an inventive OLED wherein the electron-transporting layer comprises at least one phenanthroline derivative and/or pyridine derivative and 8-hydroxyquinolatolithium.

Some of the materials mentioned above as hole transport materials and electron-transporting materials can fulfill several functions. For example, some of the electron-transporting materials are simultaneously hole-blocking materials if they have a low-lying HOMO.

The cathode (5) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used. In addition, lithium-comprising organometallic compounds such as 8-hydroxyquinolatolithium (Liq), CsF, NaF, KF, $Cs_2CO_3$ or LiF may be applied between the organic layer and the cathode as an electron injection layer in order to reduce the operating voltage.

The OLED of the present invention may additionally comprise further layers which are known to those skilled in the art. For example, a layer which eases the transport of the positive charge and/or matches the band gaps of the layers to one another may be applied between the layer (2) and the light-emitting layer (3). Alternatively, this further layer may serve as a protective layer. In an analogous manner, additional layers may be present between the light-emitting layer (3) and the layer (4) in order to ease the transport of the negative charge and/or to match the band gaps between the layers to one another. Alternatively, this layer may serve as a protective layer.

In a preferred embodiment, the inventive OLED, in addition to the layers (1) to (5), comprises at least one of the further layers mentioned below:
  a hole injection layer between the anode (1) and the hole-transporting layer (2);
  a blocking layer for electrons between the hole-transporting layer (2) and the light-emitting layer (3);
  a blocking layer for holes between the light-emitting layer (3) and the electron-transporting layer (4);
  an electron injection layer between the electron-transporting layer (4) and the cathode (5).

As already mentioned above, however, it is also possible that the OLED does not have all of the layers (1) to (5) mentioned; for example, an OLED comprising layers (1) (anode), (3) (light-emitting layer) and (5) (cathode) is likewise suitable, in which case the functions of layers (2) (hole-transporting layer) and (4) (electron-transporting layer) are assumed by the adjoining layers. OLEDs having layers (1), (2), (3) and (5) or layers (1), (3), (4) and (5) are likewise suitable.

Those skilled in the art know how suitable materials have to be selected (for example on the basis of electrochemical investigations). Suitable materials for the individual layers are known to those skilled in the art and disclosed, for example, in WO 00/70655.

In addition, it is possible that some or all of the layers (1), (2), (3), (4) and (5) have been surface-treated in order to increase the efficiency of charge carrier transport. The selection of the materials for each of the layers mentioned is preferably determined by obtaining an OLED having a high efficiency.

The inventive OLED can be produced by methods known to those skilled in the art. In general, the OLED is produced by successive vapor deposition of the individual layers onto a suitable substrate. Suitable substrates are, for example, glass, inorganic materials such as ITO or IZO or polymer films. For the vapor deposition, customary techniques may be used, such as thermal evaporation, chemical vapor deposition (CVD), physical vapor deposition (PVD) and others.

In an alternative process, the organic layers may be coated from solutions or dispersions in suitable solvents, in which case coating techniques known to those skilled in the art are employed. Suitable coating techniques are, for example, spin-coating, the casting method, the Langmuir-Blodgett ("LB") method, the inkjet printing method, dip-coating, letterpress printing, screen printing, doctor blade printing, slit-coating, roller printing, reverse roller printing, offset lithography printing, flexographic printing, web printing, spray coating, coating by a brush or pad printing, and the like. Among the processes mentioned, in addition to the aforementioned vapor deposition, preference is given to spin-coating, the inkjet printing method and the casting method since they are particularly simple and inexpensive to perform. In the case that layers of the OLED are obtained by the spin-coating method, the casting method or the inkjet printing method, the coating can be obtained using a solution prepared by dissolving the composition in a concentration of 0.0001 to 90% by weight in a suitable organic solvent such as benzene, toluene, xylene, tetrahydrofuran, methyltetrahydrofuran, N,N-dimethylformamide, acetone, acetonitrile, anisole, dichloromethane, dimethyl sulfoxide, water and mixtures thereof.

It is possible that the layers of the OLED are all produced by the same coating method. Furthermore, it is likewise possible to conduct two or more different coating methods to produce the layers of the OLED.

In general, the different layers have the following thicknesses: anode (2) 500 to 5000 Å, preferably 1000 to 2000 Å (ångström); hole-transporting layer (3) 50 to 1000 Å, preferably 200 to 800 Å; light-emitting layer (4) 10 to 1000 Å, preferably 100 to 800 Å; electron-transporting layer (5) 50 to 1000 Å, preferably 200 to 800 Å; cathode (6) 200 to 10 000 Å, preferably 300 to 5000 Å. In addition, it is likewise possible to combine several layers by mixing. For example, the hole-transporting material can be mixed with the materials of the light-emitting layer and then applied together. The position of the recombination zone of holes and electrons in the inventive OLED and thus the emission spectrum of the OLED may be influenced by the relative thickness and concentration ratios of each layer. This means that the thickness of the electron transport layer should preferably be selected such that the electron/hole recombination zone is within the light-emitting layer. The ratio of the layer thicknesses of the individual layers in the OLED is dependent upon the materials used. The layer thicknesses of any additional layers used are known to those skilled in the art.

In a preferred embodiment, the present invention relates to an OLED comprising at least one inventive metal-carbene complex, and at least one compound of the general formula (X)

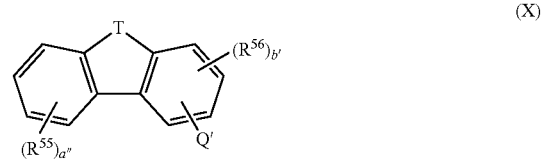

in which
T is $NR^{57}$, S, O or $PR^{57}$, preferably S or O, more preferably O;
$R^{57}$ is aryl, heteroaryl, alkyl, cycloalkyl or heterocycloalkyl;
Q' is $—NR^{58}R^{59}$, $—SiR^{70}R^{71}R^{72}$, $—P(O)R^{60}R^{61}$, $—PR^{62}R^{63}$, $—S(O)_2R^{64}$, $—S(O)R^{65}$, $—SR^{66}$ or $—OR^{67}$, preferably $—NR^{58}R^{59}$; more preferably

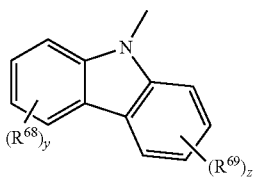

in which
- $R^{68}$, $R^{69}$ are each independently alkyl, cycloalkyl, heterocycloalkyl, aryl or heteroaryl; preferably methyl, carbazolyl, dibenzofuryl or dibenzothienyl;
- y, z are each independently 0, 1, 2, 3 or 4, preferably 0 or 1;
- $R^{55}$, $R^{56}$ are each independently alkyl, cycloalkyl, heterocycloalkyl, aryl, heteroaryl, $SiR^{70}R^{71}R^{72}$, a Q' group or a group with donor or acceptor action;
- a" is 0, 1, 2, 3 or 4;
- b' is 0, 1, 2 or 3;
- $R^{58}$, $R^{59}$ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action, and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl and a group with donor or acceptor action;
- $R^{70}$, $R^{71}$, $R^{72}$, $R^{60}$, $R^{61}$, $R^{62}$, $R^{63}$, $R^{64}$, $R^{65}$, $R^{66}$, $R^{67}$
  are each independently aryl, heteroaryl, alkyl, cycloalkyl or heterocycloalkyl,
or
two units of the general formula (X) are bridged to one another via a linear or branched, saturated or unsaturated bridge optionally interrupted by at least one heteroatom, via a bond or via O.

Preference is given to compounds of the formula (X) in which:
T is S or O, preferably O, and
Q' is

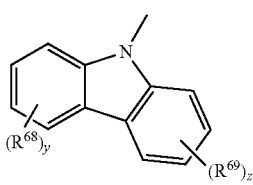

in which
- $R^{68}$, $R^{69}$ are each independently alkyl, cycloalkyl, heterocycloalkyl, aryl or heteroaryl; preferably methyl, carbazolyl, dibenzofuryl or dibenzothienyl;
- y, z are each independently 0, 1, 2, 3 or 4, preferably 0 or 1.

Particularly preferred compounds of the formula (X) have the following formula (Xa):

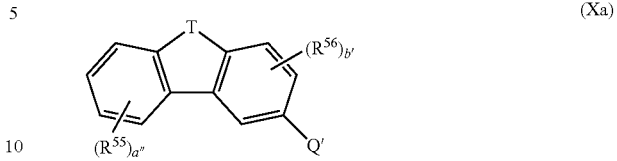

(Xa)

in which the symbols and indices Q', T, $R^{55}$, $R^{56}$, a" and b' are each as defined above.

Very particularly preferred compounds of the formula (X) have the formula (Xaa):

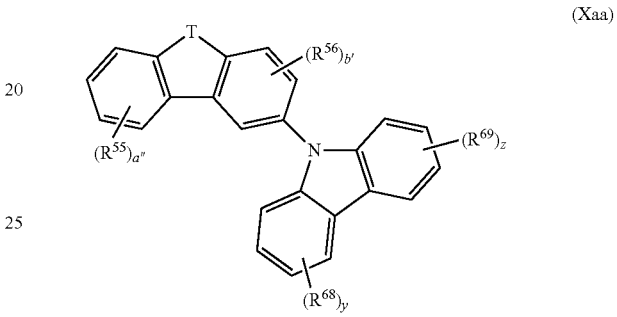

(Xaa)

in which the symbols and indices $R^{68}$, $R^{69}$ y, z, T, $R^{55}$, $R^{56}$, a" and b' are each as defined above.

In a very particularly preferred embodiment, in formula (Xaa):
- T is O or S, preferably O;
- a" is 1;
- b' is 0;
- y, z are each independently 0 or 1; and
- $R^{68}$, $R^{69}$ are each independently methyl, carbazolyl, dibenzofuryl or dibenzothienyl
- $R^{55}$ is substituted phenyl, carbazolyl, dibenzofuryl or dibenzothienyl.

Further preferred compounds of the formula (X) have the formula (Xab):

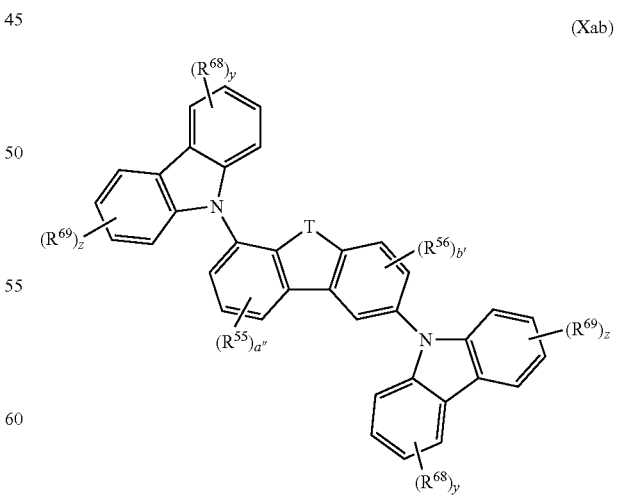

(Xab)

in which the symbols and indices each independently $R^{68}$, $R^{69}$ y, z, T, $R^{55}$, $R^{56}$, a" and b' are each independently as defined above.

In a very particularly preferred embodiment, in formula (Xab):
T is O or S, preferably O;
a″ is 0;
b′ is 0;
y, z are each independently 0 or 1; and
$R^{68}$, $R^{69}$ are each independently methyl, carbazolyl, dibenzofuryl or dibenzothienyl
$R^{55}$ is substituted phenyl, carbazolyl, dibenzofuryl or dibenzothienyl.

A very particularly preferred compound of the formula (Xab) is:

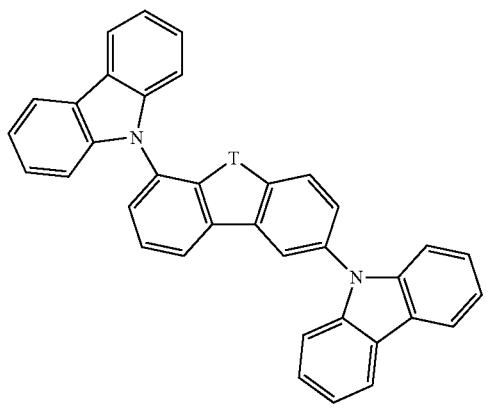

in which T is O or S, preferably O.

The compounds of the formula (X) can be prepared, for example, by the processes described in WO2010079051, WO2007/077810, JP2009267255 or US20090017331 A1, and WO2009/003898, or analogously to the processes described in the aforementioned documents.

In a further preferred embodiment, the compounds of the formula (X) have the formula (XI) or (XI*):

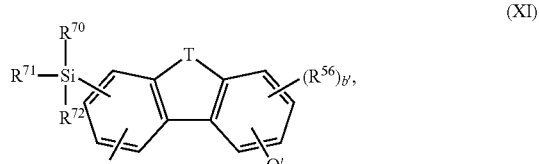

(XI)

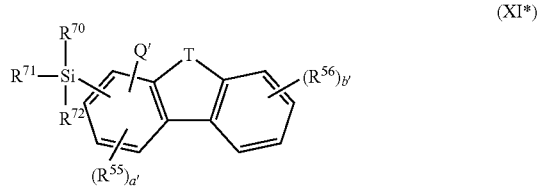

(XI*)

in which
T is $NR^{57}$, S, O or $PR^{57}$;
$R^{57}$ is aryl, heteroaryl, alkyl, cycloalkyl or heterocycloalkyl;
Q′ is $-NR^{58}R^{59}$, $-SiR^{70}R^{71}R^{72}$, $-P(O)R^{60}R^{61}$, $-PR^{62}R^{63}$, $-S(O)_2R^{64}$, $-S(O)R^{65}$, $-SR^{66}$ or $-OR^{67}$;
$R^{70}$, $R^{71}$, $R^{72}$ are each independently aryl, heteroaryl, alkyl, cycloalkyl, heterocycloalkyl or $OR^{73}$,
$R^{55}$, $R^{56}$ are each independently alkyl, cycloalkyl, heterocycloalkyl, aryl, heteroaryl, a Q′ group or a group with donor or acceptor action;
a′, b′ for the compound of the formula (XI): are each independently 0, 1, 2, 3; for the compound of the formula (XI*), a′ is 0, 1, 2 and b′ is 0, 1, 2, 3, 4;
$R^{58}$, $R^{59}$ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl and a group with donor or acceptor action;
$R^{73}$ are each independently $SiR^{74}R^{75}R^{76}$, aryl, heteroaryl, alkyl, cycloalkyl or heterocycloalkyl, optionally substituted by an $OR^{77}$ group,
$R^{77}$ are each independently $SiR^{74}R^{75}R^{76}$, aryl, heteroaryl, alkyl, cycloalkyl or heterocycloalkyl,
$R^{60}$, $R^{61}$, $R^{62}$, $R^{63}$, $R^{64}$, $R^{65}$, $R^{66}$, $R^{67}$, $R^{74}$, $R^{75}$, $R^{76}$ are each independently aryl, heteroaryl, alkyl, cycloalkyl or heterocycloalkyl,
or
two units of the general formulae (XI) and/or (XI*) are bridged to one another via a linear or branched, saturated or unsaturated bridge optionally interrupted by at least one heteroatom or via O, where this bridge in the general formulae (XI) and/or (XI*) is in each case attached to the silicon atoms in place of $R^{71}$.

The compounds of the general formula (X) can be used as a matrix (diluent material), hole/exciton blocker, electron/exciton blocker, electron transport material or hole transport material in combination with the complexes claimed, which then preferably serve as emitters. Inventive OLEDs which include both at least one compound of the formula (X) and a compound of the formula (I) exhibit particularly good efficiencies and lifetimes. Depending on the function in which the compound of the formula (X) is used, it is present in pure form or in different mixing ratios. In a particularly preferred embodiment, one or more compounds of the formula (X) are used as matrix material in the light-emitting layer.

For the compounds of the general formula (X), especially for the $R^{55}$ to $R^{77}$ radicals:

The terms aryl radical or group, heteroaryl radical or group, alkyl radical or group, cycloalkyl radical or group, heterocycloalkyl radical or group, alkenyl radical or group, alkynyl radical or group, and groups with donor and/or acceptor action are each defined as follows:

An aryl radical (or group) is understood to mean a radical having a base skeleton of 6 to 30 carbon atoms, preferably 6 to 18 carbon atoms, which is formed from an aromatic ring or a plurality of fused aromatic rings. Suitable base skeletons are, for example, phenyl, naphthyl, anthracenyl or phenanthrenyl, indenyl or fluorenyl. This base skeleton may be unsubstituted (which means that all carbon atoms which are substitutable bear hydrogen atoms), or may be substituted at one, more than one or all substitutable positions of the base skeleton.

Suitable substituents are, for example, deuterium, alkoxy radicals, aryloxy radicals, alkylamino groups, arylamino groups, carbazolyl groups, silyl groups, $SiR^{78}R^{79}R^{80}$, suitable silyl groups $SiR^{78}R^{79}R^{80}$ being specified below, alkyl radicals, preferably alkyl radicals having 1 to 8 carbon atoms, more preferably methyl, ethyl or i-propyl, aryl radicals, preferably $C_6$-aryl radicals, which may in turn be substituted or unsubstituted, heteroaryl radicals, preferably heteroaryl radicals which comprise at least one nitrogen atom, more preferably pyridyl radicals and carbazolyl radicals, alkenyl radicals, preferably alkenyl radicals which bear one double bond, more preferably alkenyl radicals having one double bond and 1 to 8 carbon atoms, alkynyl radicals, preferably alkynyl radicals having one triple bond, more preferably alkynyl radicals having one triple bond and 1 to 8 carbon atoms or groups with donor or acceptor action. Suitable groups with donor or acceptor action are specified below. The substituted aryl radicals most preferably bear substituents selected from the group consisting of methyl, ethyl, isopropyl, alkoxy, heteroaryl, halogen, pseudohalogen and amino, preferably arylamino. The aryl radical or the aryl group is preferably a $C_6$-$C_{18}$-aryl radical, more preferably a $C_6$-aryl radical, which is optionally substituted by at least one or more than one of the aforementioned substituents. The $C_6$-$C_{18}$-aryl radical, preferably $C_6$-aryl radical, more preferably has none, one, two, three or four, most preferably none, one or two, of the aforementioned substituents.

A heteroaryl radical or a heteroaryl group is understood to mean radicals which differ from the aforementioned aryl radicals in that at least one carbon atom in the base skeleton of the aryl radicals is replaced by a heteroatom, and in that the base skeleton of the heteroaryl radicals preferably has 5 to 18 ring atoms. Preferred heteroatoms are N, O and S. Heteroaryl radicals suitable with particular preference are nitrogen-containing heteroaryl radicals. Most preferably, one or two carbon atoms of the base skeleton are replaced by heteroatoms, preferably nitrogen. The base skeleton is especially preferably selected from systems such as pyridine, pyrimidine and five-membered heteroaromatics such as pyrrole, furan, pyrazole, imidazole, thiophene, oxazole, thiazole, triazole. In addition, the heteroaryl radicals may be fused ring systems, for example benzofuryl, benzothienyl, benzopyrrolyl, dibenzofuryl, dibenzothienyl, phenanthrolinyl, carbazolyl radicals, azacarbazolyl radicals or diazacarbazolyl radicals. The base skeleton may be substituted at one, more than one or all substitutable positions of the base skeleton. Suitable substituents are the same as have already been specified for the aryl groups.

An alkyl radical or an alkyl group is understood to mean a radical having 1 to 20 carbon atoms, preferably 1 to 10 carbon atoms, more preferably 1 to 8, most preferably 1 to 4 carbon atoms. This alkyl radical may be branched or unbranched and optionally be interrupted by one or more heteroatoms, preferably Si, N, O or S, more preferably N, O or S. In addition, this alkyl radical may be substituted by one or more of the substituents specified for the aryl groups. In addition, the alkyl radicals present in accordance with the invention may have at least one halogen atom, for example F, Cl, Br or I, especially F. In a further embodiment, the alkyl radicals present in accordance with the invention may be fully fluorinated. It is likewise possible that the alkyl radical bears one or more (hetero)aryl groups. In the context of the present application, for example, benzyl radicals are thus substituted alkyl radicals. In this context, all of the (hetero)aryl groups listed above are suitable. The alkyl radicals are more preferably selected from the group consisting of methyl, ethyl, isopropyl, n-propyl, n-butyl, iso-butyl and tert-butyl, very particular preference being given to methyl and ethyl.

A cycloalkyl radical or a cycloalkyl group is understood to mean a radical having 3 to 20 carbon atoms, preferably 3 to 10 carbon atoms, more preferably 3 to 8 carbon atoms. This base skeleton may be unsubstituted (which means that all carbon atoms which are substitutable bear hydrogen atoms) or substituted at one, more than one or all substitutable positions of the base skeleton. Suitable substituents are the groups already mentioned above for the aryl radicals. It is likewise possible that the cycloalkyl radical bears one or more (hetero)aryl groups. Examples of suitable cycloalkyl radicals are cyclopropyl, cyclopentyl and cyclohexyl.

A heterocycloalkyl radical or a heterocycloalkyl group is understood to mean radicals which differ from the aforementioned cycloalkyl radicals in that at least one carbon atom in the base skeleton of the cycloalkyl radicals is replaced by a heteroatom. Preferred heteroatoms are N, O and S. Most preferably, one or two carbon atoms of the base skeleton of the cycloalkyl radicals are replaced by heteroatoms. Examples of suitable heterocycloalkyl radicals are radicals derived from pyrrolidine, piperidine, piperazine, tetrahydrofuran, dioxane.

An alkenyl radical or an alkenyl group is understood to mean a radical which corresponds to the aforementioned alkyl radicals having at least two carbon atoms, with the difference that at least one C—C single bond of the alkyl radical is replaced by a C═C double bond. The alkenyl radical preferably has one or two double bonds.

An alkynyl radical or an alkynyl group is understood to mean a radical which corresponds to the aforementioned alkyl radicals having at least two carbon atoms, with the difference that at least one C—C single bond of the alkyl radical is replaced by a C≡C triple bond. The alkynyl radical preferably has one or two triple bonds.

An $SiR^{78}R^{79}R^{80}$ group is understood to mean a silyl radical in which
$R^{78}$, $R^{79}$ and $R^{80}$ are each independently alkyl, cycloalkyl, heterocycloalkyl, aryl, heteroaryl or $OR^{73}$.

An $SiR^{74}R^{75}R^{76}$ group is understood to mean a silyl radical in which
$R^{74}$, $R^{75}$ and $R^{76}$ are each independently alkyl, cycloalkyl, heterocycloalkyl, aryl, heteroaryl or $OR^{73}$.

In the context of the present application, a group or a substituent with donor or acceptor action is understood to mean the following groups:

Groups with donor action are understood to mean groups which have a +I and/or +M effect, and groups with acceptor action are understood to mean groups which have a −I and/or −M effect. Preferred suitable groups are selected from $C_1$-$C_{20}$-alkoxy, $C_6$-$C_{30}$-aryloxy, $C_1$-$C_{20}$-alkylthio, $C_6$-$C_{30}$-arylthio, $SiR^{81}R^{82}R^{83}$, $OR^{73}$, halogen radicals, halogenated $C_1$-$C_{20}$-alkyl radicals, carbonyl (—CO($R^{81}$)), carbonylthio (—C═O(S$R^{81}$)), carbonyloxy (—C═O(O$R^{81}$)), oxycarbonyl (—OC═O($R^{81}$)), thiocarbonyl (—SC═O($R^{81}$)), amino (—NR$^{81}$R$^{82}$), pseudohalogen radicals, amido (—C═O (NR$^{81}$)), —NR$^{81}$C═O($R^{83}$), phosphonate (—P(O)(O$R^{81}$)$_2$), phosphate (—OP(O)(O$R^{81}$)$_2$), phosphine (—PR$^{81}$R$^{82}$), phosphine oxide (—P(O)R$^{81}_2$), sulfate (—OS(O)$_2$O$R^{81}$), sulfoxide (—S(O)$R^{81}$), sulfonate (—S(O)$_2$O$R^{81}$), sulfonyl (—S(O)$_2$$R^{81}$, sulfonamide (—S(O)$_2$NR$^{81}$R$^{82}$), NO$_2$, boronic esters (—OB(O$R^{81}$)$_2$)) imino (—C═NR$^{81}$R$^{82}$)), borane radicals, stannane radicals, hydrazine radicals, hydrazone radicals, oxime radicals, nitroso groups, diazo groups, vinyl groups, sulfoximines, alanes, germanes, boroximes and borazines.

The $R^{81}$, $R^{82}$ and $R^{83}$ radicals mentioned in the aforementioned groups with donor or acceptor action are each independently:
substituted or unsubstituted $C_1$-$C_{20}$-alkyl or substituted or unsubstituted $C_6$-$C_{30}$-aryl, or $OR^{76}$, suitable and preferred alkyl and aryl radicals having been specified above. The $R^{81}$, $R^{82}$ and $R^{83}$ radicals are more preferably $C_1$-$C_6$-alkyl, e.g. methyl, ethyl or i-propyl, or phenyl. In a preferred embodiment—in the case of $SiR^{81}R^{82}R^{83}$-$R^{81}$, $R^{82}$ and $R^{83}$ are preferably each independently substituted or unsubstituted $C_1$-$C_{20}$-alkyl or substituted or unsubstituted aryl, preferably phenyl.

Preferred substituents with donor or acceptor action are selected from the group consisting of:

$C_1$- to $C_{20}$-alkoxy, preferably $C_1$-$C_6$-alkoxy, more preferably ethoxy or methoxy; $C_6$-$C_{30}$-aryloxy, preferably $C_6$-$C_{10}$-aryloxy, more preferably phenyloxy; $SiR^{81}R^{82}R^{83}$ where $R^{81}$, $R^{82}$ and $R^{83}$ are preferably each independently substituted or unsubstituted alkyl or substituted or unsubstituted aryl, preferably phenyl, for example $SiPh_3$ or SiMe; halogen radicals, preferably F, Cl, more preferably F, halogenated $C_1$-$C_{20}$-alkyl radicals, preferably halogenated $C_1$-$C_6$-alkyl radicals, most preferably fluorinated $C_1$-$C_6$-alkyl radicals, e.g. $CF_3$, $CH_2F$, $CHF_2$ or $C_2F_5$; amino, preferably dimethylamino, diethylamino or diarylamino, more preferably diarylamino; pseudohalogen radicals, preferably CN, —C(O)O$C_1$-$C_4$-alkyl, preferably—(O)OMe, P(O)$R_2$, preferably P(O)$Ph_2$.

Very particularly preferred substituents with donor or acceptor action are selected from the group consisting of methoxy, phenyloxy, halogenated $C_1$-$C_4$-alkyl, preferably $CF_3$, $CH_2F$, $CHF_2$, $C_2F_5$, halogen, preferably F, CN, $SiR^{81}R^{82}R^{83}$, suitable $R^{81}$, $R^{82}$ and $R^{83}$ radicals already having been specified, for example $SiMe_3$, diarylamino ($NR^{84}R^{85}$ where $R^{84}$, $R^{85}$ are each $C_6$-$C_{30}$-aryl), —C(O)O$C_1$-$C_4$-alkyl, preferably —C(O)OMe, P(O)$Ph_2$.

Halogen groups are preferably understood to mean F, Cl and Br, more preferably F and Cl, most preferably F.

Pseudohalogen groups are preferably understood to mean CN, SCN and OCN, more preferably CN.

The aforementioned groups with donor or acceptor action do not rule out the possibility that further radicals and substituents mentioned in the present application, but not included in the above list of groups with donor or acceptor action, have donor or acceptor action.

The aryl radicals or groups, heteroaryl radicals or groups, alkyl radicals or groups, cycloalkyl radicals or groups, heterocycloalkyl radicals or groups, alkenyl radicals or groups and groups with donor and/or acceptor action may—as mentioned above—be substituted or unsubstituted. In the context of the present application, an unsubstituted group is understood to mean a group in which the substitutable atoms of the group bear hydrogen atoms. In the context of the present application, a substituted group is understood to mean a group in which one or more substitutable atom(s) bear(s) a substituent in place of a hydrogen atom at least at one position. Suitable substituents are the substituents specified above for the aryl radicals or groups.

When radicals having the same numbering occur more than once in the compounds according to the present application, these radicals may each independently have the definitions specified.

The T radical in the compounds of the formula (X) is $NR^{57}$, S, O or $PR^{57}$, preferably $NR^{57}$, S or O, more preferably O or S, most preferably O.

The $R^{57}$ radical is aryl, heteroaryl, alkyl, cycloalkyl or heterocycloalkyl, preferably aryl, heteroaryl or alkyl, more preferably aryl, where the aforementioned radicals may be unsubstituted or substituted. Suitable substituents have been specified above. $R^{65}$ is more preferably phenyl which may be substituted by the aforementioned substituents or unsubstituted. $R^{57}$ is most preferably unsubstituted phenyl.

The Q' group in the compounds of the formula (X) is —$NR^{58}R^{59}$, —$SiR^{70}R^{71}R^{72}$, —P(O)$R^{60}R^{61}$, —$PR^{62}R^{63}$, —S(O)$_2R^{64}$, —S(O)$R^{65}$, —$SR^{66}$ or —$OR^{67}$; preferably $NR^{58}R^{59}$, —P(O)$R^{60}R^{61}$ or —$OR^{67}$, more preferably —$NR^{58}R^{59}$.

The $R^{58}$ to $R^{67}$, $R^{70}$, $R^{71}$, $R^{72}$ and $R^{74}$ to $R^{76}$ radicals are each defined as follows:

$R^{58}$, $R^{59}$ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl and a group with donor or acceptor action;

$R^{70}$, $R^{71}$, $R^{72}$ are each independently aryl, heteroaryl, alkyl, cycloalkyl, heterocycloalkyl or $OR^{73}$, $R^{73}$ is independently $SiR^{74}R^{75}R^{76}$, aryl, heteroaryl, alkyl, cycloalkyl or heterocycloalkyl, optionally substituted by one $OR^{77}$ group, $R^{77}$ is independently $SiR^{74}R^{75}R^{76}$, aryl, heteroaryl, alkyl, cycloalkyl or heterocycloalkyl, $R^{60}$, $R^{61}$, $R^{62}$, $R^{63}$, $R^{64}$, $R^{65}$, $R^{66}$, $R^{67}$, $R^{74}$, $R^{75}$, $R^{76}$ are each independently aryl, heteroaryl, alkyl, cycloalkyl or heterocycloalkyl, preferably aryl or heteroaryl, where the radicals may be unsubstituted or substituted by one or more of the radicals selected from alkyl, cycloalkyl, heterocycloalkyl, aryl, heteroaryl and a group with donor or acceptor action, more preferably unsubstituted or substituted phenyl, suitable substituents having been specified above, for example tolyl or a group of the formula

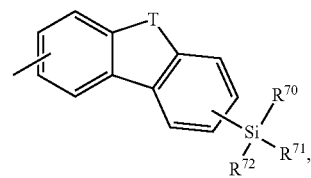

in which the T group is as defined for the compounds of the formula (XI) or (XI*) and the $R^{70}$, $R^{71}$ and $R^{72}$ radicals are defined above.

$R^{60}$, $R^{61}$, $R^{62}$, $R^{63}$, $R^{64}$, $R^{65}$, $R^{66}$ and $R^{67}$ are most preferably each independently phenyl, tolyl or a group of the formula

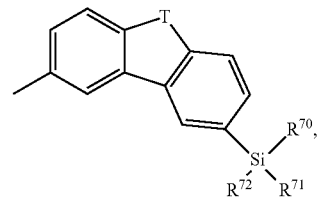

in which T is NPh, S or O.

Examples of —$NR^{58}R^{59}$ groups suitable with preference are selected from the group consisting of pyrrolyl, 2,5-dihydro-1-pyrrolyl, pyrrolidinyl, indolyl, indolinyl, isoindolinyl, carbazolyl, azacarbazolyl, diazacarbazolyl, imidazolyl, imidazolinyl, benzimidazolyl, pyrazolyl, indazolyl, 1,2,3-triazolyl, benzotriazolyl, 1,2,4-triazolyl, tetrazolyl, 1,3-oxazolyl, 1,3-thiazolyl, piperidyl, morpholinyl, 9,10-dihydroacridinyl and 1,4-oxazinyl, where the aforementioned groups may be unsubstituted or substituted by one or more substituents selected from alkyl, cycloalkyl, heterocycloalkyl, aryl, heteroaryl and a group with donor or acceptor action; the —$NR^{58}R^{59}$ group is preferably selected from carbazolyl, pyrrolyl, indolyl, imidazolyl, benzimidazolyl, azacarbazolyl and diazacarbazolyl, where the aforementioned groups may be unsubstituted or substituted by one or more substituents selected from alkyl, cycloalkyl, heterocycloalkyl, aryl, heteroaryl and a group with donor or acceptor action; the —NR$^{58}$R$^{59}$ group is more preferably carbazolyl which may be unsubstituted or substituted by one or more substituents selected from alkyl, cycloalkyl, heterocycloalkyl, aryl, heteroaryl and a group with donor or acceptor action.

Particularly preferred —NR$^{58}$R$^{59}$ groups are:

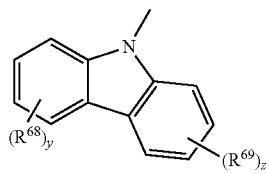

in which

R$^{68}$, R$^{69}$ are each independently alkyl, cycloalkyl, heterocycloalkyl, aryl or heteroaryl; preferably methyl, carbazolyl, dibenzofuryl or dibenzothienyl;

y, z are each independently 0, 1, 2, 3 or 4, preferably 0 or 1;

for example:

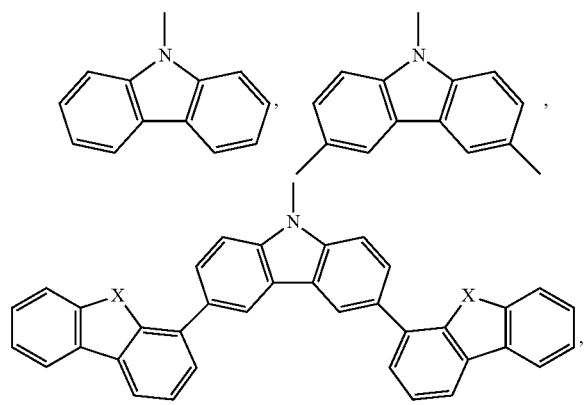

in which X is NPh, S or O;

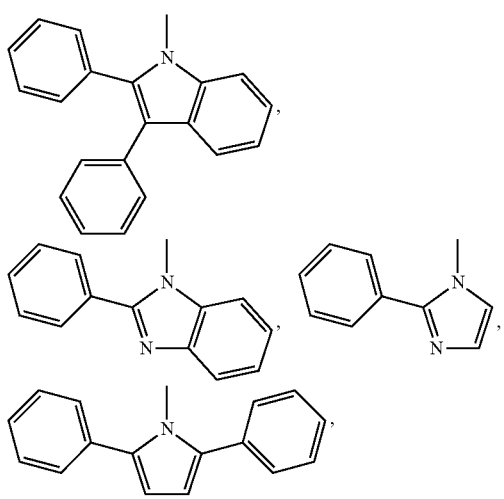

-continued

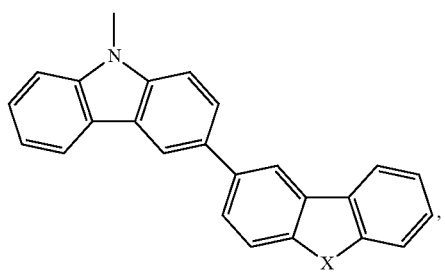

in which X is NPh, S or O,

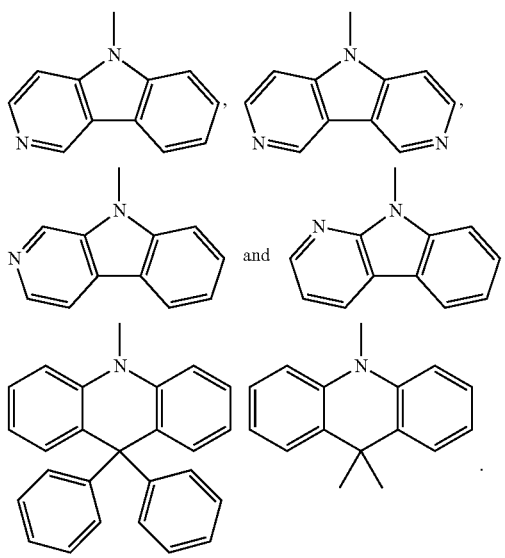

R$^{55}$, R$^{56}$ in the compounds of the formula (X) are each independently alkyl, cycloalkyl, heterocycloalkyl, aryl, heteroaryl, a further A group or a group with donor or acceptor action; preferably each independently alkyl, aryl, heteroaryl or a group with donor or acceptor action. For example, R$^{55}$ or R$^{56}$ may each independently be:

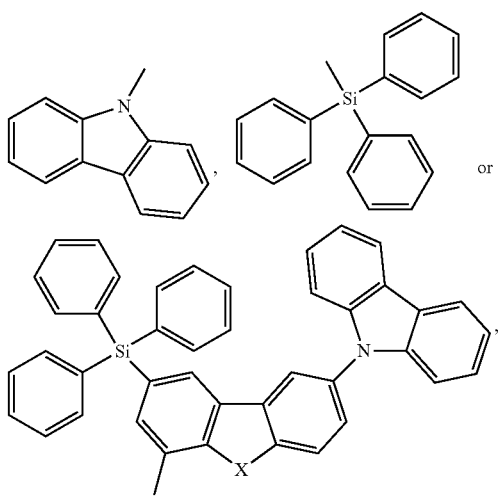

-continued

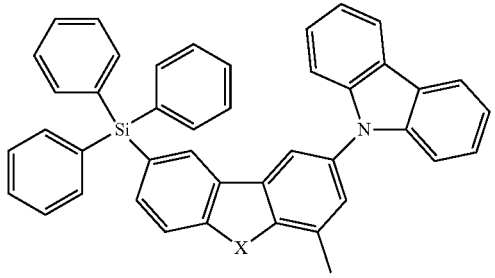

in which X is NPh, S or O.

In the compounds of the formula (X) a" R$^{55}$ groups and/or b' R$^{56}$ groups may be present, where a" and b' are:
a" is 0, 1, 2, 3 or 4; preferably independently 0, 1 or 2;
b' is 0, 1, 2 or 3; preferably independently 0, 1 or 2.

Most preferably at least a" or b' is 0, very especially preferably a" and b' are each 0 or a" is 1 and b' is 0.

R$^{73}$ in the compounds of the general formula (XI) is generally independently SiR$^{74}$R$^{75}$R$^{76}$, aryl, heteroaryl, alkyl, cycloalkyl or heterocycloalkyl, optionally substituted by an OR$^{77}$ group.

R$^{77}$ in compounds of the general formula (XI) is generally independently aryl, heteroaryl, alkyl, cycloalkyl or heterocycloalkyl.

The OR$^{77}$ substituent optionally present may generally be present in the radicals mentioned at all sites which appear suitable to the person skilled in the art.

In a further embodiment, two units of the general formula (XI) and/or (XI*) are bridged to one another via a linear or branched, saturated or unsaturated bridge optionally interrupted by at least one heteroatom or via O, where this bridge in the general formula (XI) and/or (XI*) is in each case attached to the silicon atoms in place of R$^{71}$.

This bridge is preferably selected from the group consisting of —CH$_2$—, —C$_2$H$_4$—, —C$_3$H$_6$—, —C$_4$H$_8$—, —C$_6$H$_{12}$—, —C$_8$H$_{16}$—, —C$_9$H$_{18}$—, —CH(C$_8$H$_7$)CH$_2$—, —C$_2$H$_4$(CF$_2$)$_8$ C$_2$H$_4$—, —C≡C—, -1,4-(CH$_2$)$_2$-phenyl-(CH$_2$)$_2$—, 1,3-(CH$_2$)$_2$-phenyl-(CH$_2$)$_2$—, -1,4-phenyl-, -1,3-phenyl-, —O—, —O—Si(CH$_3$)$_2$—O—, —O—Si(CH$_3$)$_2$—O—Si(CH$_3$)$_2$—O—, —O—

In a preferred embodiment of the present application, the compounds of the general formula (X) have the general formula (XIa), (XIb), (XIc), (XId) or (XIe), i.e. they are preferred embodiments of the compounds of the general formula (XI) or (XI*):

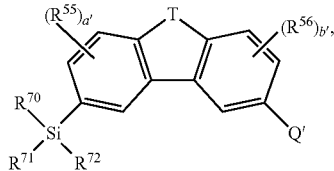
(XIa)

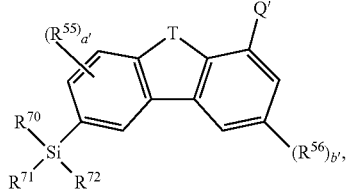
(XIb)

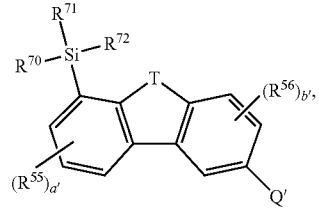
(XIc)

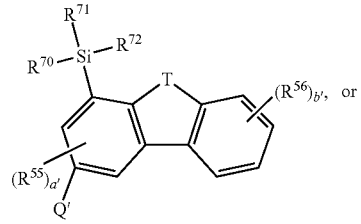
(XId)

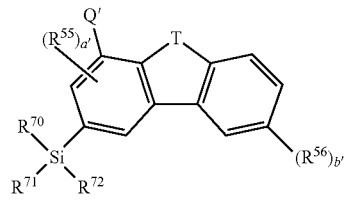
(XIe)

in which the Q', T, R$^{70}$, R$^{71}$, R$^{72}$, R$^{55}$, R$^{56}$ radicals and groups, and a' and b', are each as defined above.

In another embodiment preferred in accordance with the invention, R$^{70}$, R$^{71}$ or R$^{72}$ in the compounds of the general formula (XI) or (XI*) are aromatic units of the general formulae (XIi) and/or (XIi*)

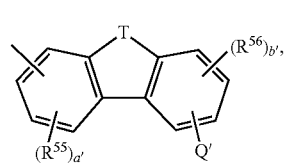
(XIi)

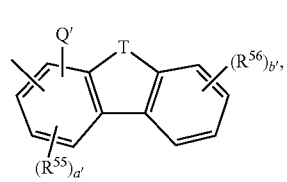
(XIi*)

where R$^{55}$, R$^{56}$, Q', T, a' and b' are each as defined above.

The present invention therefore relates, in one embodiment, to an inventive OLED where R$^{70}$, R$^{71}$ or R$^{72}$ in the compounds of the general formula (XI) or (XI*) are aromatic units of the general formulae (XIi) and/or (XIi*)

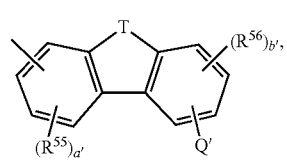
(XIi)

-continued
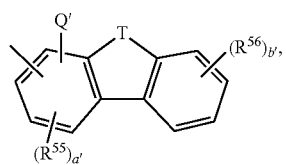
where $R^{56}$, $R^{56}$, Q', T, a' and b' are each as defined above.
In a preferred embodiment, the present invention relates to an OLED wherein the compound of the general formula (XI) or (XI*) is selected from the following group:
-continued
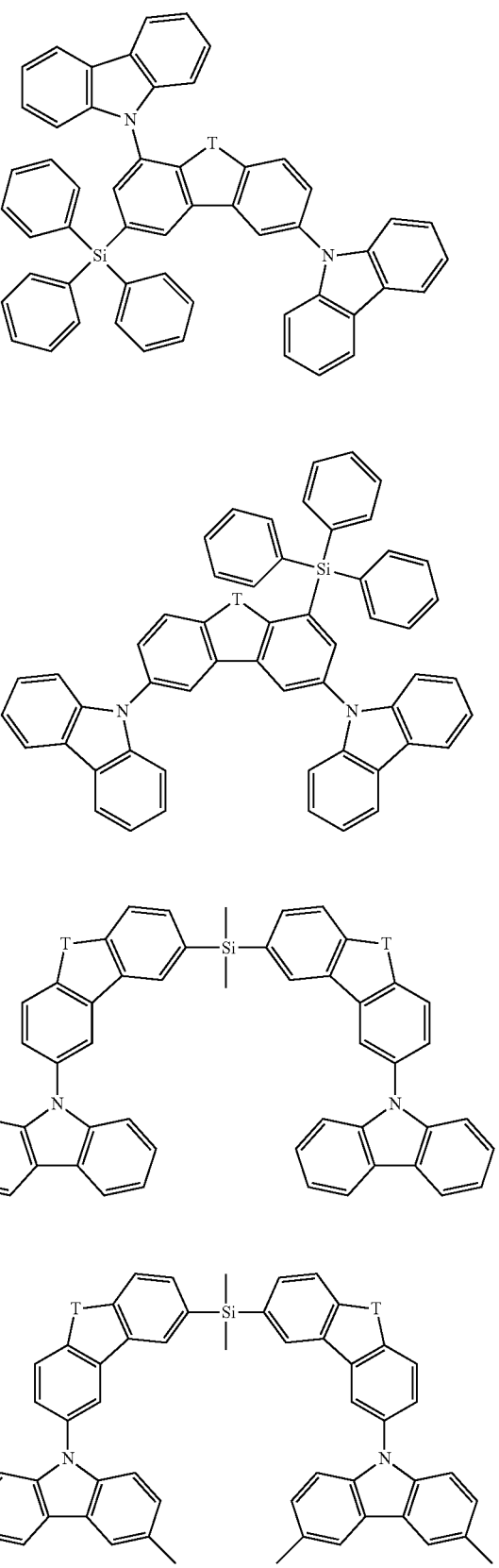

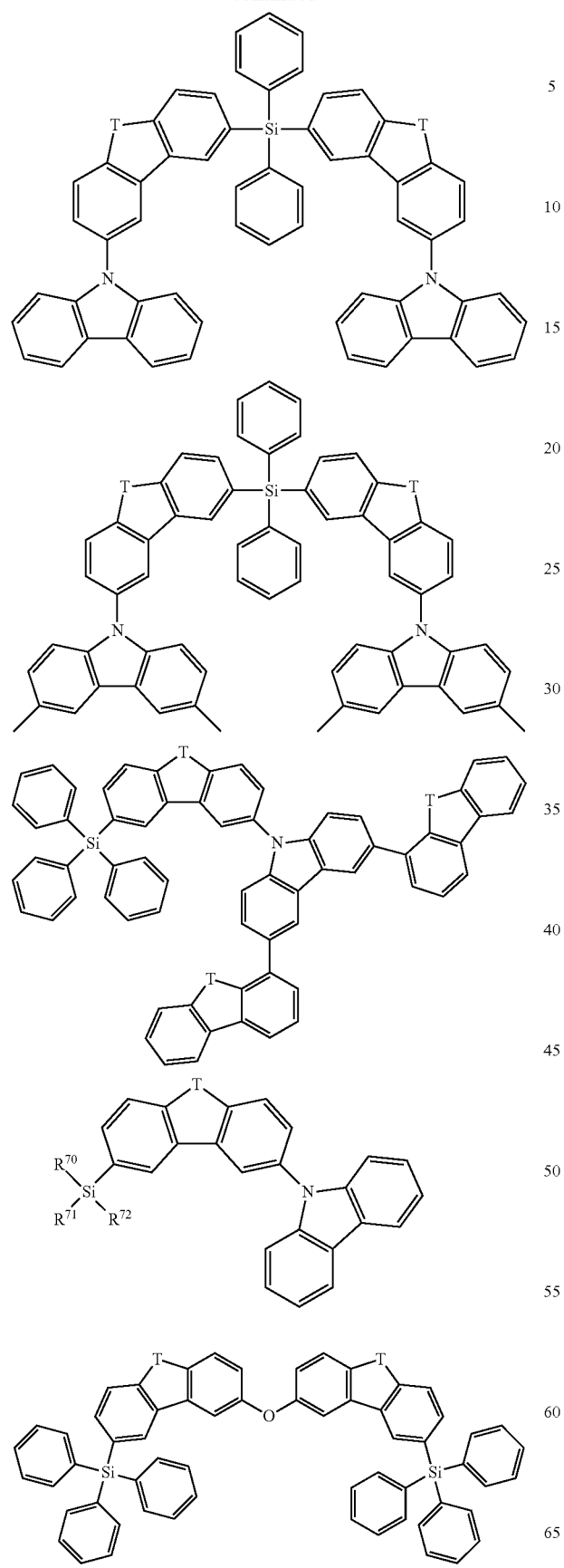
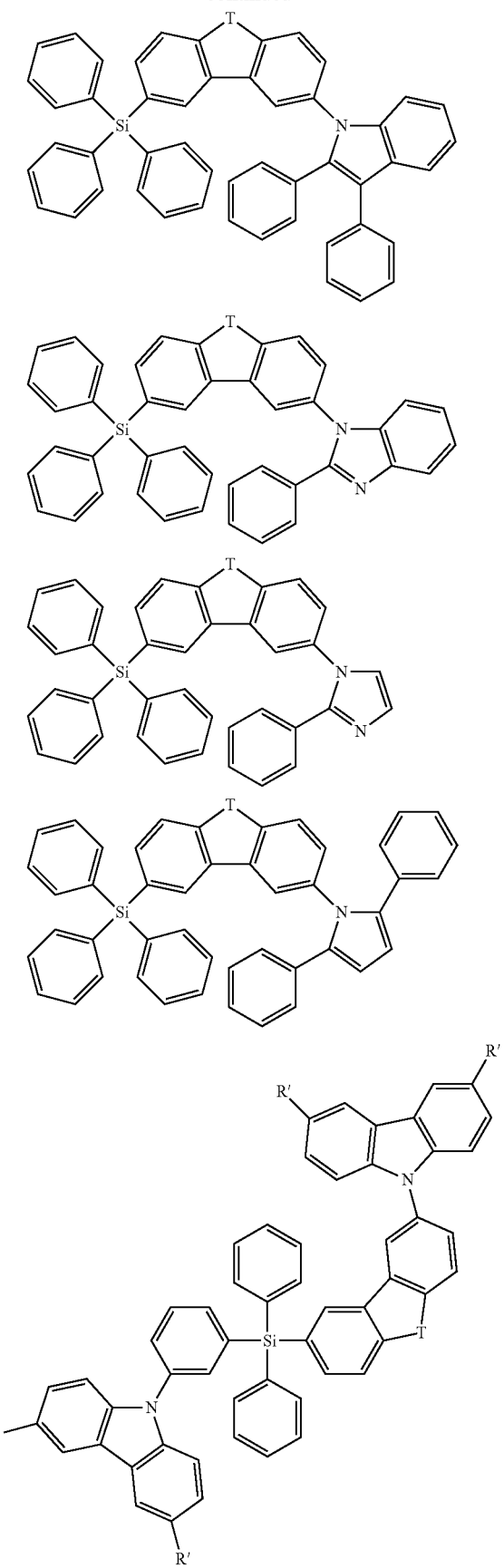

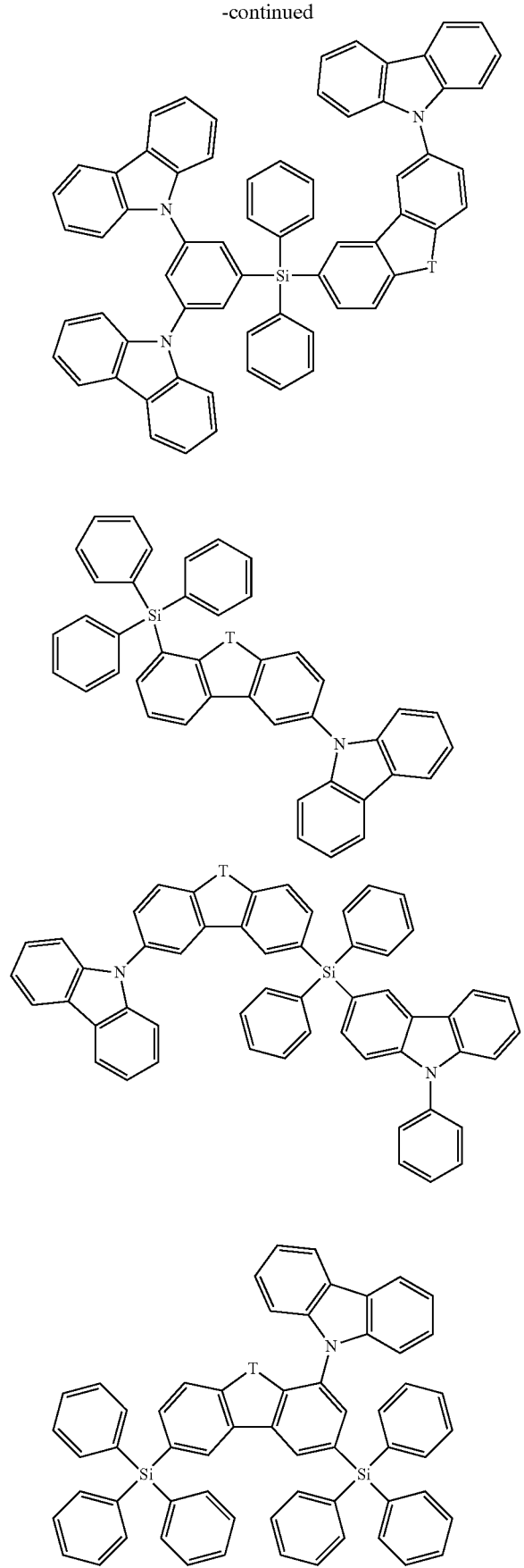
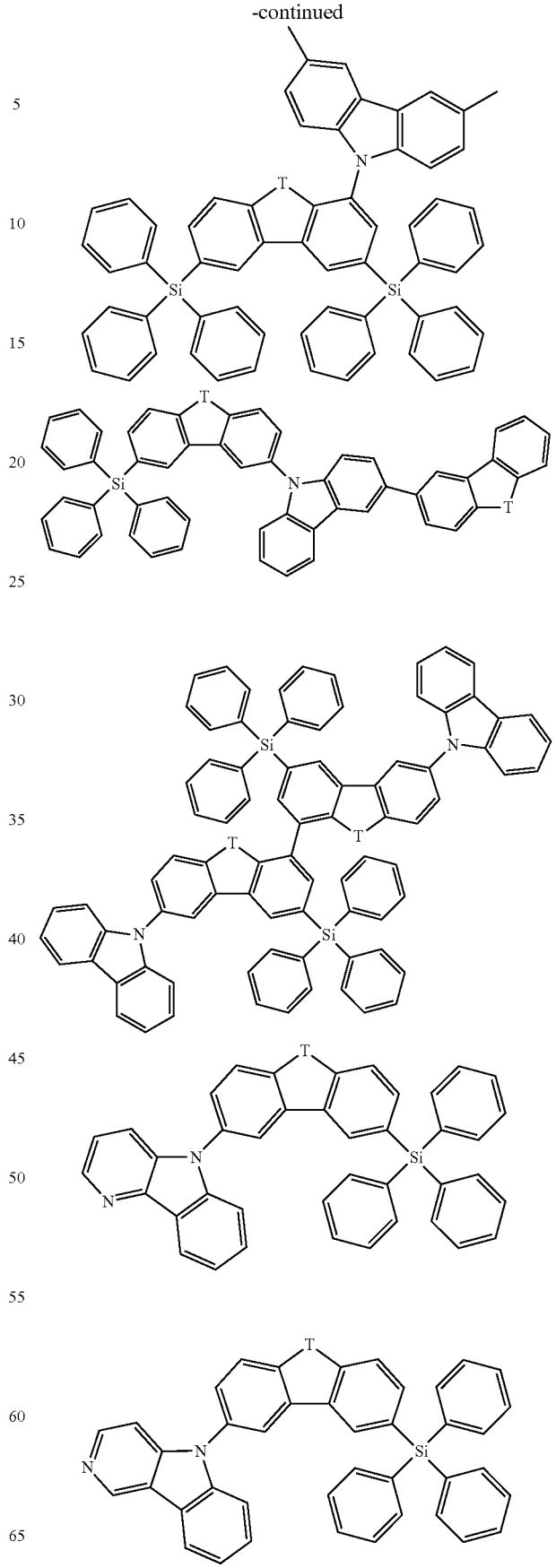

-continued
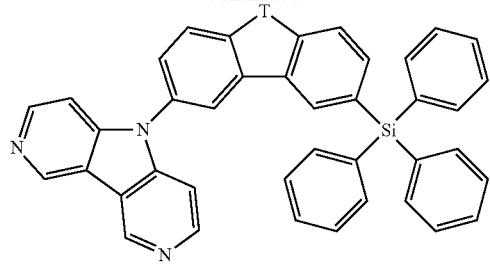
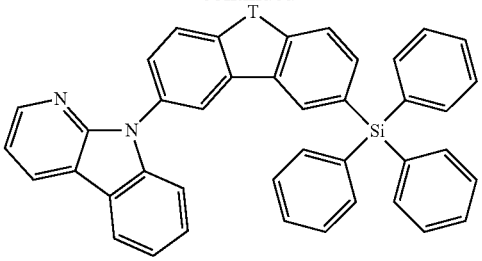
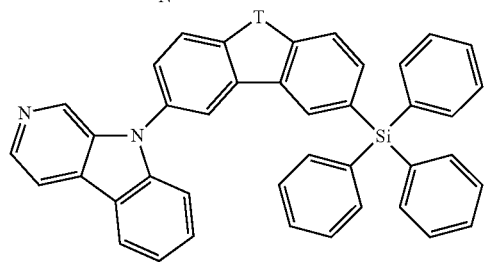
In these particularly preferred compounds of the general formula (XI) or (XI*):
T is S or O, and
R' is H or CH$_3$; and
R$^{70}$, R$^{71}$, R$^{72}$ are each phenyl, carbazolyl, dibenzofuran or dibenzothiophene.
Further particularly suitable compounds of the general formula (XI) or (XI*) are:
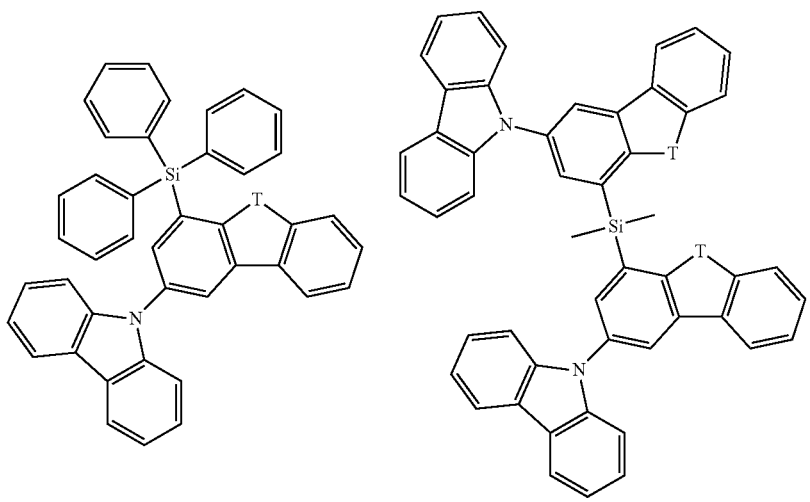
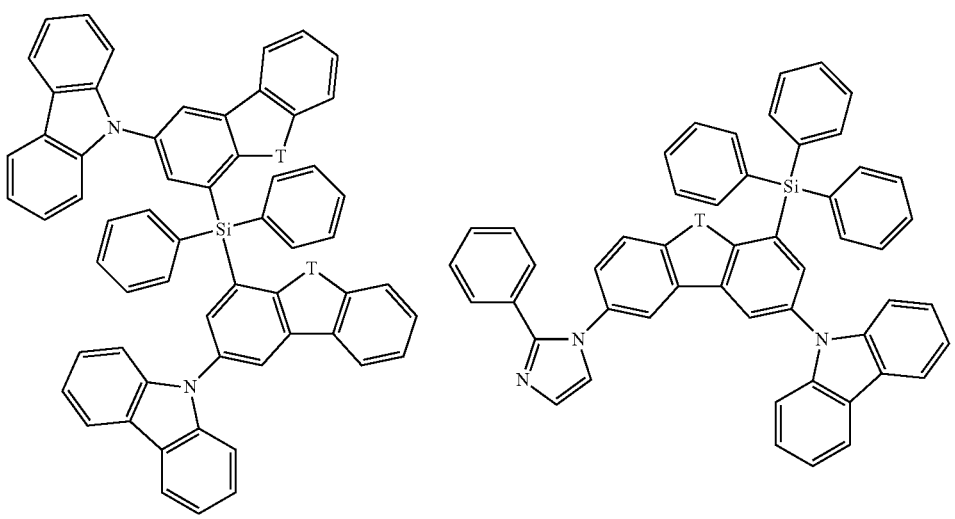

-continued
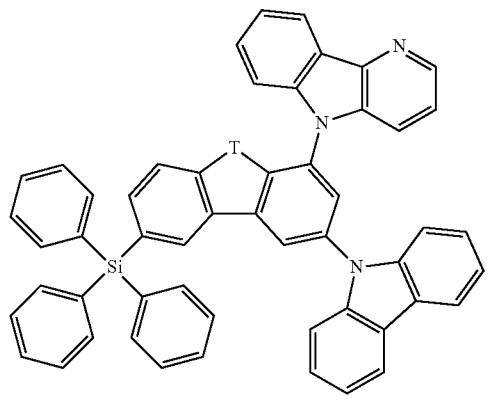 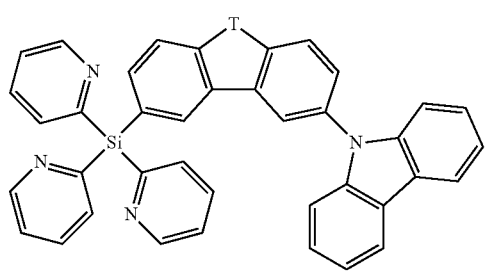
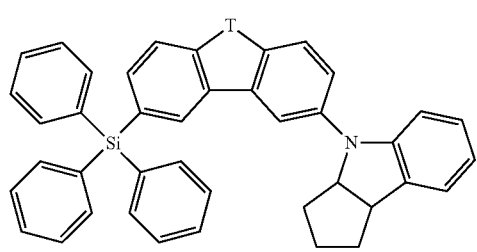 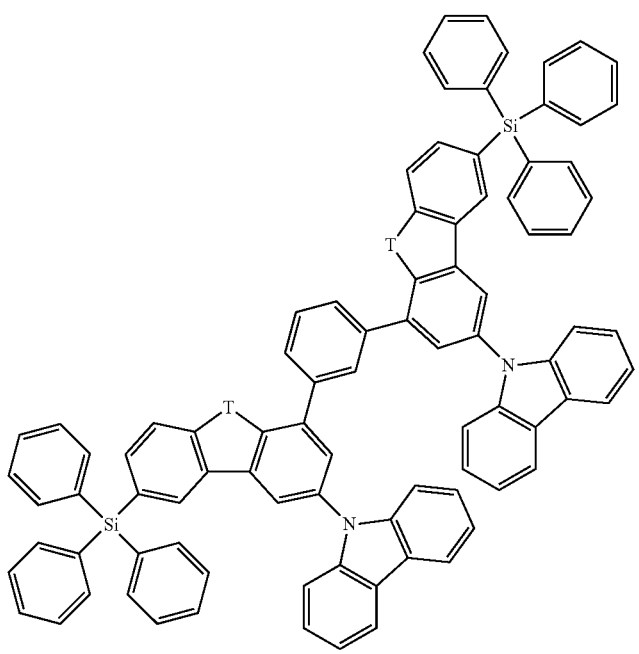
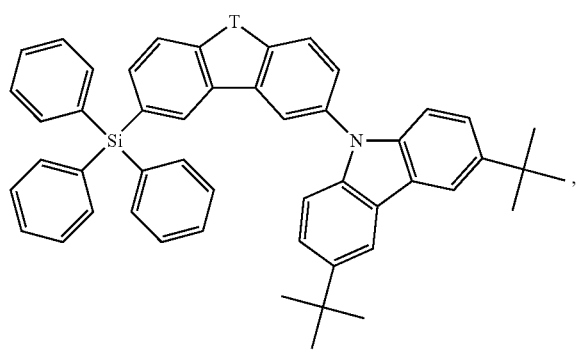

-continued
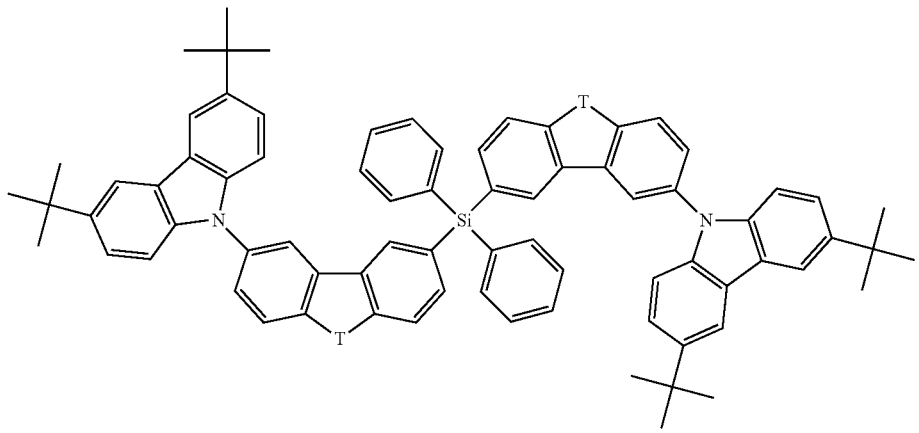
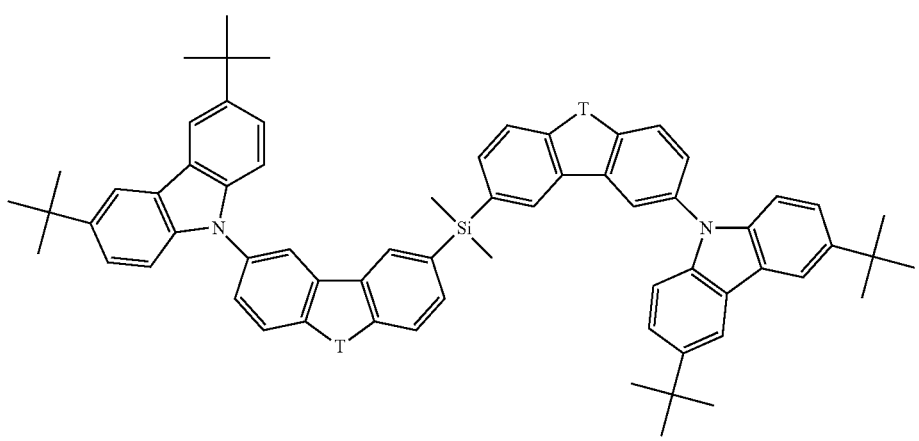
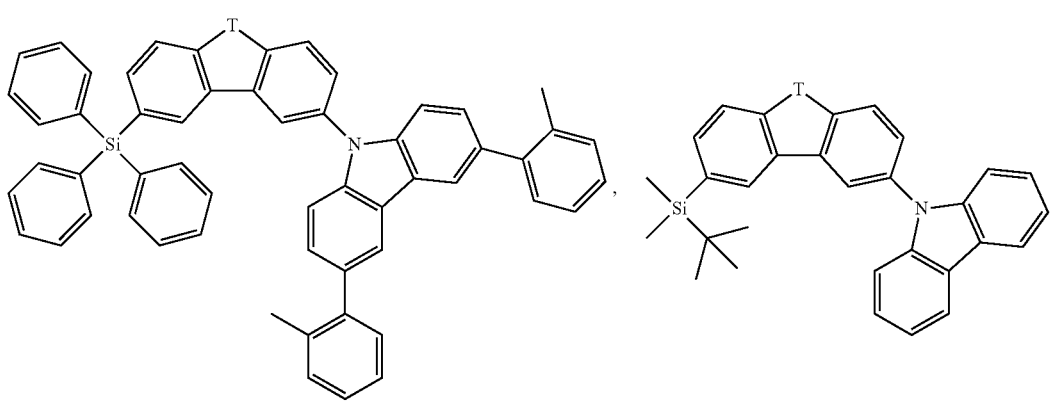
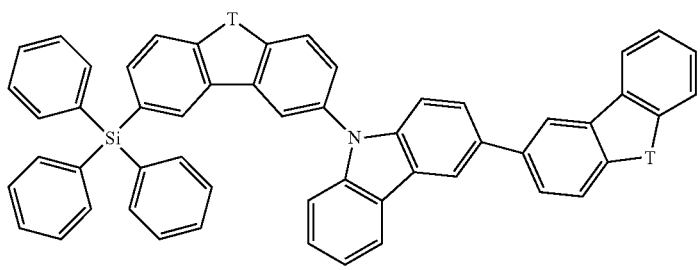

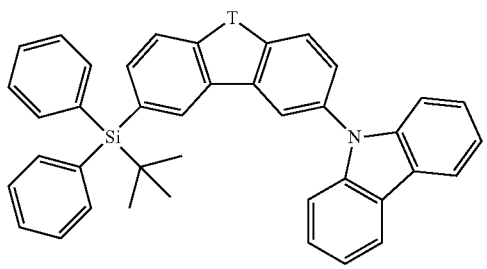
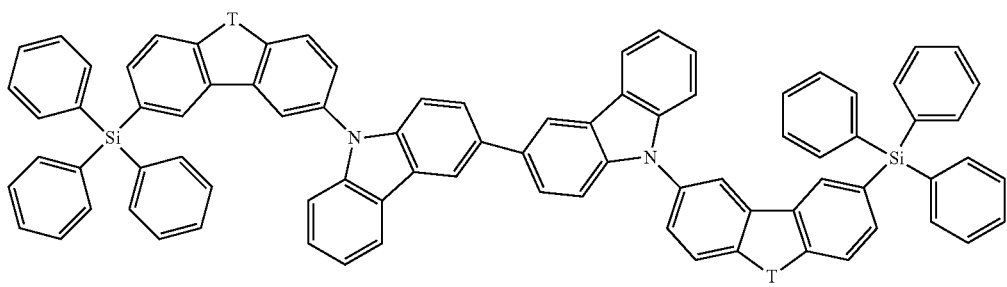
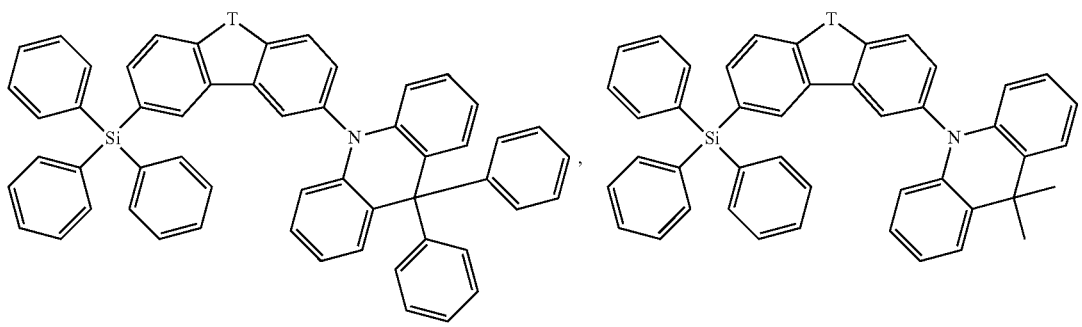
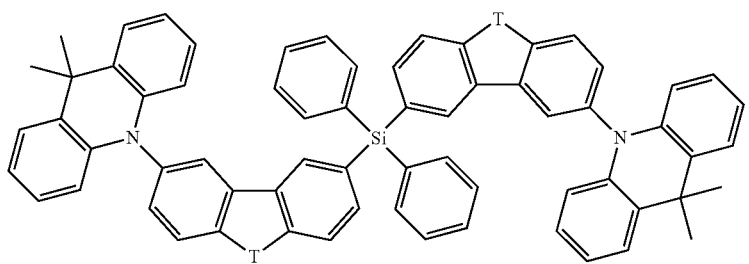
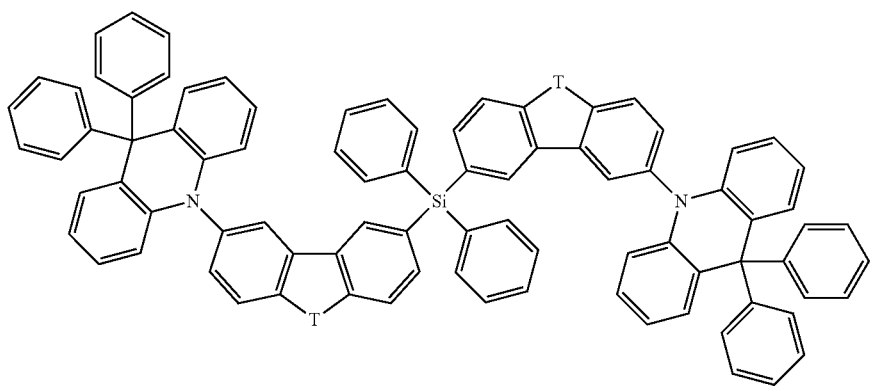

-continued
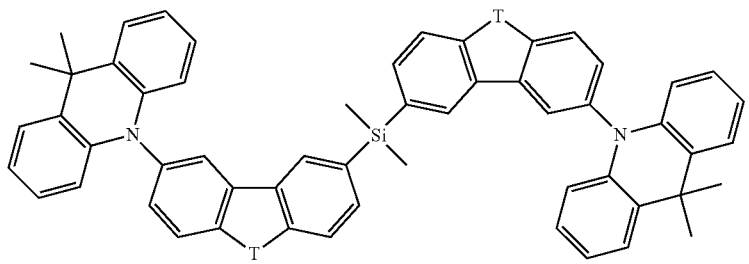
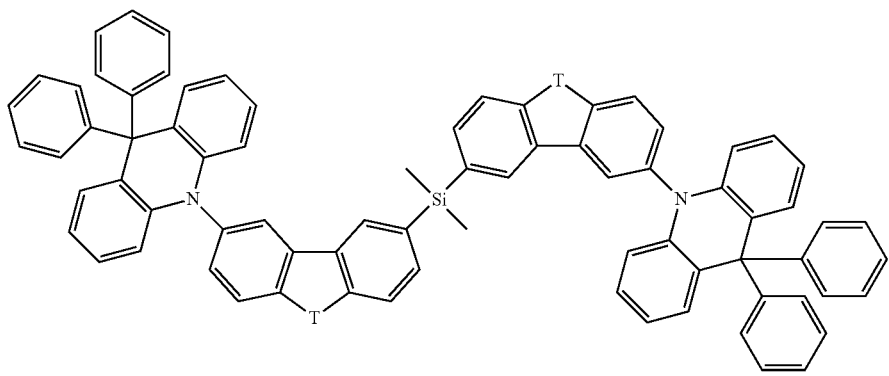
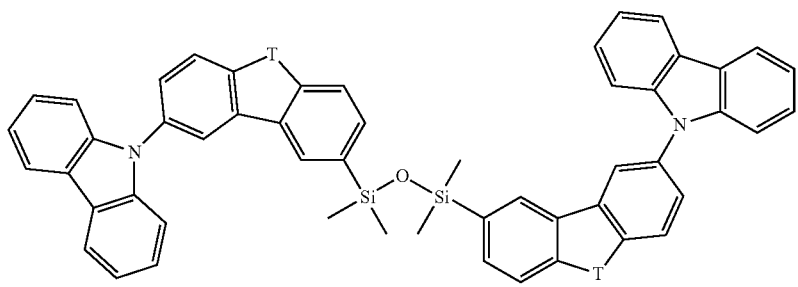
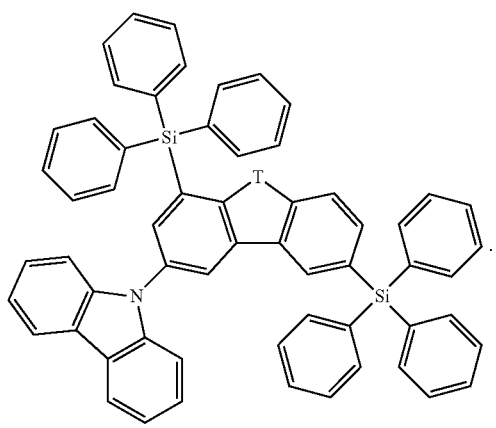

In these particularly preferred compounds of the general formula (XI) or (XI*) too, T is O or S, preferably O.

Further suitable compounds of the general formula (XI) or (XI*) correspond to the following formula (XII)

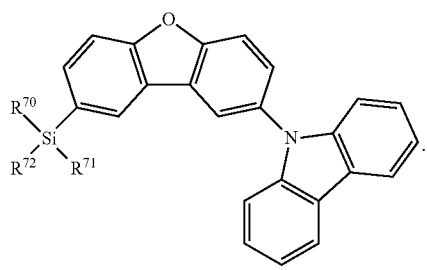

(XII)

In the general formula (XII), $R^{70}$, $R^{71}$, $R^{72}$ are defined as follows:

Each independently linear or branched alkyl radical optionally bearing at least one functional group, optionally interrupted by at least one heteroatom and having 1 to 30 carbon atoms, alkoxy radical having 1 to 20 carbon atoms, substituted or unsubstituted cycloalkyl radical having 3 to 20 carbon atoms, substituted or unsubstituted aryl radical having 6 to 30 carbon atoms; preferred compounds of the formula (XII) and preferred $R^{70}$, $R^{71}$, $R^{72}$ radicals are specified in European application EP10 187 176.2 and U.S. application 61/391,712 and PCT application PCT/EP2010/069541, all of which were yet to be published at the priority date of the present application.

Furthermore, European application EP10 187 176.2 and U.S. application 61/391,712 and PCT application PCT/EP2010/069541, all of which were yet to be published at the priority date of the present application, cite further suitable compounds of the formula (X).

In a further preferred embodiment, the present invention relates to an OLED comprising at least one inventive metalcarbene complex of the formula (I) and at least one compound of the general formula (X), where the compound of the general formula (X) has the general formula (XIV):

A further embodiment of the present invention relates to an inventive organic light-emitting diode in which the compound of the general formula VI is a 3,6-disilyl-substituted compound of the general formula VIa:

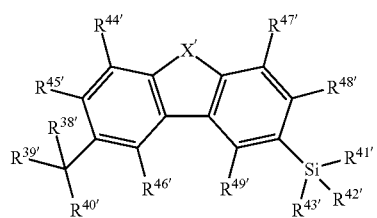

(XIV)

in which:

X' is S, O;

$R^{37'}$ is substituted or unsubstituted $C_1$-$C_{20}$-alkyl, substituted or unsubstituted $C_6$-$C_{30}$-aryl or substituted or unsubstituted heteroaryl having 5 to 30 ring atoms; preferably substituted or unsubstituted $C_6$-$C_{30}$-aryl or unsubstituted $C_1$-$C_{20}$-alkyl, more preferably substituted or unsubstituted $C_6$-$C_{10}$-aryl, most preferably substituted or unsubstituted phenyl, suitable substituents having been specified above;

$R^{38'}$, $R^{39'}$, $R^{40'}$, $R^{41'}$, $R^{42'}$, $R^{43'}$ are each independently substituted or unsubstituted $C_1$-$C_{20}$-alkyl or substituted or unsubstituted $C_6$-$C_{30}$-aryl or a structure of the general formula (c);

preferably at least one of the $R^{38'}$, $R^{39'}$ or $R^{40'}$ radicals and/or at least one of the $R^{41'}$, $R^{42'}$ or $R^{43'}$ radicals is substituted or unsubstituted $C_6$-$C_{30}$-aryl, more preferably substituted or unsubstituted $C_6$-$C_{10}$-aryl, most preferably substituted or unsubstituted phenyl, suitable substituents having been specified above, and/or one of the $R^{38'}$, $R^{39'}$ or $R^{40'}$ radicals and/or one of the $R^{41'}$, $R^{42}$ or $R^{43'}$ radicals is a radical of the structure (c);

$R^{44'}$, $R^{45'}$, $R^{46'}$, $R^{47'}$, $R^{48'}$, $R^{49'}$ are each independently hydrogen or as defined for $R^{a'}$ and $R^{b'}$, i.e. each independently substituted or unsubstituted $C_1$-$C_{20}$-alkyl, substituted or unsubstituted $C_6$-$C_{20}$-aryl, substituted or unsubstituted heteroaryl having 5 to 30 ring atoms or a substituent with donor or acceptor action, suitable substituents with donor or acceptor action having been specified above; preferably hydrogen, substituted or unsubstituted $C_1$-$C_6$-alkyl, substituted or unsubstituted $C_6$-$C_{10}$-aryl or $SiR^{34'}R^{35'}R^{36'}$; more preferably hydrogen, methyl, ethyl, phenyl, $CF_3$ or $SiR^{34'}R^{35'}R^{36'}$ where $R^{34'}$, $R^{35'}$ and $R^{36'}$ are preferably each independently substituted or unsubstituted $C_1$-$C_{20}$-alkyl or substituted or unsubstituted phenyl; more preferably, at least one of the $R^{34'}$, $R^{35'}$ or $R^{36'}$ radicals is substituted or unsubstituted phenyl; most preferably, at least one of the $R^{34'}$, $R^{35'}$ and $R^{36'}$ radicals is substituted phenyl, suitable substituents having been specified above;

and the further radials and indices $R^{34'}$, $R^{35'}$, $R^{36'}$ are each as defined above.

In a particularly preferred embodiment, the compounds of the formula (XIV) used in the inventive organic light-emitting diodes have the following definitions for the $R^{37'}$ to $R^{43'}$, $R^{a'}$ and $R^{a'}$ radicals, and X' group:

X' is $NR^{37'}$;

$R^{37'}$ is substituted or unsubstituted $C_6$-$C_{30}$-aryl, preferably substituted or unsubstituted $C_6$-$C_{10}$-aryl, more preferably substituted or unsubstituted phenyl, suitable substituents having been specified above;

$R^{38'}$, $R^{39'}$, $R^{40'}$, $R^{41'}$, $R^{42'}$, $R^{43'}$, are each independently substituted or unsubstituted $C_1$-$C_{20}$-alkyl or substituted or unsubstituted $C_6$-$C_{30}$-aryl, or a structure of the general formula (c), preferably each independently substituted or unsubstituted $C_1$-$C_6$-alkyl or substituted or unsubstituted $C_6$-$C_{10}$-aryl, more preferably substituted or unsubstituted $C_1$-$C_6$-alkyl or substituted or unsubstituted phenyl; where, in one embodiment, at least one of the $R^{38'}$, $R^{39'}$ or $R^{40'}$ radials and/or at least one of the $R^{41'}$, $R^{42'}$ or $R^{43'}$ radicals is substituted or unsubstituted $C_6$-$C_{30}$-aryl, preferably substituted or unsubstituted $C_6$-$C_{10}$-aryl, more preferably substituted or unsubstituted phenyl, preferred substituents having been specified above;

$R^{44'}$, $R^{45'}$, $R^{46'}$, $R^{47'}$, $R^{48'}$, $R^{49'}$ are each independently hydrogen or as defined for $R^{a'}$ and $R^{b'}$, i.e. each independently substituted or unsubstituted $C_1$-$C_{20}$-alkyl, substituted or unsubstituted $C_6$-$C_{30}$-aryl, substituted or unsubstituted heteroaryl having 5 to 30 ring atoms or a substituent with donor or acceptor action, suitable substituents with donor or acceptor action already having been specified above; preferably hydrogen, substituted or unsubstituted $C_1$-$C_6$-alkyl, substituted or unsubstituted $C_6$-$C_{10}$-aryl or $SiR^{34'}R^{35'}R^{36'}$; more preferably hydrogen, methyl, ethyl, phenyl, $CF_3$ or $SiR^{34'}R^{35'}R^{36'}$;

$R^{34'}$, $R^{35'}$, $R^{36'}$
are each independently substituted or unsubstituted $C_1$-$C_{20}$-alkyl or substituted or unsubstituted $C_6$-$C_{30}$-aryl, preferably substituted or unsubstituted $C_1$-$C_6$-alkyl or substituted or unsubstituted $C_6$-$C_{10}$-aryl, where $R^{34'}$, $R^{35'}$ and $R^{36'}$ are more preferably each independently substituted or unsubstituted $C_1$-$C_{20}$-alkyl or substituted or unsubstituted phenyl; more preferably, at least one of the $R^{34'}$, $R^{35'}$ or $R^{36'}$ radicals is substituted or unsubstituted phenyl; most preferably, at least one of the $R^{34'}$, $R^{35'}$ and $R^{36'}$ radicals is substituted phenyl, suitable substituents having been specified above.

An example of a particularly suitable compound of the formula (XIV) is

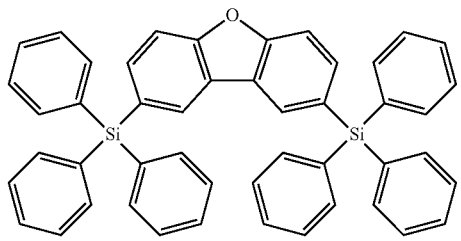 [SMILES: c1ccc([Si](c2ccccc2)(c2ccccc2)c2ccc3oc4ccc([Si](c5ccccc5)(c5ccccc5)c5ccccc5)cc4c3c2)cc1]

In a very particularly preferred embodiment, the present invention relates to an OLED which, as well as at least one metal-carbene complex of the general formula (I), comprises at least one compound of the general formula (X), in which case the compound of the formula (X) is most preferably at least one of the compounds specified below:

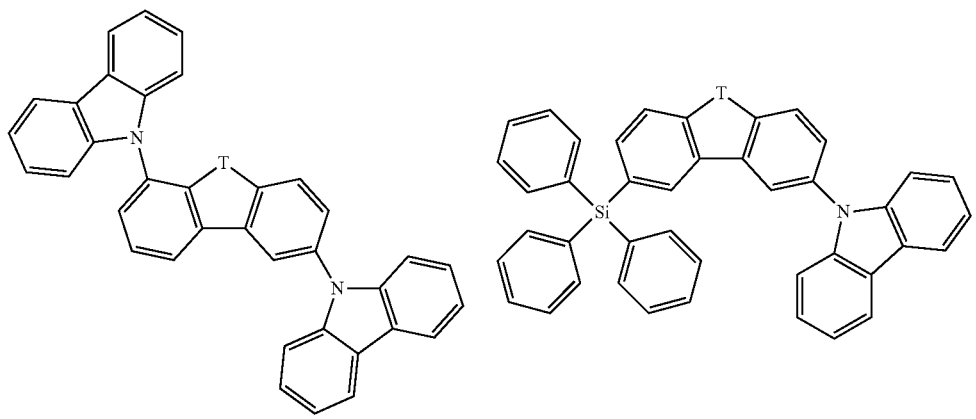

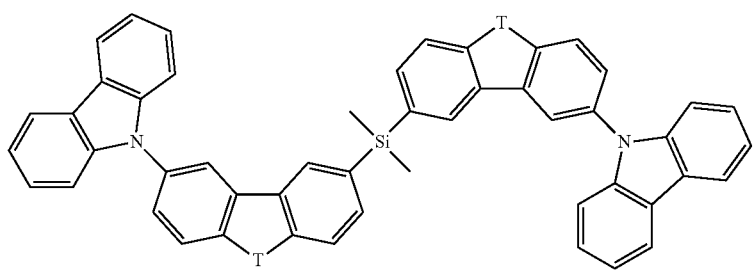

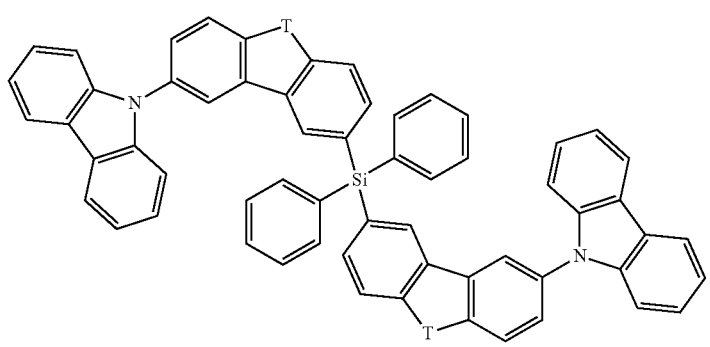

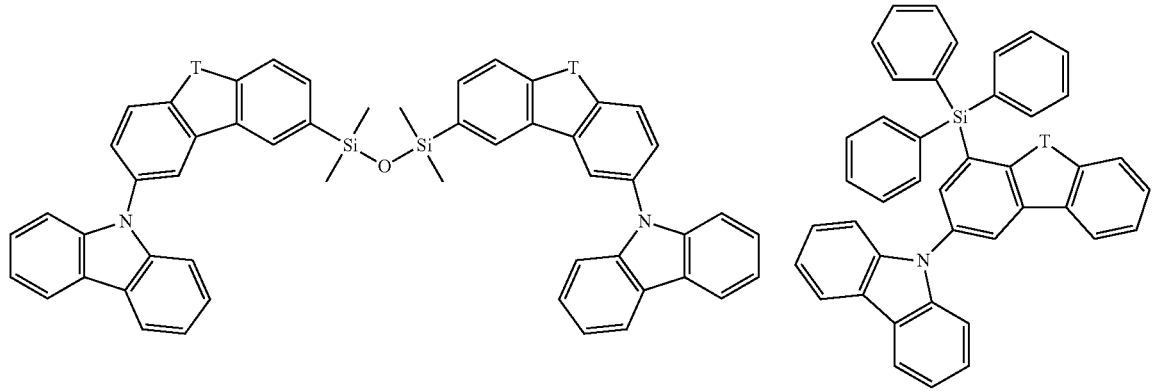
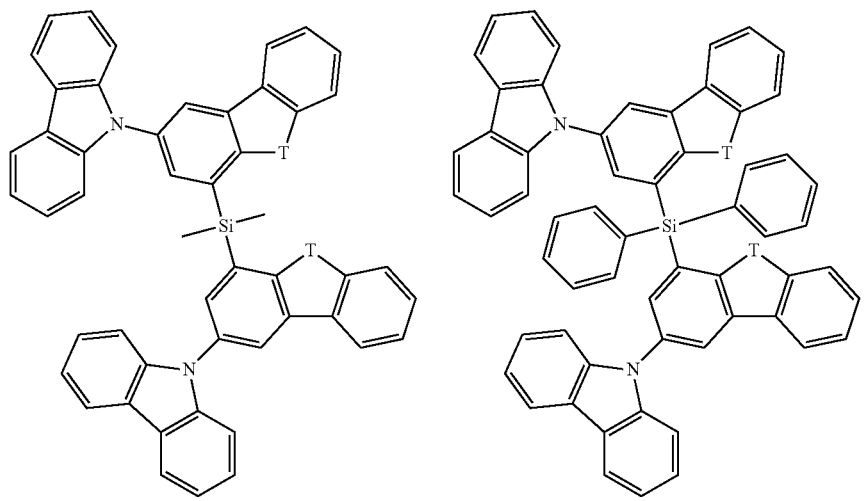
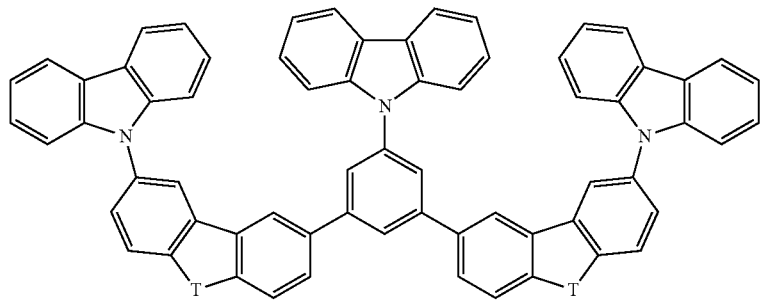
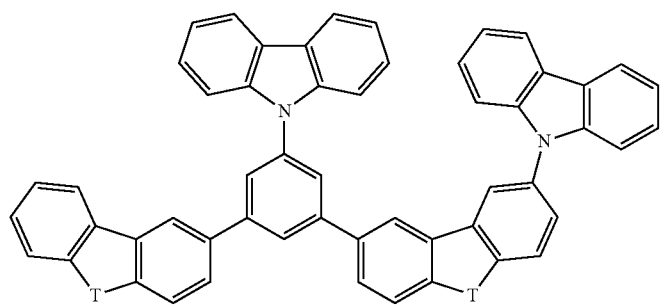

-continued
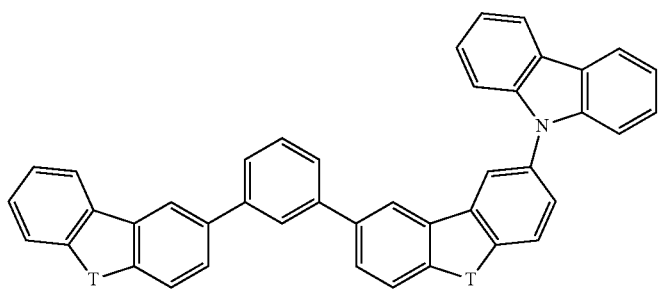
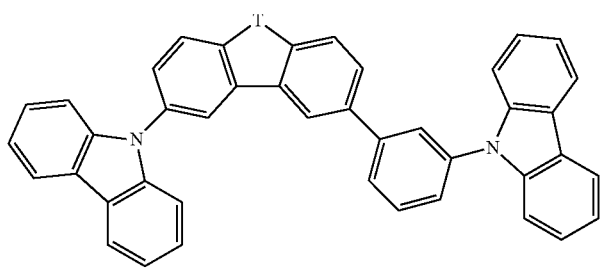
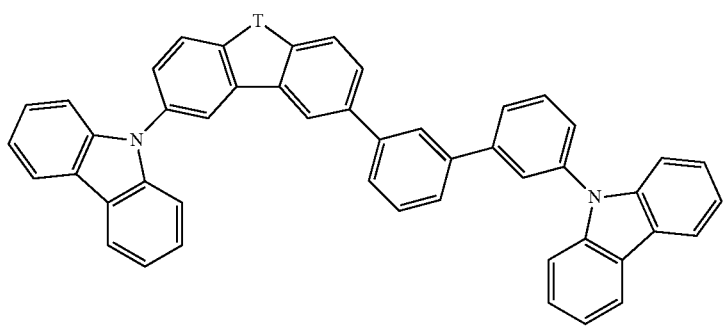
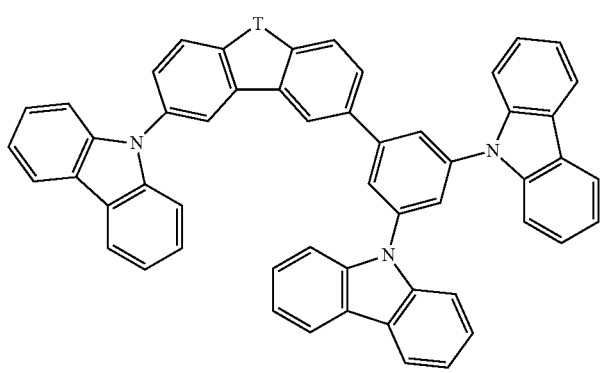
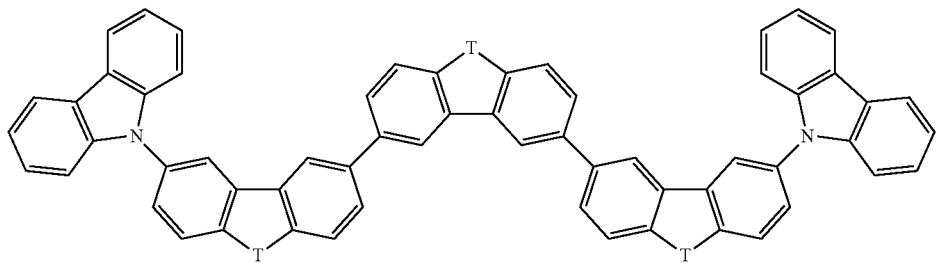

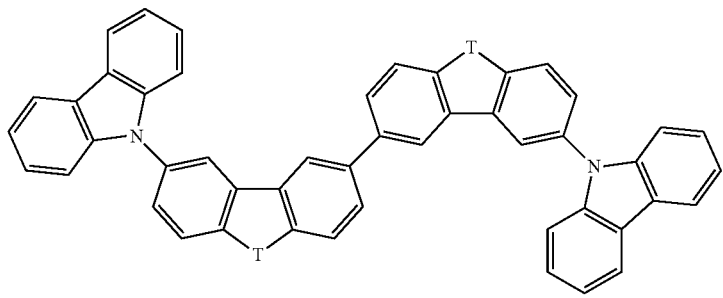
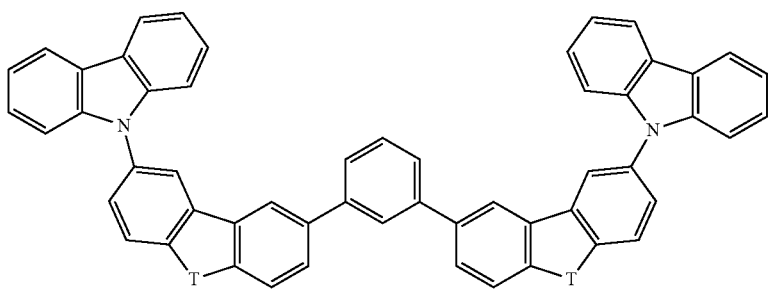
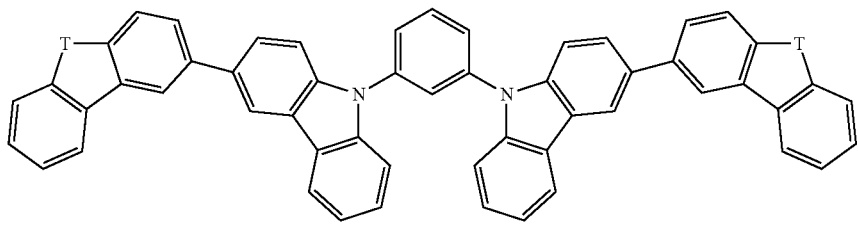
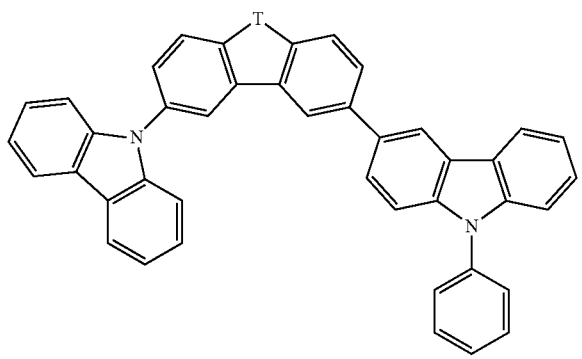
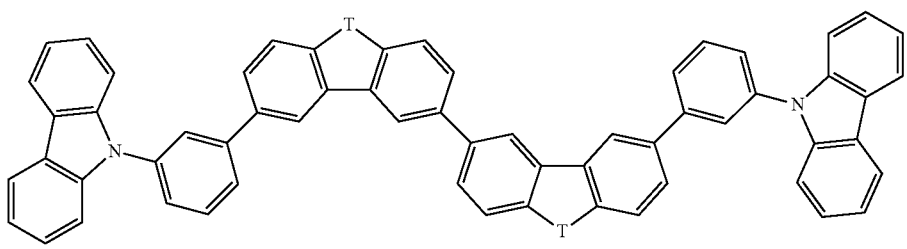

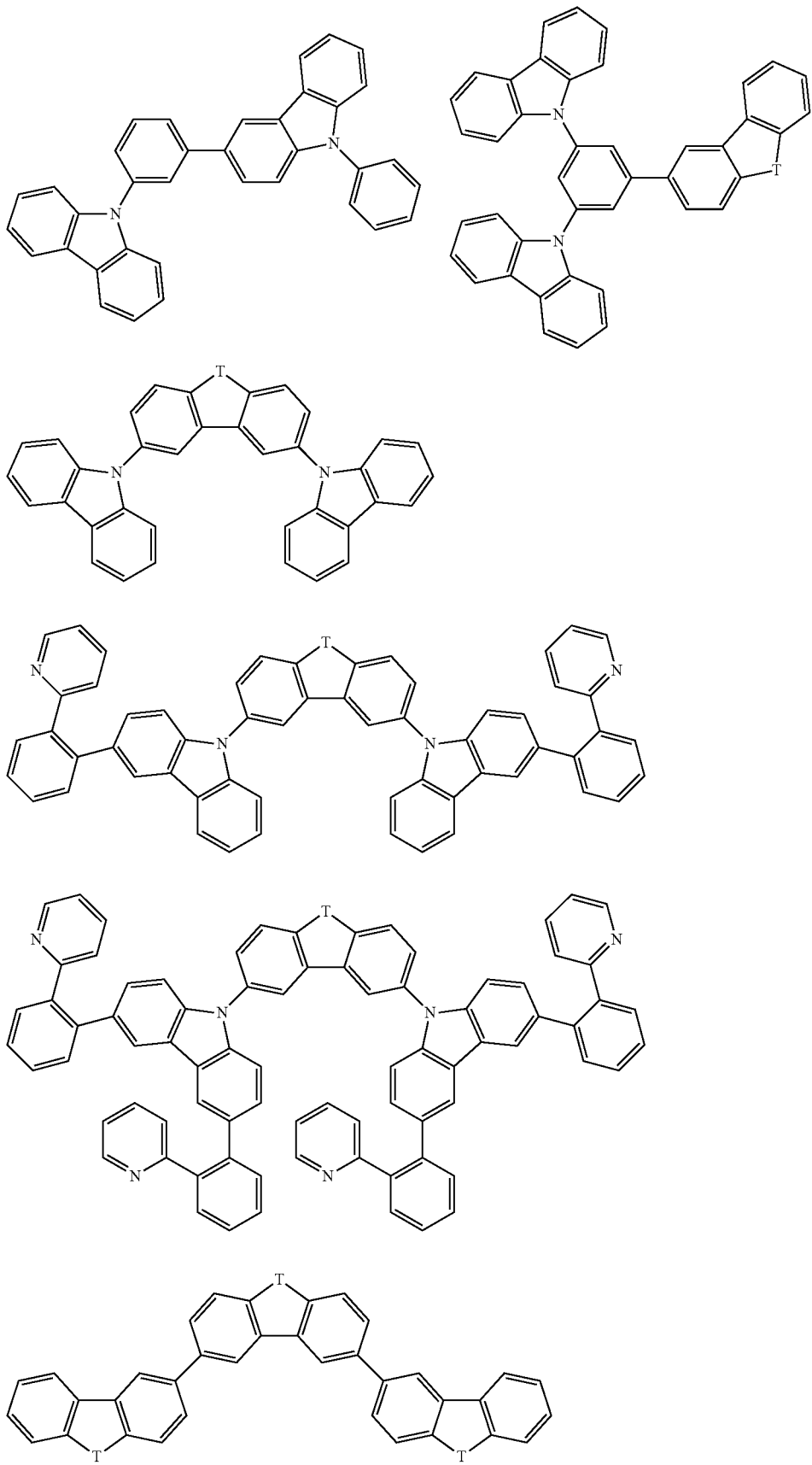

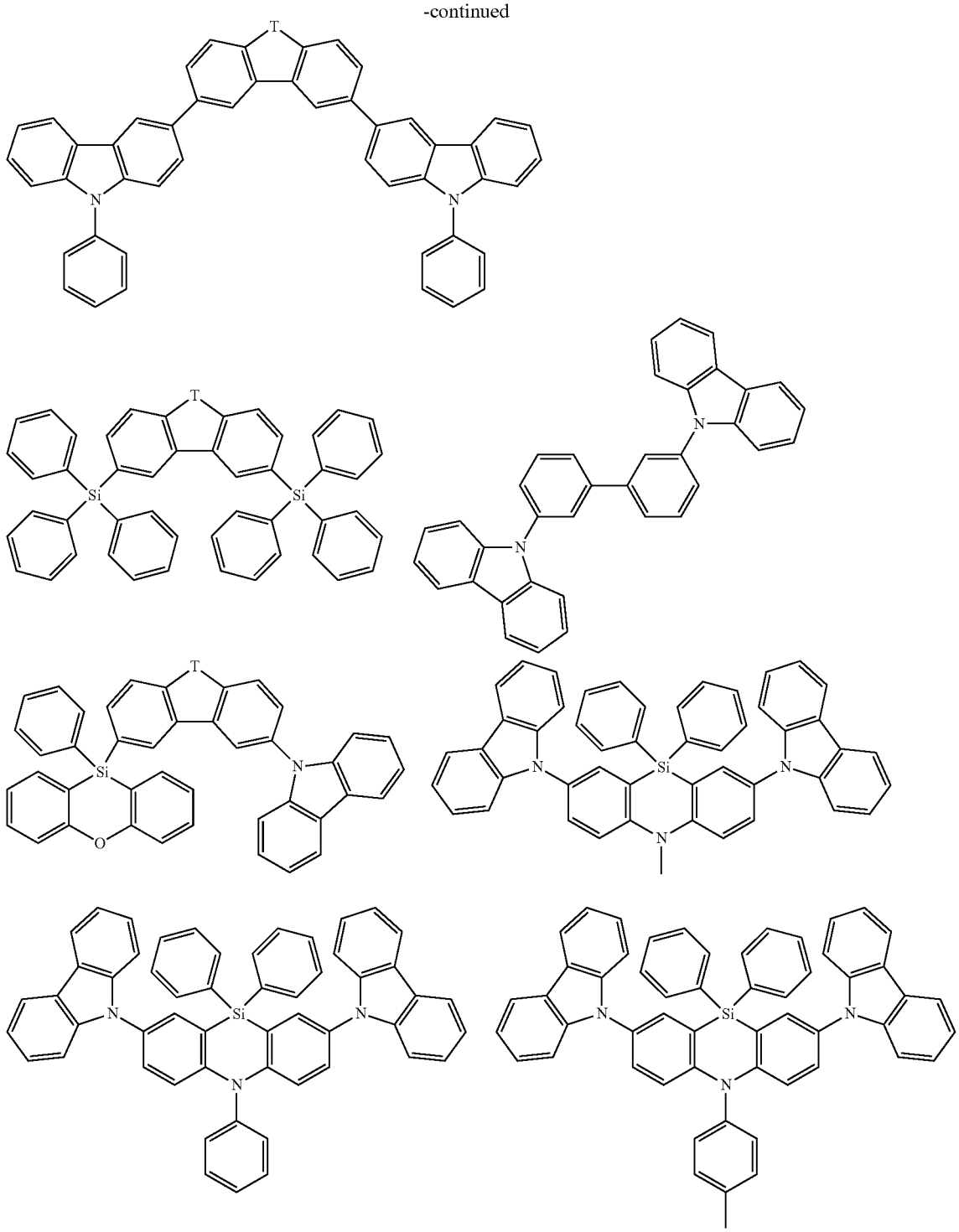

In the aforementioned compounds, T is O or S, preferably O. When more than one T occurs in the molecule, all T groups have the same definition.

In addition to the compounds of the formula (X), according to the present invention, it is also possible to use crosslinked or polymeric materials comprising repeat units based on the general formula (X) in crosslinked or polymerized form together with at least one metal-carbene complex of the general formula (I). Like the compounds of the general formula (X), the latter are preferably used as matrix materials.

The crosslinked or polymeric materials have outstanding solubility in organic solvents, excellent film-forming properties and relatively high glass transition temperatures. In addition, high charge carrier mobilities, high stabilities of color emission and long operating times of the corresponding components can be observed when crosslinked or polymeric materials according to the present invention are used in organic light-emitting diodes (OLEDs).

The crosslinked or polymerized materials are particularly suitable as coatings or in thin films since they are thermally and mechanically stable and relatively defect-free.

The crosslinked or polymerized materials comprising repeat units based on the general formula (X) can be prepared by a process comprising steps (a) and (b):

(a) preparation of a crosslinkable or polymerizable compound of the general formula (X) where at least one of the a" $R^{55}$ radicals or at least one of the b' $R^{56}$ radicals is a crosslinkable or polymerizable group attached via a spacer, and
(b) crosslinking or polymerization of the compound of the general formula (X) obtained from step (a).

The crosslinked or polymerized materials may be homopolymers, which means that exclusively units of the general formula (X) are present in crosslinked or polymerized form. They may also be copolymers, which means that further monomers are present in addition to the units of the general formula (X), for example monomers with hole-conducting and/or electron-conducting properties, in crosslinked or polymerized form.

In a further preferred embodiment of the inventive OLED, it comprises an emission layer comprising at least one inventive metal-carbene complex of the general formula (I), at least one matrix material of the formula (X), and optionally at least one further hole-transporting matrix material.

The inventive OLEDs can be used in all devices in which electroluminescence is useful. Suitable devices are preferably selected from stationary and mobile visual display units and illumination means. The present invention therefore also relates to a device selected from the group consisting of stationary visual display units and mobile visual display units and illumination means, comprising an inventive OLED.

Stationary visual display units are, for example, visual display units of computers, televisions, visual display units in printers, kitchen appliances and advertising panels, illuminations and information panels. Mobile visual display units are, for example, visual display units in cellphones, laptops, tablet PCs, digital cameras, mp-3 players, smartphones, vehicles, and destination displays on buses and trains.

The inventive metal-carbene complexes of the general formula (I) can additionally be used in OLEDs with inverse structure. In these inverse OLEDs, the inventive complexes are in turn preferably used in the light-emitting layer. The structure of inverse OLEDs and the materials typically used therein are known to those skilled in the art.

The present invention further provides a white OLED comprising at least one inventive metal-carbene complex of the general formula (I). In a preferred embodiment, the metal-carbene complex of the general formula (I) is used as emitter material in the white OLED. Preferred embodiments of the metal-carbene complex of the general formula (I) have been specified above. In addition to the at least one metal-carbene complex of the general formula (I), the white OLED may comprise (i) at least one compound of the formula (X). The compound of the formula (X) is preferably used as matrix material. Preferred compounds of the formula (X) have been specified above; and/or
(ii) at least one compound of the formula (VII) and/or (IX). The compounds of the formula (VII) and/or (IX) are preferably used as electron transport material. Preferred compounds of the formulae (VII) and (IX) have been specified above.

In order to obtain white light, the OLED must generate light which colors the entire visible range of the spectrum. However, organic emitters normally emit only in a limited portion of the visible spectrum—i.e. are colored. White light can be generated by the combination of different emitters. Typically, red, green and blue emitters are combined. However, the prior art also discloses other methods for formation of white OLEDs, for example the triplet harvesting approach. Suitable structures for white OLEDs or methods for formation of white OLEDs are known to those skilled in the art.

In one embodiment of a white OLED, several dyes are layered one on top of another in the light-emitting layer of an OLED and hence combined (layered device). This can be achieved by mixing all dyes or by direct series connection of different-colored layers. The expression "layered OLED" and suitable embodiments are known to those skilled in the art.

In general, the different layers then have the following thicknesses: anode (2) 500 to 5000 Å (ångström), preferably 1000 to 2000 Å; hole-transporting layer (3) 50 to 1000 Å, preferably 200 to 800 Å, either a light-emitting layer comprising a mixture of different emitters (4): 10 to 1000 Å, preferably 100 to 800 Å, or several light-emitting layers in succession, each individual layer comprising a different emitter (4a, b, c, . . . ): each 10 to 1000 Å, preferably each 50 to 600 Å, electron-transporting layer (5) 50 to 1000 Å, preferably 200 to 800 Å, cathode (6) 200 to 10 000 Å, preferably 300 to 5000 Å.

In a further embodiment of a white OLED, several different-colored OLEDs are stacked one on top of another (stacked device). For the stacking of two OLEDs, what is called a charge generation layer (CG layer) is used. This CG layer may be formed, for example, from one electrically n-doped and one electrically p-doped transport layer. The expression "stacked OLED" and suitable embodiments are known to those skilled in the art.

In general, the different layers then have the following thicknesses: anode (2) 500 to 5000 Å (ångström), preferably 1000 to 2000 Å; first hole-transporting layer (3) 50 to 1000 Å, preferably 200 to 800 Å, first light-emitting layer (4) 10 to 1000 Å, preferably 50 to 600 Å, first electron-transporting layer (5) 50 to 1000 Å, preferably 200 to 800 Å, electrically n-doped layer 50 to 1000 Å, preferably 100 to 800 Å, electrically p-doped layer 50 to 1000 Å, preferably 100 to 800 Å, second hole-transporting layer (3) to 50 to 1000 Å, preferably 200 to 800 Å, second light-emitting layer (4) 10 to 1000 Å, preferably 50 to 600 Å, second electron-transporting layer (5) 50 to 1000 Å, preferably 200 to 800 Å, electrically n-doped layer 50 to 1000 Å, preferably 100 to 800 Å, electrically p-doped layer 50 to 1000 Å, preferably 100 to 800 Å, third hole-transporting layer (3) to 1000 Å, preferably 200 to 800 Å, third light-emitting layer (4) 10 to 1000 Å, preferably 50 to 600 Å, third electron-transporting layer (5) to 50 to 1000 Å, preferably 200 to 800 Å, cathode (6) 200 to 10 000 Å, preferably 300 to 5000 Å.

In further embodiments of this "stacked device concept", it is also possible to stack only two OLEDs or to stack more than three OLEDs.

In a further embodiment of white OLEDs, the two concepts mentioned for white light generation can also be combined. For example, a single-color OLED (for example blue) can be stacked with a multicolor layered OLED (for example red-green). Further combinations of the two concepts are conceivable and known to those skilled in the art.

The inventive metal-carbene complex of the formula (I) can be used in any of the layers mentioned above in white OLEDs. In a preferred embodiment, it is used in one or more or all light-emitting layer(s) of the OLED(s), in which case the structure of the invention metal-carbene complex is varied as a function of the use of the complex. Suitable and preferred components for the further layers of the light OLED(s) or materials suitable as matrix material in the light-emitting layer(s) and preferred matrix materials are likewise specified above.

The present invention also relates to an organic electronic component, preferably an organic light-emitting diode (OLED), organic photovoltaic cell (OPV), organic field-effect transistor (OFET) or light-emitting electrochemical cell (LEEC), comprising at least one inventive metal-carbene complex of the general formula (I).

EXAMPLES

The examples which follow, more particularly the methods, materials, conditions, process parameters, apparatus and the like detailed in the examples, are intended to support the present invention, but not to restrict the scope of the present invention.

All experiments are carried out in protective gas atmosphere.

The percentages and ratios mentioned in the examples below—unless stated otherwise—are % by weight and weight ratios.

I Synthesis Examples

Example 1

2,3-Bis(phenylamino)pyridine (ZW1)

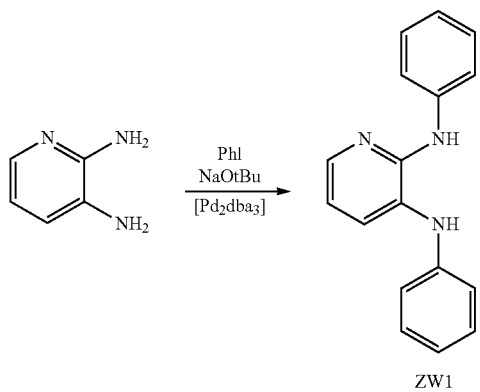 [SMILES: Nc1cccnc1N ; c1ccc(Nc2cccnc2Nc2ccccc2)cc1]

ZW1

A suspension of 2,3-diaminopyridine (8.9 g, 9 mmol) and iodobenzene (17.8 ml, 18 mmol) in dioxane (270 ml) is admixed with tris(dibenzylideneacetone)dipalladium ($Pd_2(dba)_3$, 3838 mg, 0.1 mmol), 9,9-dimethyl-4,5-bis(diphenylphosphin)xanthene (1.4 g, 0.3 mmol), sodium tert-butoxide (15.4 g, 18 mmol) and water (2.3 g). The mixture is stirred under reflux overnight. After cooling to room temperature, the precipitate is filtered off with suction and washed with dichloromethane. The combined filtrates are concentrated to dryness and the residue is dissolved in dichloromethane (125 ml) and cyclohexane (150 ml) and column-filtered. The product fractions are concentrated and precipitated product is filtered off. Yield: 14.2 g (67%).

$^1$H NMR ($CD_2Cl_2$, 500 MHz): δ=5.19 (br s, 1H), 6.71-6.76 (m, 3H), 6.84 (dd, 1H), 6.89-6.96 (m, 2H), 7.19 (dd, 2H), 7.23 (dd, 2H), 7.39 (d, 1H), 7.51 (d, 2H), 8.02 (d, 1H).

1,3-Diphenyl-4-azabenzimidazolium chloride

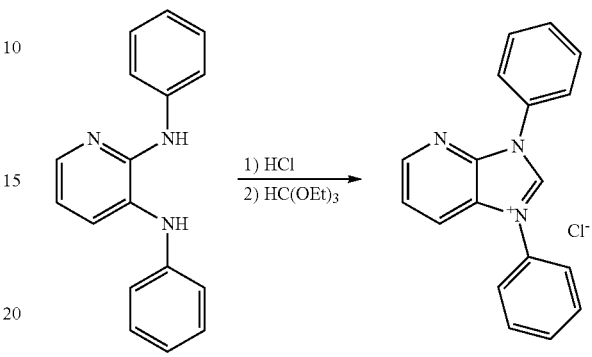

A suspension of 2,3-bis(N-phenylamino)pyridine (14.2 g, 54 mmol) in hydrochloric acid (200 ml) is stirred at room temperature overnight. The mixture is concentrated to dryness to obtain 14.0 g of a solid. Triethyl orthoformate (160 ml) is added thereto and the mixture is stirred at 105° C. overnight. After cooling to room temperature, the solid is filtered off with suction and washed with triethyl orthoformate. Yield: 10.3 g (62%).

$^1$H NMR ($CD_2Cl_2$, 500 MHz): δ=7.55-7.73 (m, 7H), 8.08 (dd, 2H), 8.19 (dd, 1H), 8.33 (dd, 2H), 8.80 (dd, 1H), 12.24 (s, 1H).

Complex fac-Em1

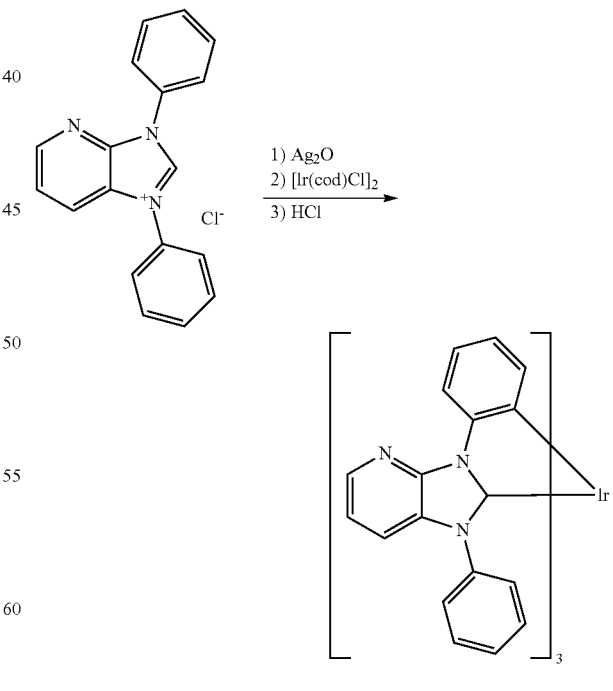

fac-Em1

A suspension of 1,3-diphenyl-4-azabenzimidazolium chloride (4.9 g, 16 mmol) and 3 Å molecular sieve (25 g) in dioxane (250 ml) is admixed with silver(I) oxide (3.0 g, 13 mmol) and stirred at room temperature overnight. The mixture is admixed with chloro(1,5-cyclooctadien)iridium(I) dimer (1.1 g, 1.6 mmol) and stirred under reflux overnight. After cooling to room temperature, the precipitate is filtered off with suction and washed with dichloromethane. The combined filtrates are concentrated to dryness and the residue is purified by column filtration (silica gel, dichloromethane). The resulting solid is dissolved in butanone (110 ml) and admixed with hydrochloric acid (1N, 11.8 ml). The mixture is stirred under reflux for 24 hours. After cooling to room temperature, the precipitate is filtered off with suction, washed with cyclohexane and purified by column chromatography (silica gel, 2:3 dichloromethane/cyclohexane). Yield: 1.02 g (31%).

$^1$H NMR (CD$_2$Cl$_2$, 500 MHz): δ=6.24 (d, 6H), 6.50 (d, 3H), 6.58 (dd, 3H), 6.68-6.79 (m, 9H), 6.96 (dd, 3H), 7.06 (mc, 3H), 7.27 (dd, 3H), 8.32 (dd, 3H), 8.89 (dd, 3H).

Photoluminescence (2% in a PMMA film):
$\lambda_{max}$=415 nm, CIE: (0.16; 0.07); QY=41%

Example 2

2-Chloro-3-N-isopropylaminopyridine

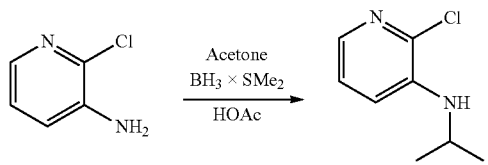

A solution of 3-amino-2-chloropyridine (16.0 g, 124 mmol) in dichloromethane (300 ml) and glacial acetic acid (150 ml) is admixed with acetone (25.0 ml, 335 mmol) and, at 0° C., with borane-dimethyl sulfide complex (13.0 ml, 136 mmol), and the mixture is stirred at room temperature overnight. The solution is adjusted to pH 8 with ammonia (25% in water) and diluted with water (100 ml). The organic phase is removed and the aqueous phase is extracted with dichloromethane (3×100 ml). The combined organic phases are dried over sodium sulfate and concentrated to dryness. The crude product is used without further purification. Yield: 21.4 g (>100%).

$^1$H NMR (d$_6$-DMSO, 500 MHz): δ=1.19 (d, 6H), 3.66 (mc, 1H), 4.98 (d, 1H), 7.09 (dd, 1H), 7.19 (dd, 1H), 7.59 (dd, 1H).

2-N-Phenylamino-3-N-isopropylaminopyridine

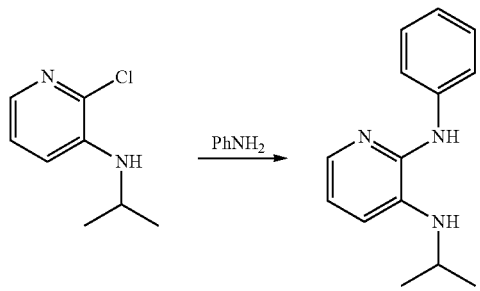

A mixture of 2-chloro-3-N-isopropylaminopyridine (21.4 g, 125 mmol) in aniline (11.4 ml, 125 mmol) is stirred at 170° C. overnight. After cooling to room temperature, the solid is taken up in water (100 ml) and the solution is adjusted to pH 11 with sodium hydroxide solution (1N). The aqueous phase is extracted with dichloromethane (1×100 ml, 2×50 ml). The combined organic phases are concentrated to dryness and the crude product is purified by column chromatography (silica gel, ethyl acetate/n-hexane gradient). Yield: 15.8 g (56%).

$^1$H NMR (d$_6$-DMSO, 500 MHz): δ=1.19 (d, 6H), 3.59 (mc, 1H), 4.91 (d, 1H), 6.70 (dd, 1H), 6.76-6.88 (m, 2H), 7.22 (mc, 2H), 7.46 (dd, 1H), 7.54 (d, 2H), 7.76 (br s, 1H).

1-Isopropyl-3-phenyl-4-azabenzimidazolium Iodide

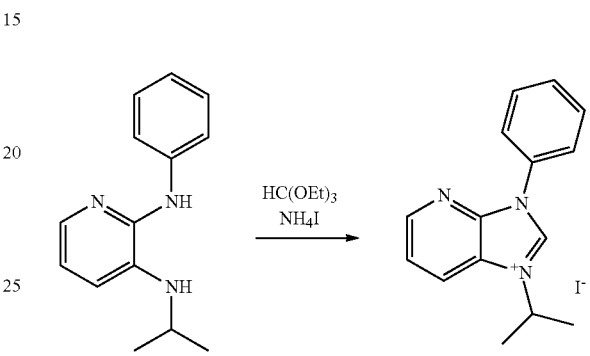

A mixture of 2-N-phenylamino-3-N-isopropylaminopyridine (5.0 g, 21 mmol) and triethyl orthoformate (20 ml) is admixed with ammonium iodide (3.2 g, 22 mmol) and stirred at 70° C. overnight. After cooling to room temperature, the solid is filtered off with suction and washed with petroleum ether and a little dichloromethane. Yield: 6.6 g (89%).

$^1$H NMR (CD$_2$Cl$_2$, 500 MHz): δ=1.90 (d, 6H), 5.43 (sept, 1H), 7.56-7.72 (m, 4H), 8.15 (mc, 2H), 8.28 (dd, 1H), 8.77 (dd, 1H), 11.19 (s, 1H).

Complex mer-Em2

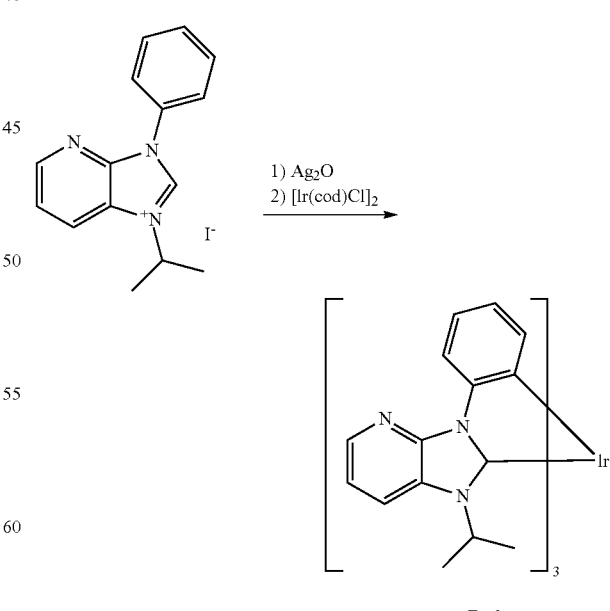

mer-Em2

A suspension of 1-isopropyl-3-phenyl-4-azabenzimidazolium iodide (4.5 g, 16 mmol) and 3 Å molecular sieve (55 g)

in dioxane (380 ml) is admixed with silver(I) oxide (3.1 g, 13 mmol) and stirred at room temperature overnight. The mixture is admixed with a solution of chloro-(1,5-cyclooctadiene)iridium(I) dimer (1.1 g, 1.6 mmol) in o-xylene (500 ml) and stirred at 110° C. overnight. After cooling to room temperature, the precipitate is filtered off with suction and stirred with ethyl acetate (400 ml) and dichloromethane (400 ml). The combined filtrates are concentrated to dryness and the residue is column-filtered (silica gel, dichloromethane). The product fractions are concentrated to dryness and stirred with methyl tert-butyl ether. Yield: 2.1 g (72%).

$^1$H NMR (CD$_2$Cl$_2$, 500 MHz): δ=0.59 (d, 3H), 0.66 (d, 3H), 0.80 (d, 3H), 1.24 (d, 3H), 1.30 (d, 3H), 1.60 (d, 3H), 4.61 (mc, 2H), 4.80 (sept, 1H), 6.56 (dd, 1H), 6.61-6.70 (m, 4H), 6.91-7.03 (m, 4H), 7.10-7.18 (m, 3H), 7.67-7.74 (m, 3H), 8.33-8.40 (m, 3H), 8.78 (d, 1H), 8.81 (d, 1H), 8.85 (dd, 1H).

Photoluminescence (2% in a PMMA film):
$\lambda_{max}$=441 nm, CIE: (0.16; 0.11); QY=82%

Complex fac-Em2

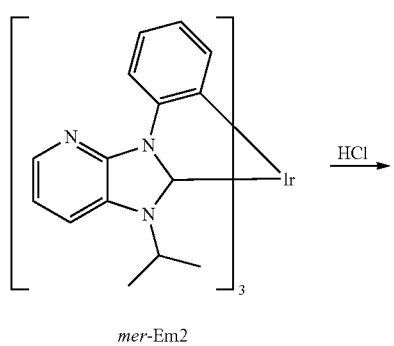

mer-Em2

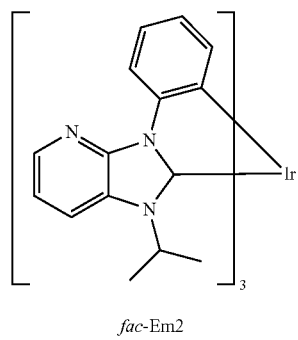

fac-Em2

A solution of mer-Em2 (500 mg, 0.6 mmol) in methanol (50 ml) is admixed with hydrochloric acid (1N, 5 ml) and stirred under reflux overnight. After cooling to room temperature, the precipitate is filtered off with suction, washed with petroleum ether and stirred with methyl tert-butyl ether overnight. Yield: 338 mg (68%).

$^1$H NMR (CD$_2$Cl$_2$, 500 MHz): δ=0.77 (d, 9H), 1.51 (d, 9H), 4.66 (sept, 3H), 6.37 (d, 3H), 6.58 (dd, 3H), 6.97 (dd, 3H), 7.10 (dd, 3H), 7.66 (d, 3H), 8.34 (d, 3H), 8.78 (d, 3H).

Photoluminescence (2% in a PMMA film):
$\lambda_{max}$=418 nm, CIE: (0.16; 0.05); QY=77%

Example 3

2-N-(2''-methylbiphen-3'-yl)amino-3-N-isopropylaminopyridine

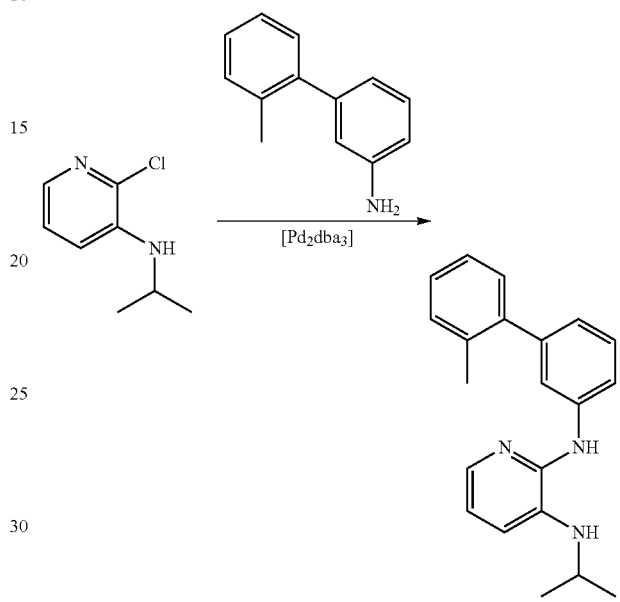

A solution of 2-chloro-3-N-isopropylaminopyridine (3.5 g, 20 mmol) and 2'-methylbiphen-3-ylamine hydrochloride (4.9 g, 23 mmol) in toluene (65 ml) is admixed with tris(dibenzylideneacetone)dipalladium (281 mg, 0.3 mmol), rac-BINAP (585 mg, 0.9 mmol) and sodium tert-butoxide (5.1 g, 51 mmol). The mixture is stirred under reflux overnight. After cooling to room temperature, the precipitate is filtered off with suction and the filtrate is concentrated to dryness. The residue is purified by column chromatography (silica gel, 10:1 toluene/ethyl acetate). Yield: 6.1 g (93%), contaminated with approx. 30% 2'-methylbiphen-3-ylamine.

$^1$H NMR (CD$_2$Cl$_2$, 500 MHz): δ=1.21 (d, 6H), 3.26 (br s, 1H), 3.56 (mc, 1H), 6.31 (br s, 1H), 6.82 (dd, 1H), 6.89 (mc, 1H), 6.97 (dd, 1H), 7.20-7.34 (m, 7H), 7.70 (dd, 1H).

1-Isopropyl-3-(2''-methylbiphen-3'-yl)-4-azabenzimidazolium Iodide

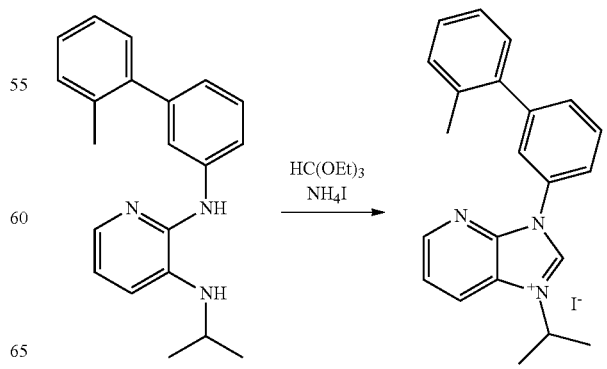

A mixture of 2-N-(2″-methylbiphen-3′-yl)amino-3-N-isopropylaminopyridine (2.0 g, 6.3 mmol) in triethyl orthoformate (8 ml) is admixed with ammonium iodide (281 mg, 6.6 mmol) and stirred at 80° C. overnight. After cooling to room temperature, the mixture is diluted with triethyl orthoformate (5 ml) and isopropanol (3.5 ml) and stirred at room temperature overnight. The precipitate is filtered off with suction and washed with n-hexane. Yield: 2.0 g (70%).

¹H NMR (d₆-DMSO, 500 MHz): δ=1.94 (d, 6H), 5.50 (sept, 1H), 7.24-7.34 (m, 3H), 7.39 (dd, 1H), 7.60 (mc, 1H), 7.70-7.78 (m, 2H), 8.09 (dd, 1H), 8.21 (mc, 1H), 8.40 (dd, 1H), 8.81 (dd, 1H), 11.21 (s, 1H).

Complex mer-Em3

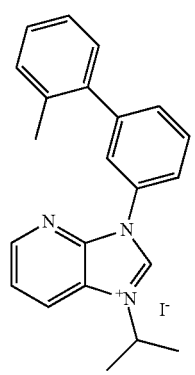

1) Ag₂O
2) [Ir(cod)Cl]₂

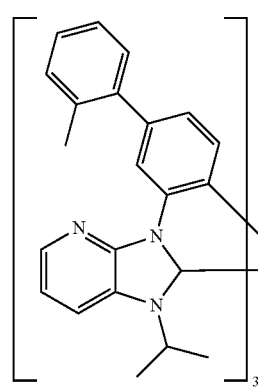

*mer*-Em3

A suspension of 1-isopropyl-3-(2″-methylbiphen-3′-yl)-4-azabenzimidazolium iodide (400 mg, 0.9 mmol) and 3 Å molecular sieve (2 g) in dioxane (15 ml) is admixed with silver(I) oxide (163 mg, 0.7 mmol) and stirred at room temperature overnight. The mixture is admixed with chloro(1,5-cyclooctadiene)indium(I) dimer (57 mg, 0.08 mmol) and stirred under reflux for three days. After cooling to room temperature, the mixture is diluted with dichloromethane (15 ml), and the precipitate is filtered off with suction and washed with dichloromethane. The combined filtrates are concentrated to dryness and the residue is purified by column chromatography (silica gel, 9:1→4:1 toluene/ethyl acetate). Yield: 176 mg (89%).

¹H NMR (CD₂Cl₂, 500 MHz): δ=0.70 (d, 3H), 0.77 (d, 3H), 0.90 (d, 3H), 1.39 (dd, 6H), 1.70 (d, 3H), 2.31 (s, 3H), 2.39 (s, 3H), 2.42 (s, 3H), 4.77 (mc, 2H), 4.91 (sept, 1H), 6.70-6.80 (m, 4H), 6.87 (d, 1H), 7.11-7.31 (m, 14H), 7.33-7.39 (m, 2H), 7.77 (mc, 3H), 8.34-8.40 (m, 3H), 8.93 (dd, 2H), 8.99 (d, 1H).

Photoluminescence (2% in a PMMA film):
$\lambda_{max}$=450 nm, CIE: (0.16; 0.14); QY=66%

Complex fac-Em3

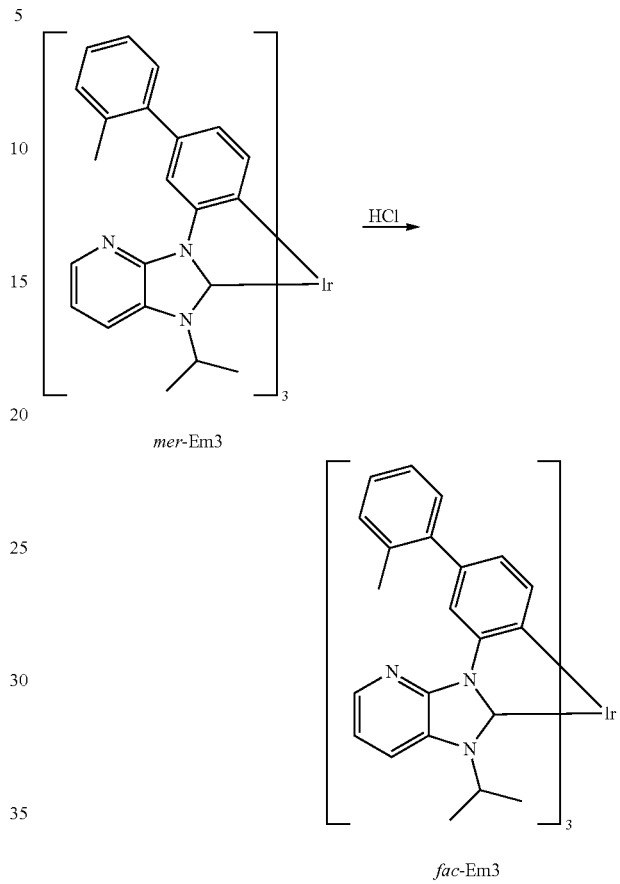

*mer*-Em3

HCl

*fac*-Em3

A solution of mer-Em3 (127 mg, 0.1 mmol) in butanone (15 ml) is admixed with hydrochloric acid (1N, 1.5 ml) and stirred under reflux overnight. After cooling to room temperature, the mixture is diluted with dichloromethane. The organic phase is washed with water and concentrated to dryness. The residue is purified by column chromatography (silica gel, 8:1 toluene/ethyl acetate). Yield: 50 mg (39%).

¹H NMR (CD₂Cl₂, 500 MHz): δ=0.87 (d, 9H), 1.55 (d, 9H), 2.27 (s, 9H), 4.72 (sept, 3H), 6.59 (d, 3H), 6.65 (dd, 3H), 7.08-7.28 (m, 15H), 7.69 (dd, 3H), 8.29 (dd, 3H), 8.86 (d, 3H).

Photoluminescence (2% in a PMMA film):
$\lambda_{max}$=437 nm, CIE: (0.16; 0.12); QY=65%

Example 4

2,6-Dichloro-3-N-isopropylaminopyridine

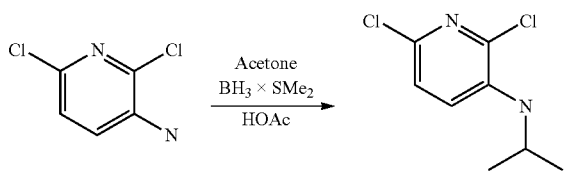

Acetone
BH₃ × SMe₂
HOAc

A solution of 2,6-dichloro-3-aminopyridine (10.0 g, 61 mmol) in dichloromethane (200 ml) and glacial acetic acid (100 ml) is admixed with acetone (12.0 ml, 166 mmol) and, at 0° C., with borane-dimethyl sulfide complex (6.4 ml, 68 mmol), and the mixture is stirred at room temperature for three hours. The solution is adjusted to pH 9 with ammonia (25% in water, 150 ml). The organic phase is removed and the aqueous phase is extracted with dichloromethane (2×100 ml). The combined organic phases are concentrated to dryness and the residue is column-filtered (silica gel, 1:1 dichloromethane/cyclohexane). Yield: 11.7 g (93%).

$^1$H NMR (CD$_2$Cl$_2$, 500 MHz): δ=1.24 (d, 6H), 3.60 (mc, 1H), 4.20 (br s, 1H), 6.90 (d, 1H), 7.11 (d, 1H).

2-N-Phenylamino-3-N-isopropylamino-6-chloropyridine (ZW2)

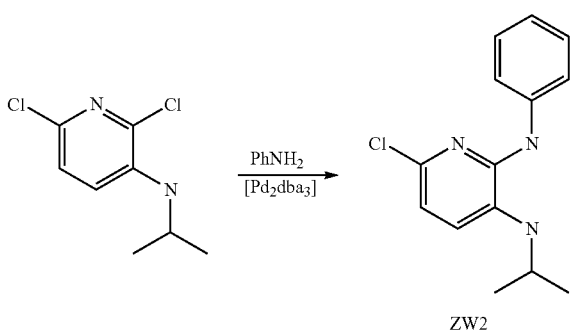

ZW2

A solution of 2,6-dichloro-3-N-isopropylaminopyridine (23.2 g, 113 mmol) and aniline (11.0 ml, 121 mmol) in toluene (500 ml) is admixed with tris(dibenzylideneacetone)-dipalladium (1.6 g, 1.7 mmol), rac-BINAP (3.2 g, 5.1 mmol) and sodium tert-butoxide (15.2 g, 158 mmol). The mixture is stirred under reflux for 24 hours and, after cooling to room temperature, concentrated to dryness. The residue is purified by column chromatography (silica gel, 3:7 dichloromethane/cyclohexane→dichloromethane). Yield: 19.2 g (65%).

$^1$H NMR (CD$_2$Cl$_2$, 500 MHz): δ=1.16 (d, 6H), 3.00 (br s, 1H), 3.46 (mc, 1H), 6.44 (br s, 1H), 6.73 (d, 1H), 6.90 (d, 1H), 6.95 (mc, 1H), 7.22-7.35 (m, 4H).

2-N-Phenylamino-3-N-isopropylamino-6-(2'-methylphenyl)pyridine

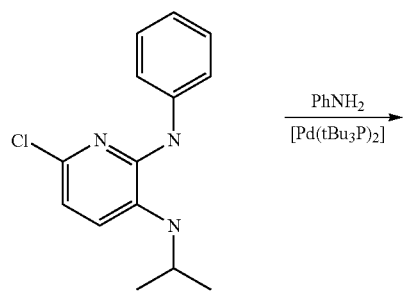

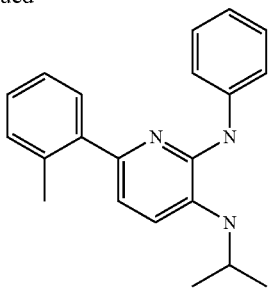

A solution of 2-N-phenylamino-3-N-isopropylamino-6-chloropyridine (5.0 g, 19 mmol) and 2-methylphenylboronic acid (3.1 g, 23 mmol) in dioxane (40 ml) is admixed with bis(tri-tert-butylphosphino)palladium (324 mg, 0.7 mmol) and sodium hydroxide solution (5N, 11.5 mmol), and the mixture is stirred at 85° C. overnight. The mixture is diluted with dichloromethane and washed with water. The organic phase is removed and concentrated to dryness. The residue is purified by column chromatography (silica gel, dichloromethane). Yield: 5.6 g (92%).

$^1$H NMR (CD$_2$Cl$_2$, 500 MHz): δ=1.23 (d, 6H), 2.37 (s, 3H), 3.60 (sept, 1H), 6.39 (br s, 1H), 6.90 (dd, 1H), 6.93 (d, 1H), 7.04 (d, 1H), 7.16-7.27 (m, 5H), 7.31-7.39 (m, 3H).

1-Isopropyl-3-phenyl-5-(2'-methylphenyl)-4-azabenzimidazolium Iodide

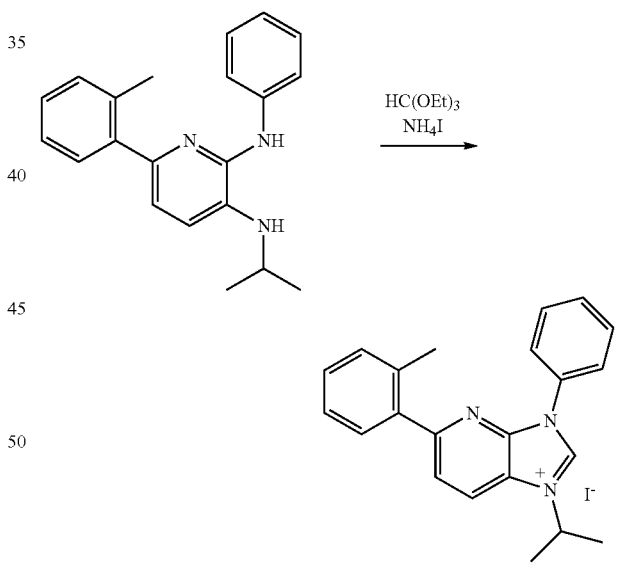

A mixture of 2-N-phenylamino-3-N-isopropylamino-6-(2'-methylphenyl)pyridine (6.5 g, 21 mmol) in triethyl orthoformate (10 ml) is admixed with ammonium iodide (5.9 mg, 41 mmol) and stirred at 80° C. overnight. After cooling to room temperature, the mixture is concentrated to dryness and the residue is taken up in dichloromethane (50 ml). The precipitate is filtered off and washed with dichloromethane. The filtrate is added to methyl tert-butyl ether. The precipitate is filtered off with suction, washed with methyl tert-butyl ether and dried in a vacuum drying cabinet at 70° C. Yield: 8.6 g (92%).

¹H NMR (d₆-DMSO, 500 MHz): δ=1.72 (d, 6H), 2.35 (s, 3H), 5.20 (sept, 1H), 7.29-7.41 (m, 3H), 7.48 (d, 1H), 7.64 (mc, 1H), 7.71 (mc, 2H), 7.95 (mc, 2H), 8.00 (d, 1H), 8.84 (d, 1H), 10.42 (s, 1H).

Complex mer-Em4

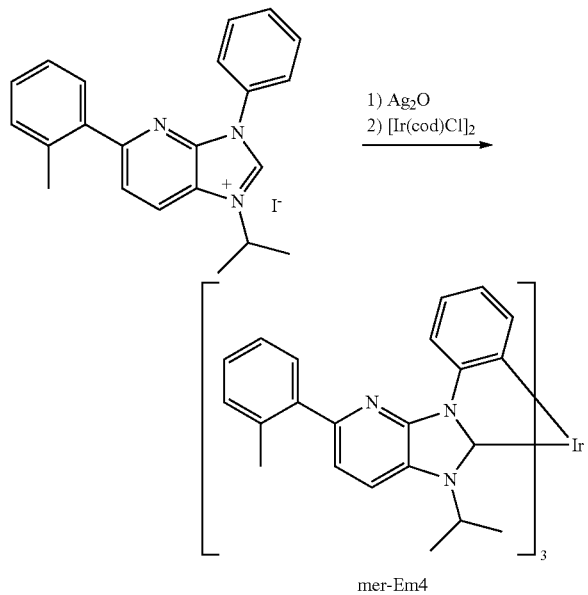

A suspension of 1-isopropyl-3-phenyl-5-(2'-methylphenyl)-4-azabenzimidazolium iodide (330 mg, 0.7 mmol) and 3 Å molecular sieve (2 g) in dioxane (10 ml) is admixed with silver(I) oxide (167 mg, 0.7 mmol) and stirred at room temperature overnight. The mixture is admixed with chloro(1,5-cyclooctadiene)iridium(I) dimer (49 mg, 0.07 mmol) and stirred under reflux overnight. After cooling to room temperature, the precipitate is filtered off with suction and washed with dichloromethane. The combined filtrates are concentrated to dryness and the residue is purified by column chromatography (silica gel, cyclohexane→ethyl acetate). Yield: 80 mg (47%).

¹H NMR (CD₂Cl₂, 500 MHz): δ=0.69 (d, 3H), 0.76 (d, 3H), 0.91 (d, 3H), 1.31 (d, 3H), 1.37 (d, 3H), 1.69 (d, 3H), 2.48 (s, 3H), 2.52 (s, 6H), 4.68 (sept, 1H), 4.74 (sept, 1H), 4.86 (sept, 1H), 6.64-6.77 (m, 5H), 6.91-7.03 (m, 3H), 7.08 (dd, 1H), 7.26-7.38 (m, 12H), 7.49-7.56 (m, 3H), 7.76-7.82 (m, 3H), 8.83 (d, 1H), 8.87 (d, 1H), 8.91 (d, 1H).

Photoluminescence (2% in a PMMA film):
$\lambda_{max}$=457 nm, CIE: (0.16; 0.16); QY=81%

Complex fac-Em4

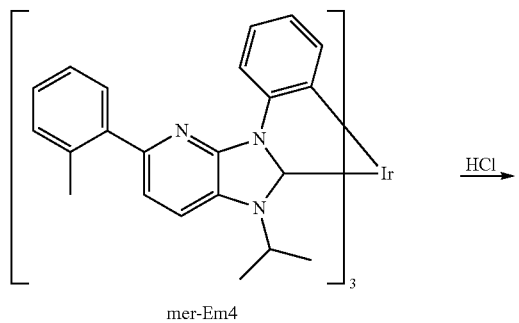

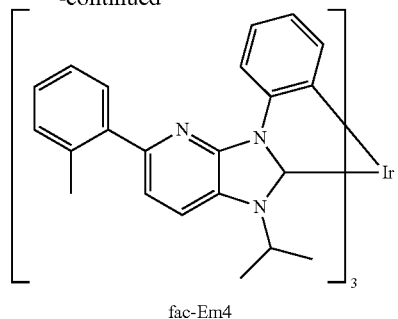

A solution of mer-Em4 (100 mg, 0.09 mmol) in methanol (10 ml) is admixed with hydrochloric acid (1N, 1 ml) and stirred under reflux overnight. After cooling to room temperature, the precipitate is filtered off with suction and washed with methanol. The solid is stirred with cyclohexane, filtered off with suction and dried in a vacuum drying cabinet at 70° C. Yield: 80 mg (80%).

¹H NMR (CD₂Cl₂, 500 MHz): δ=0.87 (d, 9H), 1.59 (d, 9H), 2.50 (s, 9H), 4.72 (sept, 3H), 6.43 (dd, 3H), 6.61 (mc, 3H), 6.95 (mc, 3H), 7.24-7.35 (m, 12H), 7.51 (dd, 3H), 7.73 (d, 3H), 8.82 (dd, 3H).

Photoluminescence (2% in a PMMA film):
$\lambda_{max}$=459 nm, CIE: (0.17; 0.19); QY=76%

Example 5

2-N-Phenylamino-3-N-isopropylamino-6-(2',6'-dimethylphenyl)pyridine

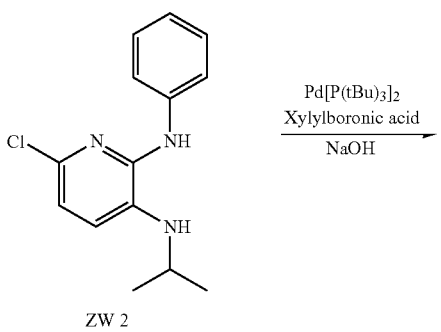

A solution of 2-N-phenylamino-3-N-isopropylamino-6-chloropyridine ZW2 (1.46 g, 5.58 mmol, for preparation see ZW2, Example 4) in dioxane (90 ml) is admixed with sodium hydroxide solution (50% in H₂O, 0.90 ml, 1.34 g, 16.8 mmol, 3.0 eq) and degassed, admixed with bis(tri-tert-butylphosphino)palladium (100 mg, 0.19 mmol, 3.5 mol %) and 2,6-dimethylphenylboronic acid (1.01 g, 6.70 mmol, 1.2 eq) and refluxed for 18 h. The solvent is removed, and the mixture is taken up with dichloromethane and washed with water. The organic phase is removed and concentrated to dryness. The residue is purified by column chromatography (silica gel, CH:EA=4:1). Yield: 1.15 g (62%).

$^1$H NMR (CD$_2$Cl$_2$, 500 MHz): δ=1.26 (d, J=6 Hz, 6H), 2.09 (s, 6H), 3.24 (br.s., 1H), 3.61 (sept., J=6 Hz, 1H), 6.37 (br. s, 1H), 6.73 (d, J=8 Hz, 1H), 6.89 (t, J=7 Hz, 1H), 7.07 (m$_c$, 3H), 7.12 (dd, J=7 Hz, J=9 Hz, 1H), 7.23 (m$_c$, 2 H), 7.27-7.29 (m, 2H).

1-Isopropyl-3-phenyl-5-(2',6'-dimethylphenyl)-4-azabenzimidazolium Iodide

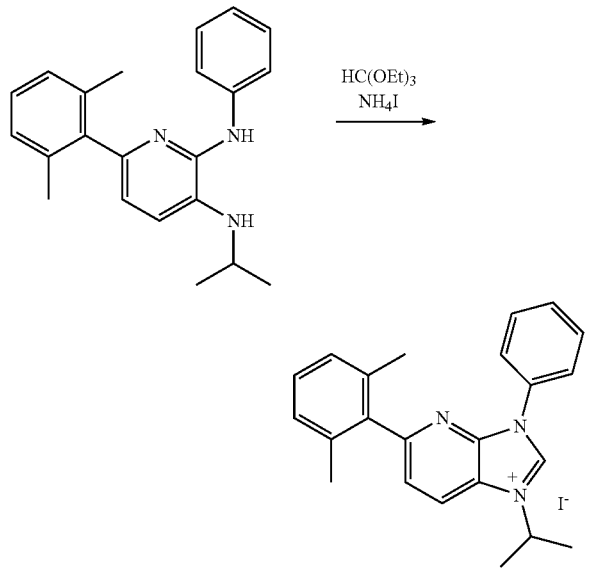

A mixture of 2-N-phenylamino-3-N-isopropylamino-6-(2',6'-dimethylphenyl)pyridine (0.95 g, 2.87 mmol) in triethyl orthoformate (25 ml) is admixed with ammonium iodide (1.86 g, 12.9 mmol, 4.5 eq) and refluxed for 18 h. After cooling, the precipitate formed is filtered off and washed with petroleum ether, and then dried. Yield: 1.12 g (83%).

$^1$H NMR (CD$_2$Cl$_2$, 500 MHz): δ=2.00 (d, J=7 Hz, 6H), 2.05 (s, 6H), 5.55 (sept., J=7 Hz, 1H), 7.16 (br. d, J=7 Hz, 2H), 7.26-7.29 (m, 1H), 7.58-7.62 (m, 1H), 7.64-7.68 (m, 3H), 8.19 (d, J=8 Hz, 2H), 8.38 (d, J=9 Hz, 1H), 11.30 (s, 1H).

Complex mer-Em5

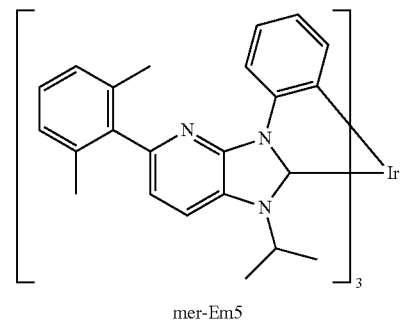

mer-Em5

1-Isopropyl-3-phenyl-5-(2',6'-dimethylphenyl)-4-azabenzimidazolium iodide (1.12 g, 2.38 mmol) is initially charged in acetonitrile (120 ml) and admixed with silver(I) oxide (276 mg, 1.19 mmol), and stirred at 50° C. for 18 h. The solvent is removed and o-xylene (120 ml) is added. The mixture is admixed with chloro(1,5-cyclooctadiene)-iridium(I) dimer (160 mg, 0.238 mmol) and stirred at 135° C. for 65 h. After cooling, the solvent is removed, and the residue is taken up with ethyl acetate and washed with water. The organic phase is dried and concentrated, and the residue is purified by column chromatography (silica gel, cyclohexane:ethyl acetate=4:1). Yield: 570 mg (quant.).

$^1$H NMR (CD$_2$Cl$_2$, 500 MHz): δ=0.66 (d, 3H), 0.72 (d, 3H), 0.93 (d, 3H), 1.33 (d, 3H), 1.38 (d, 3H), 1.72 (d, 3H), 2.05 (br.s, 6H), 2.15 (s, 9H), 2.22 (br.s, 3H), 4.67 (sept, 1H), 4.81 (sept, 1H), 4.83 (sept, 1H), 6.66-6.82 (m, 5H), 6.90-9.97 (m, 3H), 7.06-7.18 (m, 10H), 7.22-7.27 (m, 3H), 7.79 (d, 3H), 8.75 (d, 1H), 8.80 (d, 1H), 8.83 (d, 1H).

MS (Maldi):

m/e=1211 (M)$^+$

Photoluminescence (2% in a PMMA film):

λ$_{max}$=444 nm, CIE: (0.16; 0.11); QY=86%

Example 6

2-N-Phenylamino-3-N-isopropylamino-6-(2',4'-6'-triisopropylphenyl)pyridine

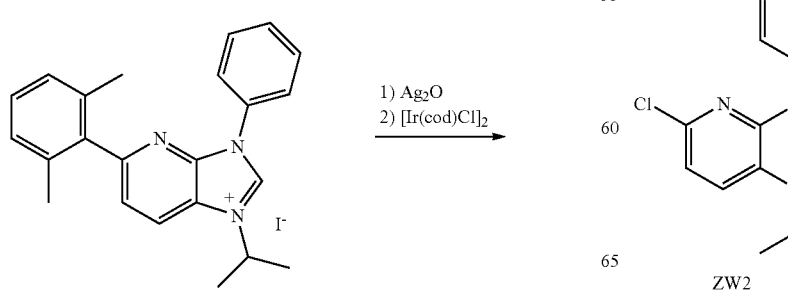

ZW2

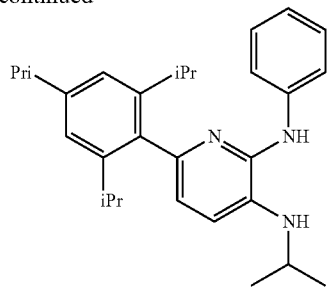

A solution of 2-N-phenylamino-3-N-isopropylamino-6-chloropyridine ZW2 (2.00 g, 7.64 mmol, for preparation see ZW2, Example 4) in dioxane (100 ml) is admixed with sodium hydroxide solution (50% in H$_2$O, 1.23 ml, 1.83 g, 22.9, 3.0 eq) and degassed, admixed with bis(tri-tert-butylphosphino)palladium (140 mg, 0.27 mmol, 3.5 mol%) and 2,4,6-triisopropylboronic acid (1.73 g, 6.98 mmol, 0.9 eq) and refluxed for 4 h. A further 40 ml of dioxane are added and the mixture is refluxed over the course of 92 h. The solvent is removed, and the mixture is taken up with dichloromethane and washed with water. The organic phase is removed and concentrated to dryness. The residue is purified by column chromatography (silica gel, CH:EA=3:2, then 9:1). Yield: 420 mg (14%).

$^1$H NMR (CD$_2$Cl$_2$, 500 MHz): δ=1.08, 1.09 (2×d, 12H), 1.26, 1.28 (2×d, 12H), 2.70 (2×sept., 2H), 2.91 (sept., 1H), 3.22 (br.s., 1H), 3.62 (sept., 1H), 6.35 (br. s, 1H), 6.75 (d, 1H), 6.88 (t, 1H), 7.03 (m$_c$, 3H), 7.22 (m$_c$, 2H), 7.27-7.29 (m, 2H).

1-Isopropyl-3-phenyl-5-(2',4',6'-triisopropylphenyl)-4-azabenzimidazolium Iodide

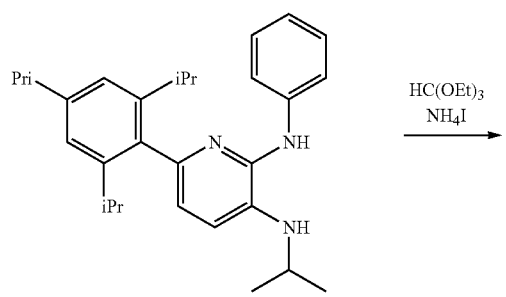

A mixture of 2-N-phenylamino-3-N-isopropylamino-6-(2',4',6'-triisopropylphenyl)pyridine (0.35 g, 0.83 mmol) in triethyl orthoformate (15 ml) is admixed with ammonium iodide (0.36 g, 2.5 mmol, 3.0 eq) and refluxed for 16 h. After cooling, the precipitate formed is filtered off and washed with petroleum ether and then dried. Yield: 0.34 g (73%).

$^1$H NMR (CD$_2$Cl$_2$, 500 MHz): δ=1.06 (d, 6H), 1.12 (d, 6H), 1.29 (d, 6H), 2.00 (d, 6H), 2.36 (sept., 2H), 2.96 (sept. 1H), 5.56 (sept., 1H), 7.12 (s, 2H), 7.59-7.68 (m, 4H), 8.18 (d, 2H), 8.33 (d, 1H), 11.32 (s, 1H).

Complex mer-Em6

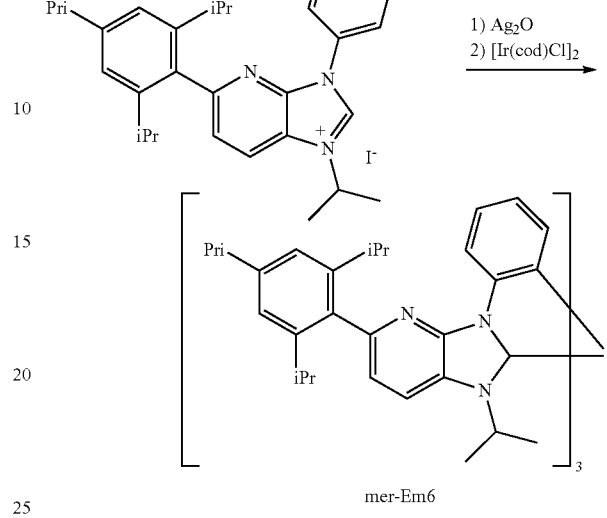

1-Isopropyl-3-phenyl-5-(2',4',6'-triisopropylphenyl)-4-azabenzimidazolium iodide (328 mg, 0.579 mmol) is initially charged in acetonitrile (60 ml) and admixed with silver(I) oxide (67 mg, 0.29 mmol), and the mixture is stirred at 50° C. for 18 h. The solvent is removed and o-xylene (60 ml) is added. The mixture is admixed with chloro(1,5-cyclooctadiene)iridium(I) dimer (39 mg, 0.058 mmol) and stirred at 135° C. for 66 h. After cooling, the solvent is removed, taken up with dichloromethane and washed with water. The organic phase is dried and concentrated, and the residue is purified by column chromatography (silica gel, cyclohexane:ethyl acetate=3:2). Yield: 151 mg (86%).

$^1$H NMR (CD$_2$Cl$_2$, 500 MHz): δ=0.62 (d, 3H), 0.69 (d, 3H), 0.89 (d, 3H), 1.03-1.14 (m, 36H), 1.30 (d, 21H), 1.35 (d, 3H), 1.70 (d, 3H), 2.34 (sept, 1H), 2.45 (sept. 1H), 2.50-2.64 (m, 3H), 2.75 (sept, 1H), 2.95 (m, 3H), 4.66 (sept, 1H), 4.79 (sept, 2H), 6.64-6.66 (m, 3H), 6.74 (d, 1H), 6.64-6.95 (m, 4H), 7.04-7.14 (m, 10H), 7.73 (d, 3H), 8.73 (d, 1H), 8.81 (d, 1H), 8.83 (d, 1H).

Photoluminescence (2% in a PMMA film):
λ$_{max}$=440 nm, CIE: (0.16; 0.10); QY=72%

Example 7

2-N-Phenylamino-3-N-isopropylamino-6-phenoxy-pyridine

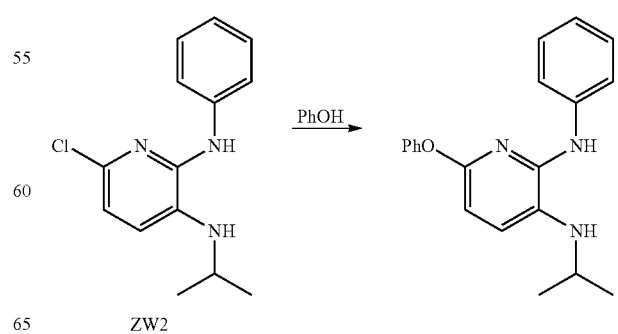

A mixture of 2-N-phenylamino-3-N-isopropylamino-6-chloropyridine ZW2 (2.08 g, 8.00 mmol, for preparation see ZW2, Example 4) phenol (3.76 g+4.0 g, 40 mmol+42.5 mmol, 10.3 eq.), Cs$_2$CO$_3$ (7.82 g, 24 mmol, 3.0 eq) and copper powder (100 mg, 1.6 mmol, 0.2 eq) is mixed cautiously and kept at 100° C. for 60 h. After cooling, dichloromethane and water are added, the phases are separated and the aqueous phase is extracted with dichloromethane. The combined organic phases are dried and concentrated. Purification is effected by chromatography (silica gel, CH:CH$_2$Cl$_2$=2:3). Yield: 720 mg (28%)

$^1$H NMR (CD$_2$Cl$_2$, 500 MHz): δ=1.17 (d, 6H), 2.56 (br.s, 1H), 3.36 (m/br.s, 1H), 6.31 (m/br. s, 1H), 6.84 (m/t, 1H), 7.07-7.27 (m, 7H), 7.29 (d, 2H), 7.39 (t, 2H).

1-Isopropyl-3-phenyl-5-phenoxy-4-azabenzimidazolium Iodide

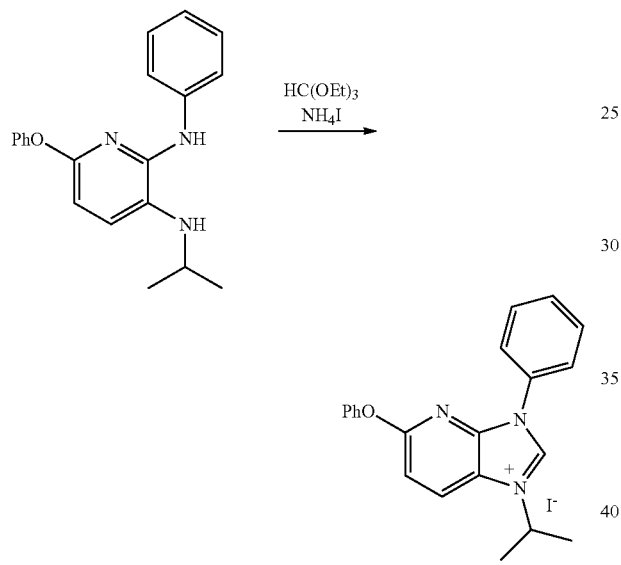

A mixture of 2-N-phenylamino-3-N-isopropylamino-6-phenoxypyridine (0.68 g, 2.1 mmol) in triethyl orthoformate (25 ml) is admixed with ammonium iodide (0.93 g, 6.39 mmol, 3.0 eq) and kept at 80° C. overnight. After cooling to 0° C., the precipitate formed is filtered off and washed with cold petroleum ether and then dried. Yield: 760 mg (78%).

$^1$H NMR (CD$_2$Cl$_2$, 500 MHz): δ=1.91 (d, 6H), 5.55 (sept., 1H), 7.21 (br. d, 2H), 7.27-7.34 (m, 2H), 7.45 (t, 2H), 7.51 (m, 3H), 8.04 (m, 2H), 8.45 (d, 1H), 11.00 (s, 1H).

Complex mer-Em7

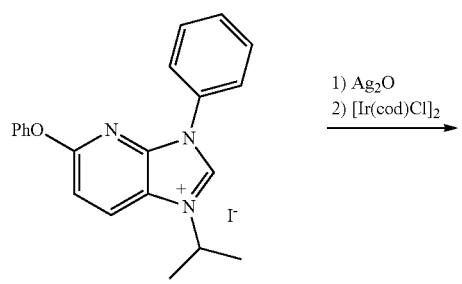

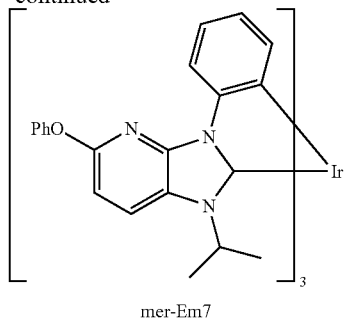

mer-Em7

1-Isopropyl-3-phenyl-5-phenoxy-4-azabenzimidazolium iodide (0.7 g, 1.53 mmol) is initially charged in acetonitrile (80 ml) and admixed with silver(I) oxide (180 mg, 0.77 mmol), and the mixture is stirred at 50° C. for 18 h. The solvent is removed and o-xylene (80 ml) is added. The mixture is admixed with chloro-1,5-(cyclooctadiene)iridium(I) dimer (103 mg, 0.153 mmol) and stirred at room temp. for 1 h, then at 135° C. for 18 h. After cooling, the solvent is removed and the residue is purified by column chromatography (silica gel, cyclohexane:ethyl acetate=4:1). Yield: 60 mg (5%).

$^1$H NMR (CD$_2$Cl$_2$, 500 MHz): δ=0.63 (d, 3H), 0.67 (d, 3H), 0.83 (d, 3H), 1.22 (d, 3H), 1.28 (d, 3H), 1.60 (d, 3H), 4.48 (sept, 1H), 4.57 (sept, 1H), 4.70 (sept, 1H), 6.53-6.63 (m, 5H), 6.78 (m$_c$, 6H), 6.93 (d, 1H), 7.26 (m, 9H), 7.45 (m, 6H), 7.72 (m, 3H), 8.18 (d, 1H), 8.81 (d, 2H).

Photoluminescence (2% in a PMMA film):
λ$_{max}$=444 nm, CIE: (0.16; 0.12); QY=75%

Example 8

2-N-(4-tert-butylphenyl)amino-3-N-isopropylaminopyridine

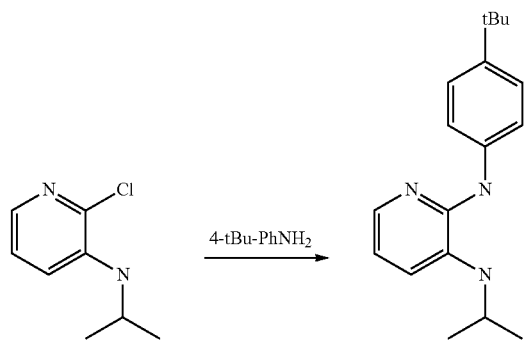 [SMILES: CC(C)Nc1cccnc1Cl ; CC(C)Nc1cccnc1Nc1ccc(C(C)(C)C)cc1]

A mixture of 2-chloro-3-N-isopropylaminopyridine (17.9 g, 102 mmol) in 4-(tert-butyl)aniline (17.0 ml, 107 mmol) is stirred at 180° C. overnight. After cooling to room temperature, the solid is dissolved in dichloromethane (100 ml) and admixed with water (100 ml). Sodium hydroxide solution (25%) is added to the resulting mixture until a pH of 11 has been attained. The phases are separated, and the aqueous phase is extracted with dichloromethane (2×50 ml). The combined organic phases are concentrated to dryness and the crude product is purified by column chromatography (silica gel, ethyl acetate/n-hexane gradient). Yield: 19.9 g (69%).

$^1$H NMR (CD$_2$Cl$_2$, 400 MHz): δ=1.22 (d, 6H), 1.31 (s, 9H), 3.19 (br. s, 1H), 3.57 (mc, 1H), 6.16 (s, 1H), 6.79 (dd, 1H), 6.95 (dd, 1H), 7.20-7.24 (m, 2H), 7.28-7.32 (m, 2H), 7.68 (dd, 1H).

1-Isopropyl-3-(4-tert-butylphenyl)-4-azabenzimidazolium Iodide

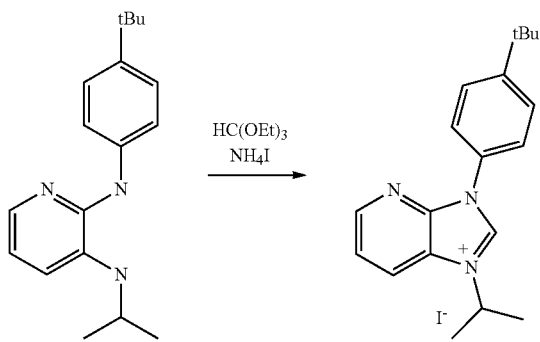

A mixture of 2-N-(4-tert-butylphenyl)amino-3-N-isopropylaminopyridine (12.1 g, 42.7 mmol) and triethyl orthoformate (90 ml) is admixed with ammonium iodide (6.50 g, 44.8 mmol) and stirred at 80° C. overnight. After cooling to room temperature, the solid is filtered off with suction and washed with petroleum ether and a little ethyl acetate. Yield: 16.1 g (90%).

$^1$H NMR (d$_6$-DMSO, 400 MHz): δ=1.37 (s, 9H), 1.71 (d, 6H), 5.17 (sept, 1H), 7.73-7.77 (m, 2H), 7.83-7.88 (m, 3H), 8.78-8.82 (m, 2H), 10.37 (s, 1H).

Complex mer-Em8

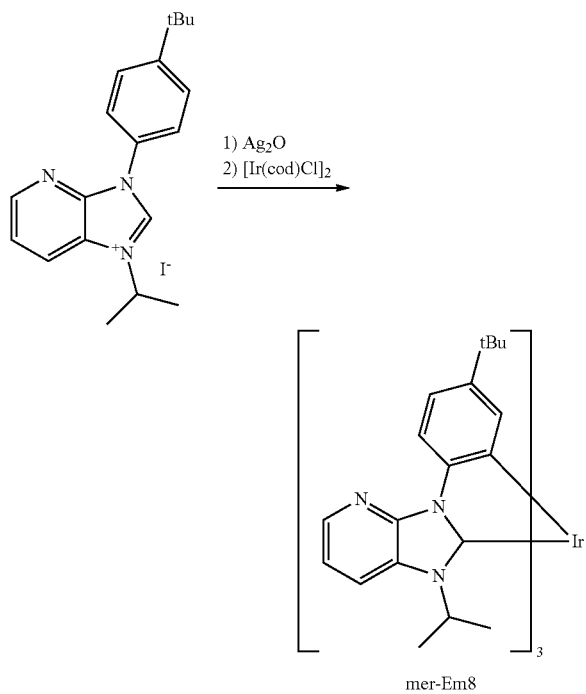

A suspension of 1-isopropyl-3-(4-tert-butylphenyl)-4-azabenzimidazolium iodide (8.05 g, 19.2 mmol) and 3 Å molecular sieve (60 g) in dioxane (400 ml) is admixed with silver(I) oxide (3.35 g, 14.5 mmol) and stirred at room temperature overnight. The mixture is admixed with a solution of chloro (1,5-cyclooctadiene)iridium(I) dimer (1.28 g, 1.91 mmol) in o-xylene (600 ml) and stirred at 110° C. overnight. After cooling to room temperature, the precipitate is filtered off with suction and washed with dichloromethane. The combined filtrates are concentrated to dryness. The residue is admixed with methyl tert-butyl ether (50 ml), homogenized in an ultrasound bath and filtered off with suction. The solid is column-filtered (silica gel, dichloromethane). The product fractions are concentrated to dryness. Yield: 2.53 g (61%).

$^1$H NMR (CD$_2$Cl$_2$, 400 MHz): δ=0.58 (d, 3H), 0.65 (d, 3H), 0.83 (d, 3H), 1.00 (s, 9H), 1.04 (s, 9H), 1.14 (s, 9H), 1.26 (d, 3H), 1.34 (d, 3H), 1.73 (d, 3H), 4.48 (sept, 1H), 4.79 (sept, 1H), 4.89 (sept, 1H), 6.56 (d, 1H), 6.71 (d, 1H), 6.93 (dd, 1H), 7.04-7.18 (m, 6H), 7.69-7.76 (m, 3H), 8.33-8.42 (m, 3H), 8.64 (t, 2H), 8.76 (d, 1H).

Photoluminescence (2% in a PMMA film): $λ_{max}$=449 nm, CIE: (0.16; 0.13); QY=93%

Example 9

2-N-(4'-(N'-Ethylcarbazolyl))-3-N-isopropylaminopyridine

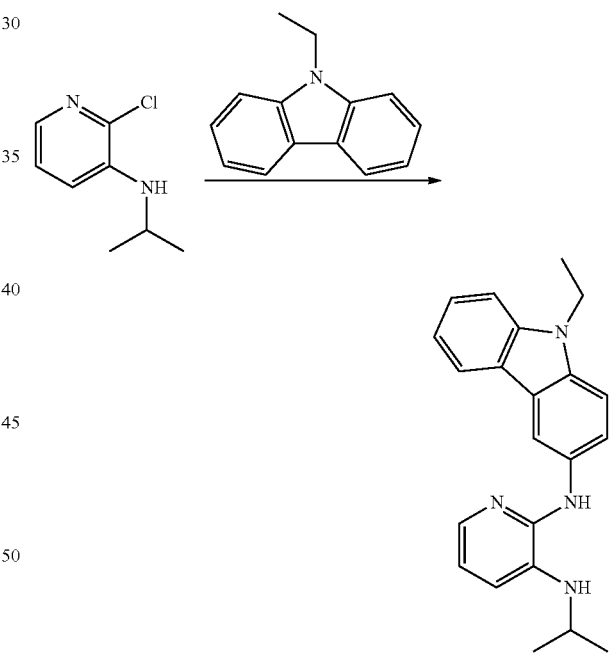

A mixture of 2-chloro-3-N-isopropylaminopyridine (2.00 g, 11.7 mmol) in N-ethyl-4-aminocarbazole (5.2 g, 23.5 mmol) is stirred at 150° C. overnight. After cooling to room temperature, the solid is taken up in dichloromethane. The insoluble residue is filtered off and discarded. The filtrate is admixed with water. Sodium hydroxide solution (25%) is added to the resulting mixture until a pH of 11 has been attained. The phases are separated, and the aqueous phase is extracted with dichloromethane (2×50 ml). The combined organic phases are concentrated to dryness and the crude product is purified by column chromatography (alumina, dichloromethane). Yield: 3.65 g (90%).

$^1$H NMR (CD$_2$Cl$_2$, 400 MHz): δ=1.23 (d, 6H), 1.42 (t, 3H), 3.61 (sept, 1H), 4.36 (q, 2H), 6.33 (s, 1H), 6.76-6.80 (m, 1H), 6.96 (d, 1H), 7.17 (t, 1H), 7.35-7.46 (m, 4H), 7.69 (d, 1H), 8.00 (s, 1H), 8.02 (d, 1H).

1-Isopropyl-3-(4'-N'-ethylcarbazolyl))-4-azabenzimidazolium Iodide

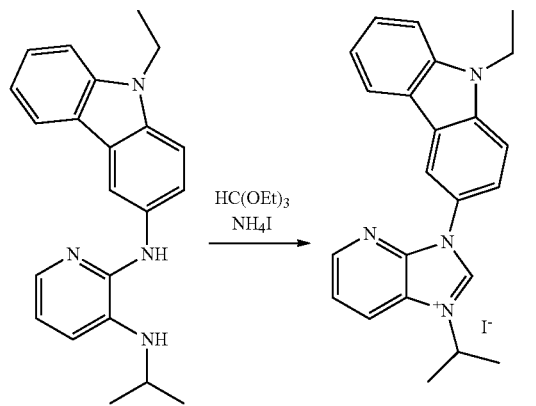 [SMILES: CCn1c2ccccc2c2cc(Nc3ncccc3NC(C)C)ccc21 ; CCn1c2ccccc2c2cc(-n3c[n+](C(C)C)c4cccnc43)ccc21 ; [I-]]

A mixture of 2-N-(4'-(N'-ethylcarbazolyl))-3-N-isopropylaminopyridine (4.04 g, 11.7 mmol) and triethyl orthoformate (50 ml) is admixed with ammonium iodide (1.70 g, 11.7 mmol) and stirred at 80° C. overnight. After cooling to room temperature, the solid is filtered off with suction and washed with cyclohexane. The resulting solid is dissolved in dichloromethane and precipitated by adding cyclohexane. The solid is filtered off with suction and dried under reduced pressure. Yield: 3.01 g (53%).

$^1$H NMR (d$_6$-DMSO, 400 MHz): δ=1.38 (t, 3H), 1.75 (d, 6H), 4.58 (q, 2H), 5.22 (sept, 1H), 7.31 (d, 1H), 7.56-7.60 (m, 1H), 7.76 (d, 1H), 7.86-7.89 (m, 1H), 7.95-7.99 (m, 2H), 8.22 (d, 1H), 8.68 (s, 1H), 8.81-8.85 (m, 2H), 10.47 (s, 1H).

Complex mer-Em9

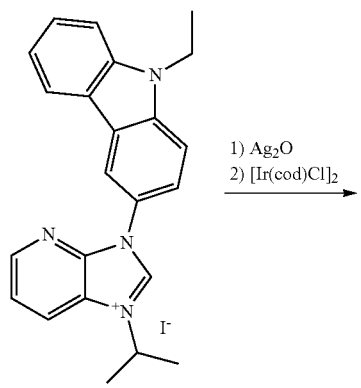

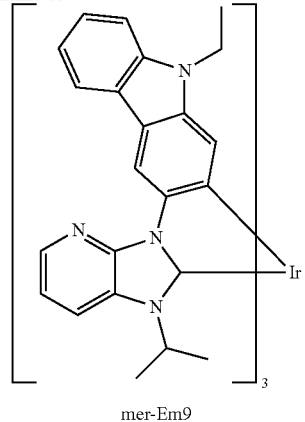

mer-Em9

A suspension of 1-isopropyl-3-(4'(N'-ethylcarbazolyl))-4-azabenzimidazolium iodide (3.99 g, 8.27 mmol) and 3 Å molecular sieve (50 g) in dioxane (700 ml) is admixed with silver(I) oxide (1.97 g, 8.50 mmol) and stirred at room temperature for 48 h. The mixture is admixed with a solution of chloro(1,5-cyclooctadiene)iridium(I) dimer (555 mg, 0.83 mmol) in o-xylene (500 ml) and stirred at 110° C. overnight. After cooling to room temperature, the precipitate is filtered off with suction and washed with ethyl acetate. The combined filtrates are concentrated to dryness. The residue is purified by column chromatography (silica gel, 4:1 n-hexane/ethyl acetate). The resulting solid is recrystallized from hot methyl tert-butyl ether (50 ml), filtered off with suction and dried. Yield: 910 mg (44%).

$^1$H NMR (CD$_2$Cl$_2$, 400 MHz): δ=0.67 (d, 3H), 0.73 (d, 3H), 0.85-0.89 (m, 6H), 0.91 (d, 3H), 1.03 (t, 3H), 1.14 (t, 3H), 1.22-1.29 (m, 3H), 1.77 (d, 3H), 3.73 (m, 2H), 3.90 (m, 2H), 4.02 (q, 2H), 4.78 (sept., 1H), 4.90 (sept., 1H), 4.99 (sept., 1H), 6.64 (s, 1H), 6.73 (s, 1H), 7.05-7.31 (m, 11H), 7.77 (t, 2H), 7.82 (d, 1H), 8.08-8.16 (m, 3H), 8.48 (d, 1H), 8.53 (d, 1H), 8.59 (d, 1H), 9.63 (s, 1H), 9.64 (s, 1H), 9.72 (s, 1H).

Photoluminescence (2% in a PMMA film):
λmax=458 nm, CIE: (0.15; 0.15); QY=70%;

Example 10

1,3-Diphenyl-3H-benzimidazolium tetrafluoroborate

The synthesis of this compound is described in WO2005/019373 (compound 3).

Complex K1

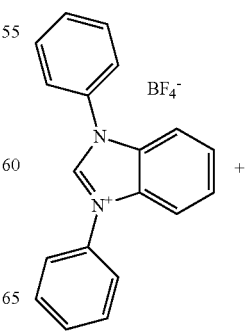

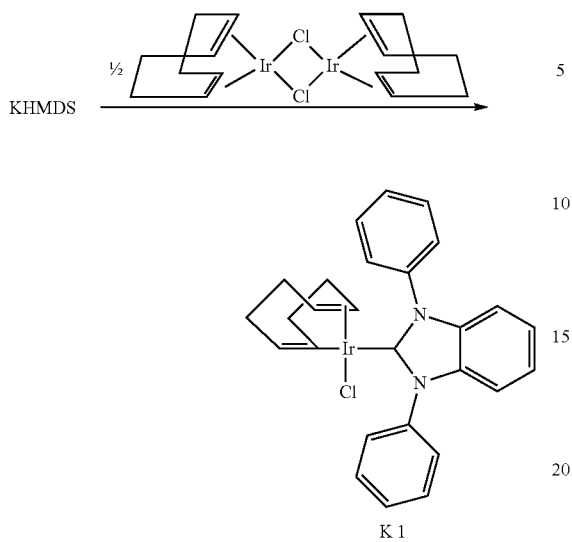

5.00 g (14.0 mmol) of 1,3-diphenyl-3H-benzimidazolium tetrafluoroborate are suspended in 80 ml of anhydrous toluene and cooled to −8° C. Then 28 ml of potassium bis(trimethylsilyl)amide (KHMDS, 0.5M in toluene, 14.0 mmol) are added within 10 min. The mixture is stirred at room temperature for one hour and then added dropwise at −78° C. within 15 min to a solution of 4.70 g (7.0 mmol) of [(μ-Cl)Ir(η$^4$-1,5-COD)]$_2$ in 120 ml toluene. The reaction mixture is stirred at room temperature for 1.5 h and then heated at reflux for 19 h. After cooling, the precipitate is filtered off and washed with toluene. The combined toluene phases are concentrated to dryness and purified by column chromatography (silica gel, eluent methylene chloride). This gives 5.8 g (68%) of K1 yellow powder.

$^1$H NMR (CD$_2$Cl$_2$, 500 MHz):

δ=1.17 (m, 2H), 1.34 (m, 4H), 1.61 (m, 2H), 2.43 (m, 2H), 4.31 (m, 2H), 7.18 (m, 2H), 7.25 (m, 2H), 7.51 (m, 6H), 7.96 (m, 4H).

Complex Em10

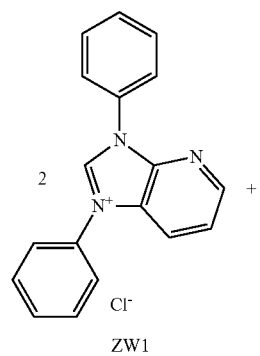

ZW1

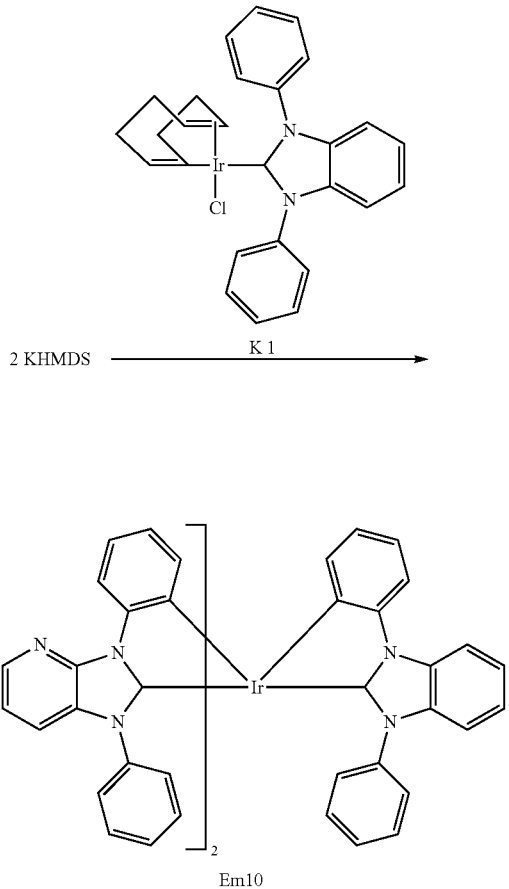

Em10

A suspension of 0.98 g (3.2 mmol) of 1,3-diphenyl-4-azabenzimidazolium chloride ZW1 in 75 ml of anhydrous toluene are admixed gradually at 0° C. with 6.4 ml of potassium bis(trimethylsilyl)amide (KHMDS, 0.5M in toluene, 3.2 mmol). The reaction mixture is allowed to warm up and is stirred at room temperature for 1 h. Then a solution of 0.92 g (1.5 mmol) of K1 in 125 ml of anhydrous toluene is added dropwise. This is followed by stirring at room temperature for half an hour and at reflux for 18 h. After removing the solvent under reduced pressure, the residue is purified by column chromatography (silica gel, eluent:cyclohexane/acetone with the mass ratio of 4/1). This gives 0.17 g of Em10 as a yellow powder (R$_F$=0.30).

$^1$H NMR (CD$_2$Cl$_2$, 500 MHz): δ=6.23-6.31 (m, 6H), 6.38-6.42 (m, 2H), 6.58-6.68 (m, 5H), 6.72-6.80 (m, 7H), 6.97-7.05 (m, 3H), 7.08-7.14 (m, 3H), 7.26-7.35 (m, 5H), 7.97 (d, 1H), 8.15 (d, 1H), 8.34-8.37 (m, 2H), 8.92 (d, 1H), 8.94 (d, 1H).

Photoluminescence (2% in a PMMA film):

λ$_{max}$=416 nm, CIE: (0.16; 0.06); QY=45%;

Example 11

Complex Em11-s

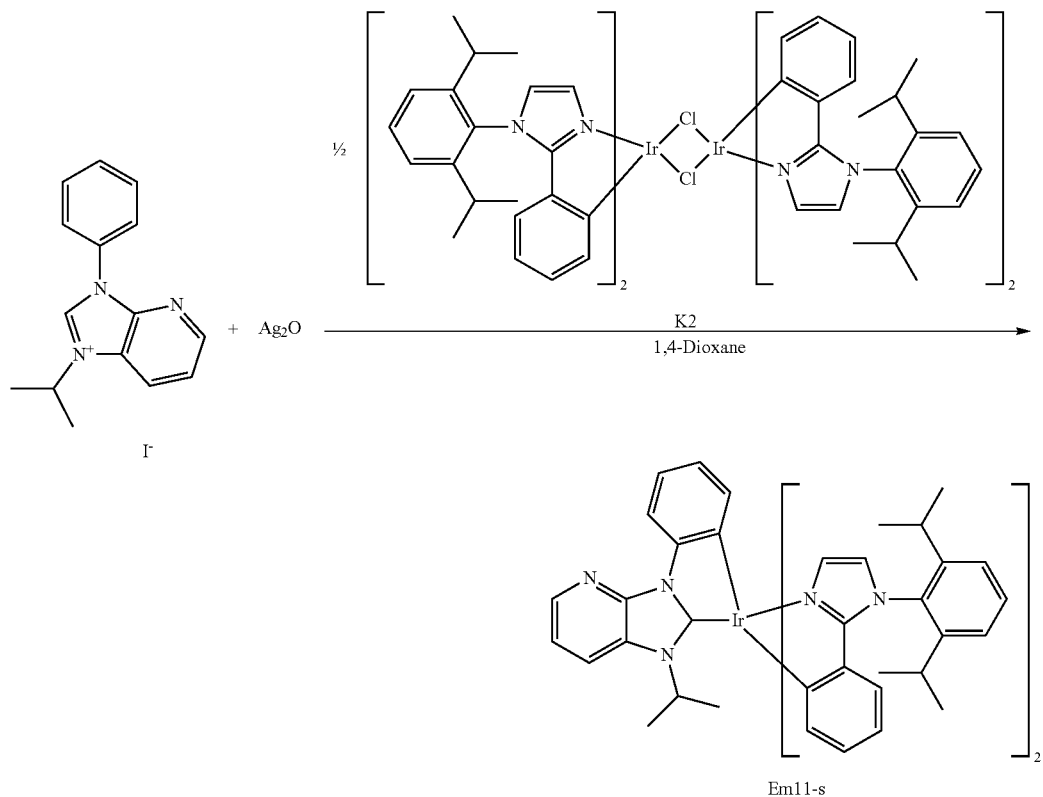

A suspension of 1-isopropyl-3-phenyl-4-azabenzimidazolium iodide (synthesis described in stage 3, Example 2; 0.46 g, 1.3 mmol) in anhydrous dioxane (100 ml) is admixed with molecular sieve (10 g) and silver(I) oxide (0.19 g, 0.81 mmol), and the mixture is stirred at room temperature overnight. Subsequently, a solution of chloro dimer K2 (the N-(2,6-diisopropylphenyl)-2-phenylimidazole ligands were synthesized analogously to Example 14 in WO2006/121811; the preparation of the chloro dimer K2 is described as compound D1 in WO 2011/051404; 0.52 g, 0.31 mmol) is dissolved in dioxane (50 ml) and added dropwise to the reaction mixture. This was followed by dilution with further dioxane (25 ml). Thereafter, the mixture is stirred under reflux for one hour. The reaction mixture is cooled and filtered. The filtrate is freed of the solvent under reduced pressure, washed with methanol. This gives 0.40 g of Em11-s as a yellow powder (62%).

$^1$H NMR (CD$_2$Cl$_2$, 500 MHz):
δ=0.89 (d, 3H), 0.93 (2d, 6H), 0.96-1.02 (4d, 12H), 1.18 (d, 3H), 1.22 (d, 3H), 1.53 (d, 3H), 2.16 (sept, 1H), 2.49 (m, 1H), 2.70 (sept, 1H), 2.82 (sept, 1H), 5.51 (sept, 1H), 6.15 (d, 1H), 6.23 (d, 1H), 6.39 (d, 1H), 6.45 (t, 1H), 6.48 (t, 1H), 6.54 (d, 1H), 6.58 (d, 1H), 6.65 (2d, 2H), 6.73 (t, 2H), 6.76 (t, 1H), 6.83 (d, 1H), 7.00 (t, 1H), 7.08 (d, 1H), 7.17 (dd, 1H), 7.29-7.35 (m, 4H), 7.51 (2t, 2H), 7.81 (dd, 1H), 8.40 (dd, 1H), 8.84 (d, 1H).

MS (Maldi):
m/e=1034 (M+H)$^+$
Photoluminescence (2% in a PMMA film):
λ$_{max}$=488 nm, CIE: (0.18; 0.32);

Complex Em11-i

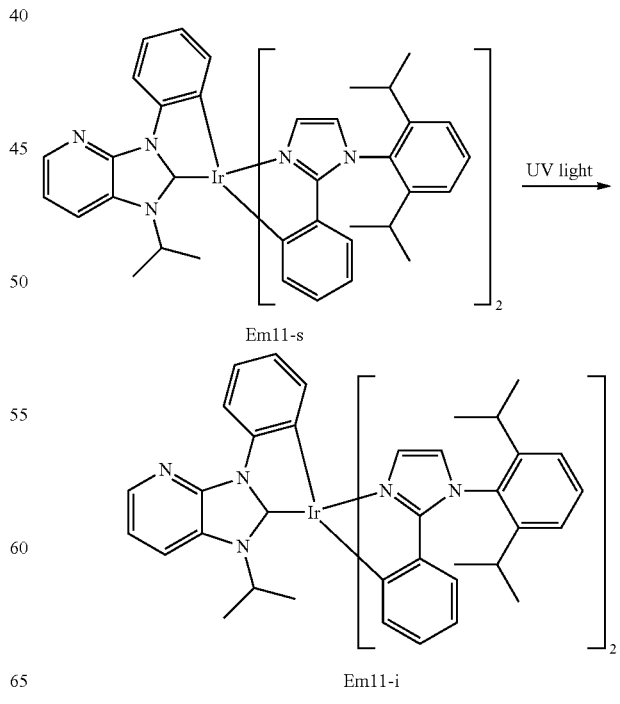

The complex Em11-i (isomer of Em11-s) is obtained by irradiating a solution of Em11-s in 3-methoxypropionitrile with a blacklight blue lamp (Osram, L18W/73, $\lambda_{max}$=370-380 nm) and subsequent column chromatography purification (cyclohexane:acetone=10:1).

$^1$H NMR (CD$_2$Cl$_2$, 500 MHz):
δ=0.62 (d, 3H), 0.83 (d, 3H), 0.88 (d, 3H), 1.01 (d, 3H), 1.05 (d, 3H), 1.08 (d, 3H), 1.14 (d, 3H), 1.19 (d, 3H), 1.22 (d, 3H), 1.71 (d, 3H), 1.77 (sept, 1H), 2.50 (sept. 1H), 2.60 (sept, 1H), 2.78 (sept, 1H), 5.26 (sept, 1H), 6.14 (d, 1H), 6.20 (d, 2H), 6.39-6.48 (m, 3H), 6.54 (m, 2H), 6.62-6.73 (m, 4H), 6.79 (s, 1H), 6.90 (s, 1H), 6.97 (t, 1H), 7.13 (dd, 1H), 7.25 (d, 1H), 7.33-7.37 (m, 3H), 7.49 (t, 1H), 7.54 (t, 1H), 7.75 (d, 1H), 8.35 (d, 1H), 8.74 (d, 1H).

MS (Maldi):
m/e=1034 (M+H)$^+$
Photoluminescence (2% in a PMMA film):
$\lambda_{max}$=484 nm, CIE: (0.18; 0.32);

Example 12

Complex Em12-s

A suspension of 1-isopropyl-3-phenyl-4-azabenzimidazolium iodide (synthesis described in stage 3, Example 2; 0.46 g, 1.3 mmol) in anhydrous dioxane (100 ml) is admixed with molecular sieve (10 g) and silver(I) oxide (0.19 g, 0.81 mmol), and stirred at room temperature overnight. Subsequently, a solution of chloro dimer K3 (the preparation of the chloro dimer is described as compound D2 in WO 2011/051404, 0.57 g, 0.31 mmol) is dissolved in dioxane (100 ml) and added dropwise to the reaction mixture. Thereafter, the mixture is stirred under reflux for three hours. The reaction mixture is cooled and filtered. The filtrate is freed of the solvent under reduced pressure, washed with methanol. This gives, after column chromatography purification (cyclohexane:acetone=25:1), 0.35 g of Em12-s as a lemon yellow powder (49%).

MS (Maldi):
m/e=1098 (M+H)$^+$
Photoluminescence (2% in a PMMA film):
$\lambda_{max}$=481 nm, CIE: (0.20; 0.29).

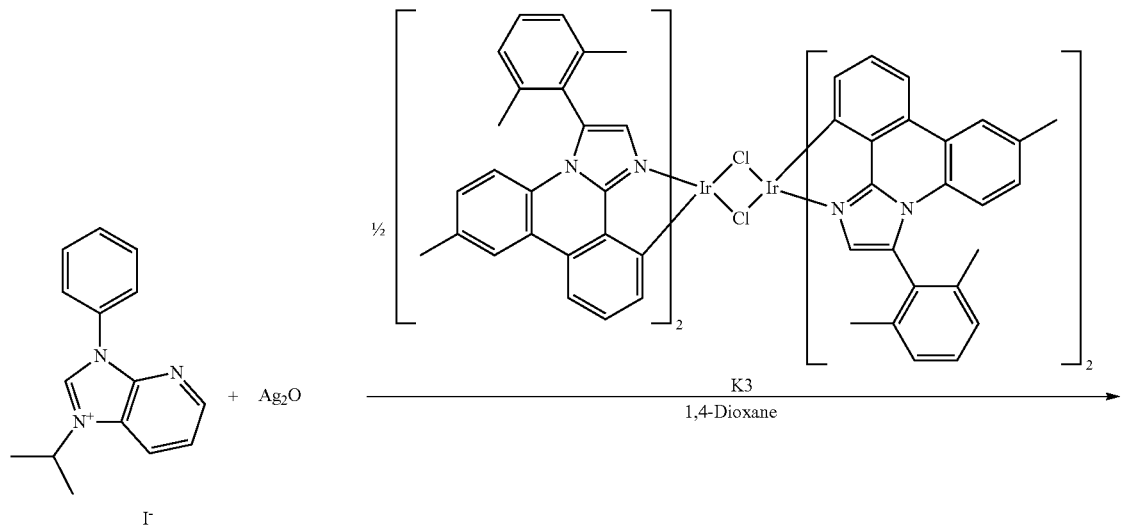

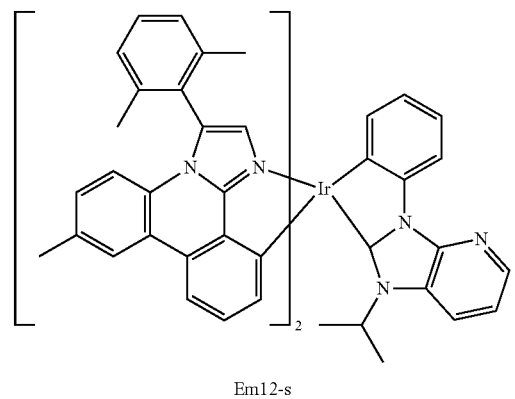

Em12-s

Complex Em12-i

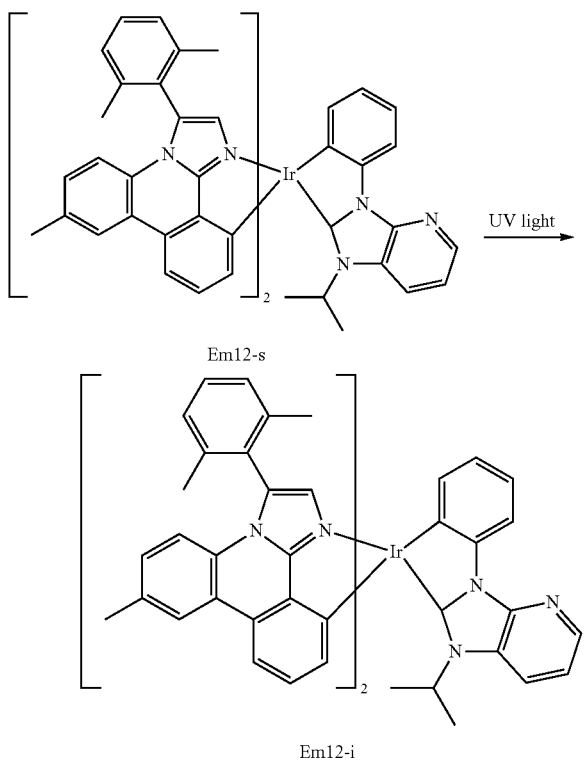

Em12-s

Em12-i

The complex Em12-i (isomer of Em12-s) is obtained by irradiating a solution of Em12-s in 3-methoxypropionitrile with a blacklight blue lamp (Osram, L18W/73, $\lambda_{max}$=370-380 nm) and subsequent column chromatography purification (cyclohexane:acetone=10:1).

MS (Maldi):
m/e=1098 (M+H)$^+$
Photoluminescence (2% in a PMMA film):
$\lambda_{max}$=480 nm, CIE: (0.17; 0.24).

Example 13 (Comparative Example, Noninventive)

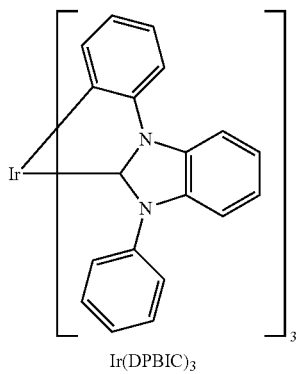

Ir(DPBIC)$_3$

Preparation and photophysical data of 1r(DPBIC)$_3$ are described in WO2005/019373 (see facial Ir complex (7)).

Photoluminescence (in a PMMA film, see Tab. 3 in WO2005/019373, sample 3): CIE: (0.16; 0.05), quantum yield: 17%.

II Device Examples

Example 14

Production of an OLED (Using the Example of Em11-i) Use as an Emitter

The ITO substrate used as the anode is cleaned first with commercial detergents for LCD production (Deconex® 20NS, and 250RGAN-ACID® neutralizing agent) and then in an acetone/isopropanol mixture in an ultrasound bath. To eliminate possible organic residues, the substrate is exposed to a continuous ozone flow in an ozone oven for a further 25 minutes. This treatment also improves the hole injection properties of the ITO. Next, the hole injection layer AJ20-1000 from Plexcore is spun on from solution.

Thereafter, the organic materials specified below are applied by vapor deposition to the cleaned substrate at about $10^{-7}$-$10^{-9}$ mbar at a rate of approx. 0.5-5 nm/min. The hole conductor and exciton blocker applied to the substrate is Ir(DPBIC)$_3$ with a thickness of 45 nm, of which the first 35 nm are doped with MoO$_x$ to improve the conductivity.

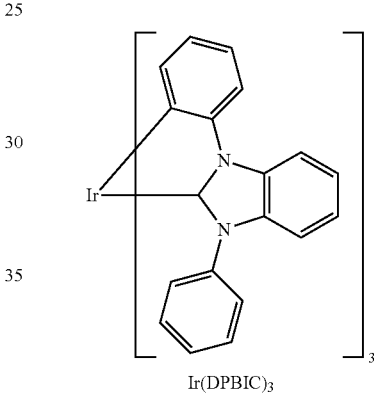

Ir(DPBIC)$_3$ (for preparation of 1r(DPBIC)$_3$ see Ir complex (7) in the application PCT/EP/04/09269).

Subsequently, a mixture of emitter, in this case Em11-i (15%), and of the compound Ma1 is applied by vapor deposition with a thickness of 20 nm, the latter compound functioning as a matrix material.

Ma1

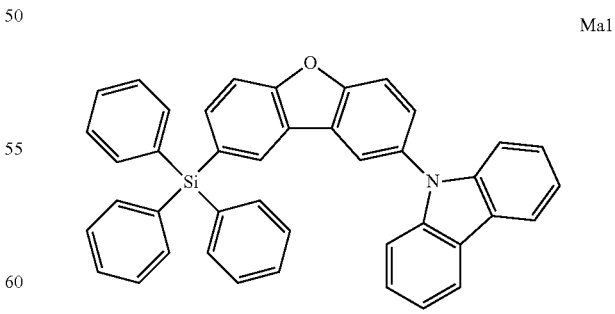

Compound Ma1 is described as No. 14 in WO 2010/079051.

Subsequently, the material Ir(DPBIC)$_3$ is applied by vapor deposition with a thickness of 5 nm as an exciton and hole blocker. Next, as an electron transporter, a mixture of Liq and BCP (2,9-dimethyl-4,7-diphenyl-1,10-phenanthroline) is applied by vapor deposition in a thickness of 40 nm, as are a 1.0 nm-thick liq layer and finally a 100 nm-thick Al electrode. All components are adhesive-bonded to a glass lid in an inert nitrogen atmosphere.

Liq

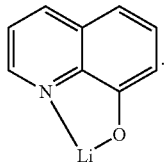

To characterize the OLED, electroluminescence spectra are recorded at different currents and voltages. In addition, the current-voltage characteristic is measured in combination with the light output emitted. The light output can be converted to photometric parameters by calibration with a photometer. The lifetime $t_{1/2}$ of the diode is defined by the time taken for the luminance to fall to 50% of its initial value. The lifetime measurement is carried out at a constant current.

A luminous diode with the following CIE values is obtained: 0.18; 0.26 (voltage in V @ 300 nits: 4.5).

Example 15

Influence of the Matrix Materials MM Using the Example of Mer-Em8, or/and Use of Inventive Compounds as Matrix Material Diode Structure:
  HIL Plexcore AJ20-1000—10 nm Ir(DPBIC)$_3$:ReO$_3$ (95:5)—10 nm Ir(DPBIC)$_3$—20 nm MM:mer-Em8 (80:20)—5 nm Ma1—35 nm T1:Liq (50:50)—4 nm KF—100 nm Al; the diode was produced analogously to Example 14.

T1

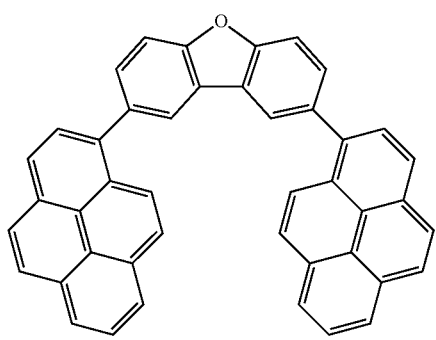

The synthesis of T1 is described as A1 in European application EP10166507.3 and in U.S. application US61/356,057.

For the emitter mer-Em8 in various matrix materials (without matrix material) in the above-described OLED structure, the following electrooptical data are obtained:

| Matrix "MM" | CIE | Voltage at 2000 nits | EQE at 300 nits |
|---|---|---|---|
| Ma1[1] | 0.16/0.20 | 100% | 100% |
| LB1[2] | 0.16/0.17 | 114% | 144% |
| mer-Em8[3] | 0.18/0.26 | 94% | 178% |

[1]In this structure, the hole conductor layer was 15 nm, but the hole blocker layer was 5 nm and the electon conductor layer was 40 nm.
[2]In this case, 30% mer-Em8 was used as emitter; the hole transporter consisted of 10 nm of Ir(DPBIC)$_3$, the hole blocker of 10 nm of LB1;

LB1

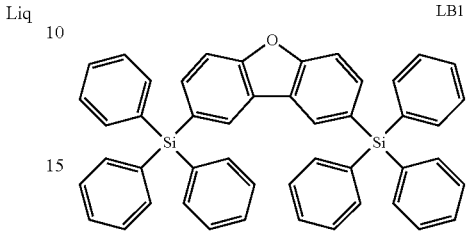

Compound LB1 is described as compound "4g" in WO2009/003898.
[3]The emitter functioned in this case as the matrix itself; the hole blocker layer in this case was 10 nm.

Example 16

Use of Inventive Compounds as Hole Conductors and Electron Blockers LL Using the Example of fac-EM2, and Comparative Example Diode Structure:
  Plexcore AJ20-1000—35 nm LL:MoO$_x$ (90:10)—10 nm LL—20 nm Ma2:AEm (70:30)—10 nm Ma2—20 nm T2—4 nm CsF—100 nm Al; the diode was produced analogously to Example 14.
with:

Ma2

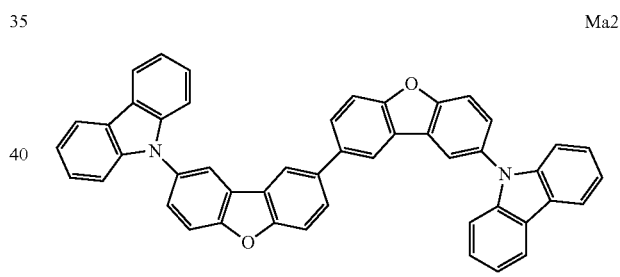

Ma2, described as compound (1) in WO 07077810 A1

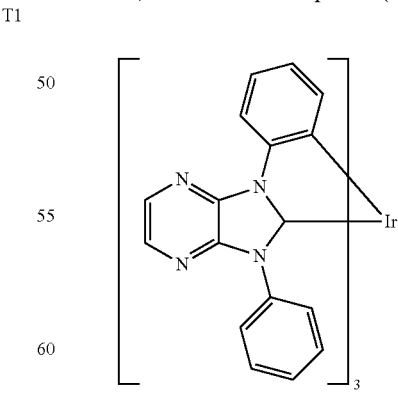

AEm

AEm, described as compound in fac-Em1 in European application EP10 187 176.2 and U.S. application 61/391,712 and also PCT application PCT/EP2010/069541, and

T2

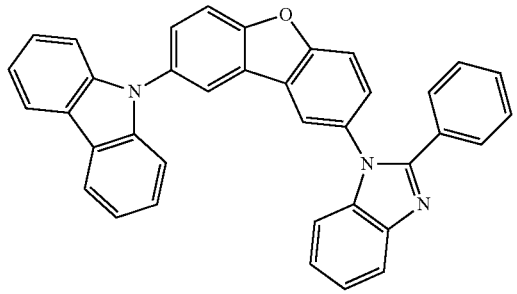

T2, synthesis described as compound 7 in European application EP 10168921.4 and U.S. application US61/362,314.

As hole conductors result in the above-described OLED structure in the following electrooptical data:

| Hole conductor/electron blocker "LL" | CIE | Voltage at 300 nits |
|---|---|---|
| fac-EM2 | 0.17/0.29 | 97% |
| Ir(DPBIC)$_3$— Comparative example, noninventive | 0.17/0.29 | 100% |

Example 17

Use of Inventive Compounds as Emitters in a Mixed Matrix Using the Example of fac-EM2

Diode Structure:

Plexcore AJ20-1000—35 nm fac-Em2:MoO$_x$ (90:10)—10 nm fac-Em2—20 nm Ma2:AEm:fac-Em2—10 nm Ma2—20 nm T2—4 nm CsF—100 nm Al; the diode is produced analogously to Example 14.

The variation of the concentration of the emitters results in the following electrooptical data in the OLED structure described above:

| Ma2:AEm:fac-Em2 | CIE | Voltage at 300 nits | EQE in % at 300 nits | LT$_{50}$ [%] |
|---|---|---|---|---|
| 55:30:15 | 0.17/0.30 | 93% | 132% | 450% |
| 40:30:30 | 0.18/0.32 | 83% | 126% | 250% |
| 70:30:00[1] | 0.17/0.29 | 100% | 100% | 100% |

[1]In this case too, fac-Em2 is, however, still being used as the hole conductor and electron blocker.

Example 18

2-Chloro-3-amino-5-(trifluoromethyl)pyridine

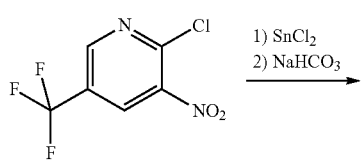

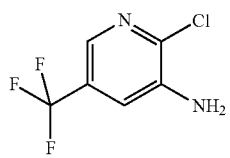

Zink(II)-chloride-dihydrate (4.39 g, 19.5 mmol) is added to a solution of 2-chloro-3-nitro-5-(trifluoromethyl)pyridine (1.00 g, 4.41 mmol) in a ethyl acetate (25 ml), and the resultant suspension is stirred for 2 h at 80° C. After cooling to room temperature, the reaction mixture is slowly added dropwise into an ice cooled saturated sodium hydrogen carbonate solution (100 ml). After warming to room temperature, the resultant suspension is filtered via a celite layer, and the residue is washed four times with ethyl acetate (50 ml each). The filtrate and the washing solution are combined and subsequently washed with a saturated sodium hydrogen carbonate solution, water and a saturated aqueous sodium chloride solution. The organic phase is dried over magnesium sulfate, filtered and concentrated to dryness. Yield: 0.78 g (90%).

$^1$H-NMR (CD$_2$Cl$_2$, 400 MHZ: δ=4.4. (br s, 2H), 7.24 (d, 1H), 8.02 (d, 1H).

2-Chloro-3-N-isopropylamino-5-(trifluoromethyl) pyridine

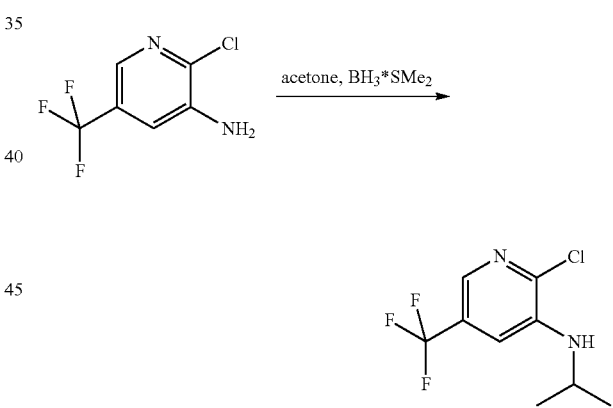

To a solution of 2-chloro-3-amino-5(trifluormethyl)pyridine (0.78 g, 3.97 mmol) in dichloromethane (10 ml) are added subsequently at 0° C. glacial acetic acid (5 ml), acetone (0.62 g, 10.7 mmol) and borane-dimethyl sulfide (0.33 g, 4.37 mmol). After warming to room temperature the resulting solution is stirred for 16 h. The reaction mixture is cooled to 0° C., and then a 25% aqueous ammonia solution is added until a pH of 8 is reached. After addition of water (5 ml) the aqueous phase is removed and extracted three times with dichloromethane (40 ml). The combined organic phases are dried over magnesium sulfate, filtered and concentrated to dryness. Yield: 0.60 g (63%).

$^1$H-NMR (CD$_2$Cl$_2$, 400 MHz: δ=1.28 (d, 6H), 3.60-3.72 (m, 1H), 4.5 (br s, 1H), 7.02 (s, 1H), 7.89 (s, 1H).

2-N-Phenylamino-3-N-isopropylamine-5-(trifluoromethyl)pyridine

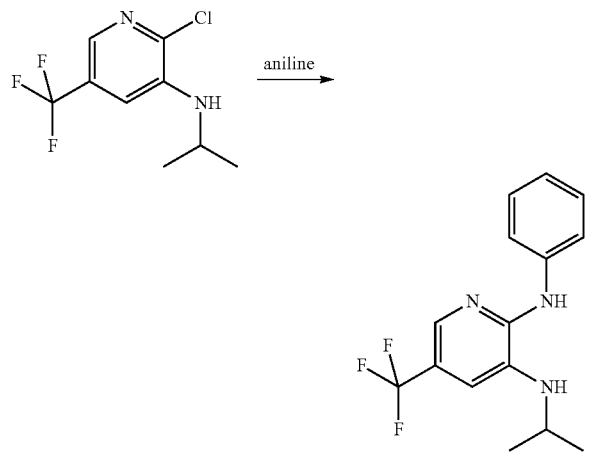

A mixture of 2-chloro-3-N-isopropylamino-5-(trifluoromethyl)pyridine (0.40 g, 1.68 nmol) and aniline (0.25 g, 2.72 nmol) is stirred at 180° C. for 16 h. After cooling to room temperature subsequently water (10 ml) and dichloromethane are added, and the pH value is then adjusted to 12 with a 50% aqueous sodium hydroxide solution. The phases are separated, and the aqueous phase is three times extracted with dichloromethane (30 ml). The combined organic phases are dried over magnesium sulfate, filtered and concentrated to dryness. The cooled product is purified by column chromatography with silica gel (eluent, cyclohexane/ethyl acetate 4:1). Yield: 0.24 g (49%).

$^1$H-NMR (CD$_2$Cl$_2$, 500 MHz): δ=1.26 (d, 6h), 3.2 (br s, 1H), 3.57-3.65 (m, 1H), 6.55 (s, 1H), 7.04 (t, 1H), 7.07 (d, 1H), 7.32 (t, 2H), 7.41-7.46 (m, 2H), 7.98 (s, 1H).

1-Isopropyl-3-phenyl-6-trifluoromethyl-4-azabenzimidazole-iodide

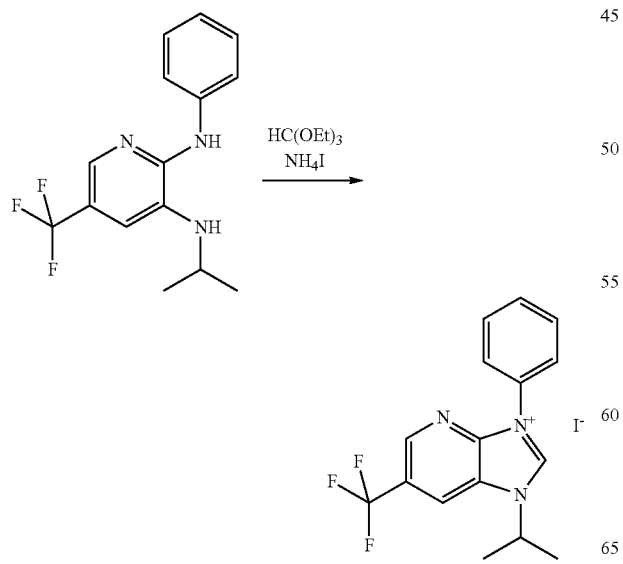

Ammoniumiodide (0.12 g, 0.85 mmol) is added to a solution of 2-N-phenylamino-3-N-isopropylamino-5-(trifluoromethyl)pyridine (0.22 g, 0.74 mmol) in triethylorthoformiate (7.5 ml), and the resultant reaction mixture is stirred at 85° C. for 18 h. After cooling to room temperature, the precipitate formed is filtered, washed with petroleum ether and dried in vacuo. Yield: 0.31 g (97%).

$^1$H-NMR (CD$_2$Cl$_2$, 500 MHz): δ=1.99 (d, 6H), 5.50 (sept, 1H), 7.66-7.74 (m, 3H), 8.19-8.22 (m, 2H), 8.57 (s, 1H), 9.08 (s, 1H), 11.46 (s, 1H).

Complex mer-EM13:

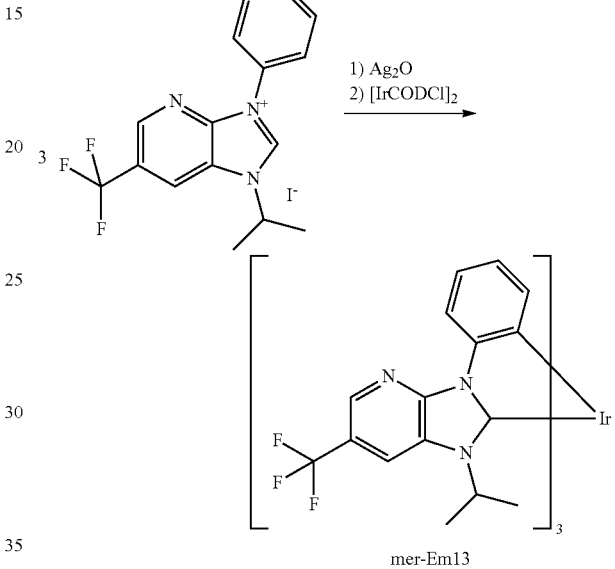

mer-Em13

Silver(I)oxide (0.50 g, 2.15 mmol) is added to a mixture of 1-isopropyl-3-phenyl-6-trifluoromethyl-4-azabenzimidazole-iodide (1.25 g, 2.88 mmol), molecular sieve (10 g) and 1,4-dioxane (150 ml), and the reaction mixture is stirred at room temperature for 16 h. The solvent is removed under reduced pressure and the residue is taken up in o-xylol (200 ml). A solution of Ir[(cod)Cl]$_2$ (575 mg, 0.86 mmol) in o-xylol (75 ml) is added dropwise in 20 min, and the reaction mixture is stirred under reflux for 48 h. After cooling to room temperature, the insoluble residue is filtered and the filtrate is concentrated to dryness. The cooled product is purified by column chromatography on silica gel (eluent: cyclohexane/acetone 10:1). Yield 0.30 g (16%)

1H-NMR (CD$_2$Cl$_2$, 500 MHz): δ=0.68 (d, 3H), 0.75 (d, 3H), 0.88 (d, 3H), 1.32 (d, 3H), 1.38 (d, 3H), 1.69 (d, 3H), 4.61-4.72 (m, 2H), 4.89 (sept, 1H), 6.55 (dd, 1H), 6.70-6.80 (m, 4H), 7.01-7.12 (m, 4H), 7.93-7.99 (m, 3H), 8.70-8.78 (m, 3H), 8.82-8.88 (m, 2H), 8.91 (dd, 1H).

Photoluminescence (2% in a PMMA-film):
$λ_{max}$=478 nm, CIE: (0.18; 0.28); QY=73%

Example 19

Use of mer-EM13 as an Emitter

Diode Structure 1:
HIL Plexcore AJ20-1000—10 nm Ir(DPBIC)$_3$: ReO$_3$ (95:5)—10 nm Ir(DPBIC)$_3$—40 nm Ma1: mer-EM 13 (80:20)—5 nm Ma1—25 nm T1:Liq(50:50)—4 nm KF—100 nm Al; the diode was produced analogously to example 14.

CIE (x;y)=(0.22; 0.39); voltage$_{300nits}$=4.1 V; EQE$_{300nits}$=14.0%.

Diode Structure 2:

HIL Plexcore AJ20-1000—10 nm Ir(DPBIC)$_3$:ReO$_3$ (95:5)—10 nm Ir(DPBIC)$_3$-40 nm Ma3:mer-Em13:Ir(DPBIC)$_3$ (75:10:15)—5 nm Ma3—20 nm T1:Liq (50:50)—4 nm KF—100 nm Al; the diode was produced analogously to example 14.

CIE (x;y)=(0.16; 0.27); voltage$_{300nits}$=4.1 V; EQE$_{300nits}$=12.1%.

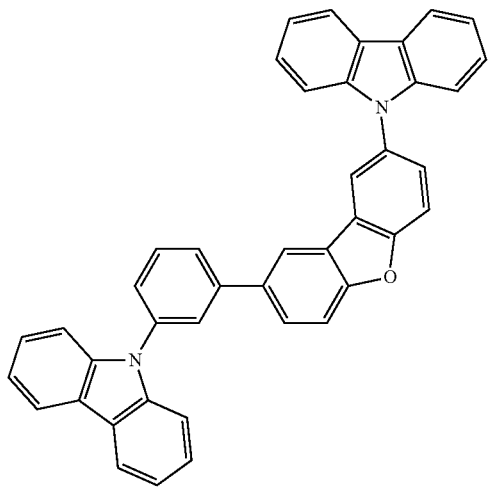 [SMILES: c1cc(-c2ccc3oc4ccc(-n5c6ccccc6c6ccccc65)cc4c3c2)cc(-n2c3ccccc3c3ccccc32)c1]

The invention claimed is:

1. A metal-carbene complex of formula (I):

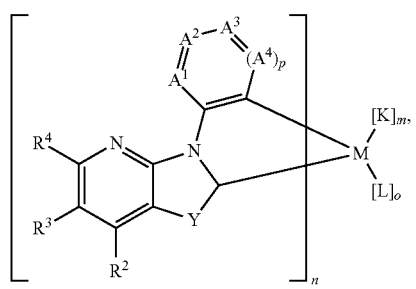

wherein:

M is Ir;

n is an integer selected from 1, 2 and 3, where the ligand(s):

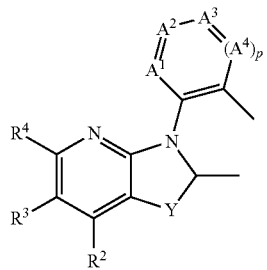

are each bidentate ligands;

Y is NR$^1$;

R$^1$ is ethyl, isopropyl, tert-butyl, neopentyl, CF$_3$, a substituted or unsubstituted cycloalkyl radical having 5 to 20 carbon atoms, or a substituted or unsubstituted aryl radical having 6 to 30 carbon atoms;

R$^2$, R$^3$, R$^4$ are each independently hydrogen, a linear or branched alkyl radical having 1 to 6 carbon atoms, substituted or unsubstituted aryl radical having 6 to 30 carbon atoms, substituted or unsubstituted heteroaryl radical having a total of 5 to 18 carbon atoms and/or heteroatoms, group with donor or acceptor action selected from halogen radicals; CF$_3$, CN and SiMe$_3$, or R$^2$ and R$^3$ or R$^3$ and R$^4$ form, together with the carbon atoms to which they are bonded, an optionally substituted unsaturated, saturated or aromatic ring which is optionally interrupted by at least one further heteroatom, has a total of 5 to 18 carbon atoms and/or heteroatoms and may optionally be fused to at least one further optionally substituted saturated or unsaturated or aromatic ring optionally interrupted by at least one further heteroatom and having a total of 5 to 18 carbon atoms and/or heteroatoms;

A$^1$ is CR$^6$;

A$^2$ is CR$^7$;

A$^3$ is CR$^8$;

A$^4$ is CR$^9$;

R$^6$, R$^7$, R$^8$, R$^9$ are each independently hydrogen, a linear or branched alkyl radical optionally bearing at least one functional group, optionally interrupted by at least one heteroatom and having 1 to 20 carbon atoms, substituted or unsubstituted aryl radical having 6 to 30 carbon atoms, substituted or unsubstituted heteroaryl radical having a total of 5 to 18 carbon atoms and/or heteroatoms, group with donor or acceptor action selected from halogen radicals, CF$_3$, CN and SiMe$_3$, or R$^6$ and R$^7$, R$^7$ and R$^8$, or R$^8$ and R$^9$ form, together with the carbon atoms to which they are bonded, a saturated, unsaturated or aromatic, optionally substituted ring which is optionally interrupted by at least one heteroatom, has a total of 5 to 18 carbon atoms and/or heteroatoms and may optionally be fused to at least one further optionally substituted saturated or unsaturated or aromatic ring optionally interrupted by at least one further heteroatom and having a total of 5 to 18 carbon atoms and/or heteroatoms;

p is 1;

K is an uncharged mono- or bidentate ligand;

L is a carbene ligand of formula (II):

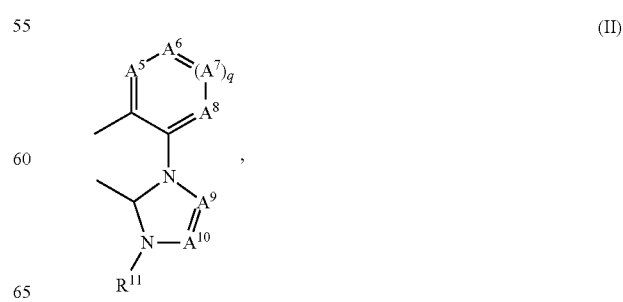

a ligand of the formula (B):

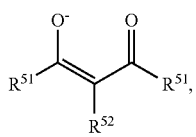

picolinato,
salicylato,
8-hydroxyquinolato, or
a heterocyclic noncarbene ligand of formula (III):

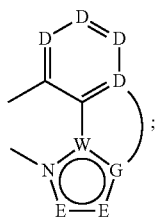

$A^9$ is $CR^{12}$ or N;
$A^{10}$ is $CR^{13}$ or N;
$R^{11}$ is a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted heterocycloalkyl radical optionally interrupted by at least one heteroatom, optionally bearing at least one functional group and having 3 to 20 carbon atoms and/or heteroatoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms;
$R^{12}$, $R^{13}$ are each independently hydrogen, a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted heterocycloalkyl radical optionally interrupted by at least one heteroatom, optionally bearing at least one functional group and having 3 to 20 carbon atoms and/or heteroatoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action;
$A^5$ is $CR^{14}$ or N;
$A^6$ is $CR^{15}$ or N;
$A^7$ is $CR^{16}$ or N;
$A^8$ is $CR^{17}$ or N;
$R^{14}$, $R^{15}$, $R^{16}$, $R^{17}$ are each independently hydrogen, a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted heterocycloalkyl radical optionally interrupted by at least one heteroatom, optionally bearing at least one functional group and having 3 to 20 carbon atoms and/or heteroatoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or
$R^{14}$ and $R^{15}$, $R^{15}$ and $R^{16}$ or $R^{16}$ and $R^{17}$ form, together with the carbon atoms to which they are bonded, an unsaturated or aromatic, optionally substituted ring optionally interrupted by at least one heteroatom and having a total of 5 to 18 carbon atoms and/or heteroatoms, and/or
$R^{12}$ and $R^{13}$ form, together with $A^9$ and $A^{10}$ to which they are bonded, an unsaturated or aromatic, optionally substituted ring optionally interrupted by exactly one heteroatom or two adjacent heteroatoms and having a total of 5 to 18 ring atoms, and/or
if $A^9$ is $CR^{12}$, $R^{12}$ and $R^{17}$ together form a saturated or unsaturated, linear or branched bridge optionally comprising heteroatoms, aromatic units, heteroaromatic units and/or functional groups and having a total of 1 to 30 carbon atoms and/or heteroatoms, to which is optionally fused a substituted or unsubstituted, five- to eight-membered ring comprising carbon atoms and/or heteroatoms;
q is 0 or 1;
$R^{51}$ is in each case independently a linear or branched alkyl radical having 1 to 6 carbons atoms, substituted or unsubstituted aryl radical having 6 to 20 carbon atoms; substituted or unsubstituted heteroaryl radical having a total of 5 to 18 carbon atoms and/or heteroatoms;
$R^{52}$ is hydrogen, a linear or branched alkyl radical having 1 to 6 carbon atoms, substituted or unsubstituted aryl radical having 6 to 20 carbon atoms;
D are each independently $CR^{18}$ or N;
W is C, N;
E are each independently $CR^{19}$, N, $NR^{20}$;
G is $CR^{21}$, N, $NR^{22}$, S, or O;
$R^{18}$, $R^{19}$, $R^{21}$ are each independently hydrogen, a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted heterocycloalkyl radical optionally interrupted by at least one heteroatom, optionally bearing at least one functional group and having 3 to 20 carbon atoms and/or heteroatoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or in each case 2 $R^{18}$, $R^{19}$ and $R^{21}$ radicals, together with the carbon atoms to which they are bonded, form a saturated, unsaturated or aromatic, optionally substituted ring optionally interrupted by at least one heteroatom and having a total of 5 to 18 carbon atoms and/or heteroatoms;

$R^{20}$, $R^{22}$ are each independently a linear or branched alkyl radical optionally interrupted by at least one heteroatom, optionally bearing at least one functional group and having 1 to 20 carbon atoms, substituted or unsubstituted cycloalkyl radical optionally interrupted by at least one heteroatom, optionally bearing at least one functional group and having 3 to 20 carbon atoms, substituted or unsubstituted heterocycloalkyl radical optionally interrupted by at least one heteroatom, optionally bearing at least one functional group and having 3 to 20 carbon atoms and/or heteroatoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action; preferably o,o'-dialkylated aryl radical;

where the solid curved line is an optional bridge between one of the D groups and the G group, and the bridge is defined as alkylene, arylene, heteroarylene, alkynylene, alkenylene, $NR^{23}$, O, S, $SiR^{24}R^{25}$, $CR^{50}$=N and $(CR^{26}R^{27})_d$, where one or more nonadjacent $(CR^{26}R^{27})$ groups may be replaced by $NR^{23}$, O, S, $SiR^{24}R^{25}$;

d is 2 to 10;

$R^{24}$, $R^{25}$, $R^{26}$, $R^{27}$, $R^{50}$ are each H, alkyl, aryl, heteroaryl, alkenyl, alkynyl;

m is 0, 1 or 2, where, when m is 2, the K ligands may be the same or different; and o is 0, 1 or 2, where, when o is 2, the L ligands may be the same or different, wherein the following compounds are excluded:

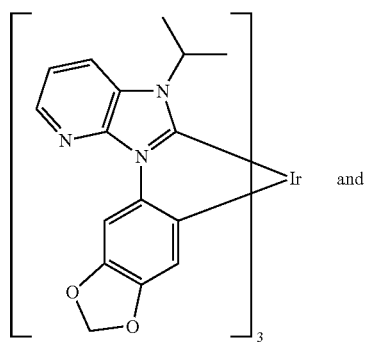

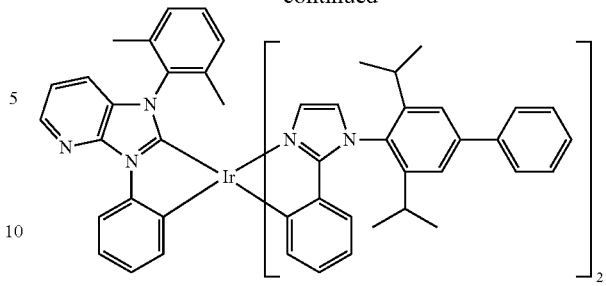

2. The metal-carbene complex according to claim 1, wherein:
n is 3, where the ligands

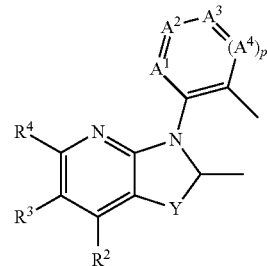

are each bidentate ligands, where all n ligands are the same; and m, o are each 0.

3. The metal-carbene complex according to claim 1, wherein:
n is 1, 2 or 3, where the ligand(s)

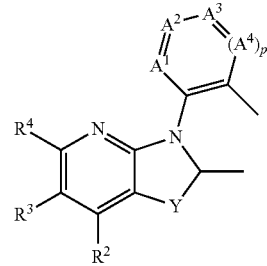

are each bidentate ligands;

$R^1$ is ethyl, isopropyl, tert-butyl, neopentyl, $CF_3$, a substituted or unsubstituted cycloalkyl radical having 5 to 20 carbon atoms, substituted or unsubstituted aryl radical having 6 to 30 carbon atoms;

$R^2$, $R^3$, $R^4$ are each independently hydrogen, a linear or branched alkyl radical having 1 to 6 carbon atoms, substituted or unsubstituted aryl radical having 6 to 30 carbon atoms, substituted or unsubstituted heteroaryl radical having a total of 5 to 18 carbon atoms and/or heteroatoms, group with donor or acceptor action selected from halogen radicals; $CF_3$, CN and $SiMe_3$; or $R^2$ and $R^3$ or $R^3$ and $R^4$ form, together with the carbon atoms to which they are bonded, an optionally substituted unsaturated, saturated or aromatic ring which is optionally interrupted by at least one further heteroatom, has a total of 5 to 18 carbon atoms and/or heteroatoms and may optionally be fused to at least one further optionally substituted saturated or unsaturated or aromatic ring optionally interrupted by at least one further heteroatom and having a total of 5 to 18 carbon atoms and/or heteroatoms;

R$^6$, R$^7$, R$^8$, R$^9$ are each independently hydrogen, a linear or branched alkyl radical optionally bearing at least one functional group, optionally interrupted by at least one heteroatom and having 1 to 20 carbon atoms, substituted or unsubstituted aryl radical having 6 to 30 carbon atoms, substituted or unsubstituted heteroaryl radical having a total of 5 to 18 carbon atoms and/or heteroatoms, group with donor or acceptor action selected from halogen radicals, CF$_3$, CN and SiMe$_3$, or R$^6$ and R$^7$, R$^7$ and R$^8$, or R$^8$ and R$^9$ form, together with the carbon atoms to which they are bonded, a saturated, unsaturated or aromatic, optionally substituted ring which is optionally interrupted by at least one heteroatom, has a total of 5 to 18 carbon atoms and/or heteroatoms and may optionally be fused to at least one further optionally substituted saturated or unsaturated or aromatic ring optionally interrupted by at least one further heteroatom and having a total of 5 to 18 carbon atoms and/or heteroatoms;

m is 0; and o is 0, 1 or 2.

4. The metal-carbene complex according to claim 1, wherein:

n is 3, where the ligand(s)

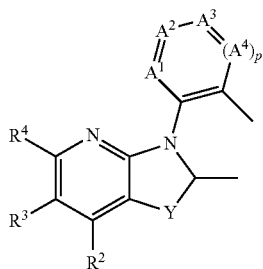

are each bidentate ligands.

5. A process for preparing the metal-carbene complex of claim 1, the process comprising contacting at least one compound comprising the metal M with compounds of the general formula (IV) or (V):

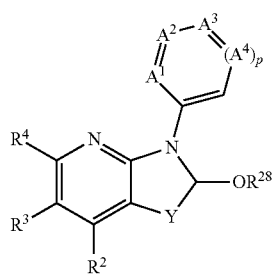

(IV)

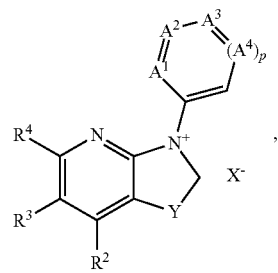

(V)

to form the metal-carbene complex,
wherein:
R$^{28}$ is independently SiR$^{29}$R$^{30}$R$^{31}$, aryl, heteroaryl, alkyl, cycloalkyl or heterocycloalkyl;
X is F, Cl, Br, I, PF$_6$, BF$_4$; and
R$^{29}$, R$^{30}$, R$^{31}$ are each independently aryl, heteroaryl, alkyl, cycloalkyl or heterocycloalkyl.

6. An organic electronic component comprising at least one metal-carbene complex according to claim 1.

7. The organic electronic component according to claim 6, wherein the organic electronic component is selected from organic light-emitting diodes (OLEDs), organic photovoltaic cells (OPVs), organic field-effect transistors (OFETs) and light-emitting electrochemical cells (LEECs).

8. The organic electronic component according to claim 7, wherein the organic electronic component is an OLED comprising a light-emitting layer comprising the metal-carbene complex.

9. The organic electronic component according to claim 7, wherein the organic electronic component is an OLED comprising the metal-carbene complex and at least one compound of the formula (X):

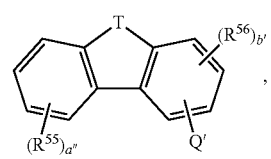

(X)

wherein:
T is NR$^{57}$, S, O or PR$^{57}$;
R$^{57}$ is aryl, heteroaryl, alkyl, cycloalkyl or heterocycloalkyl;
Q' is —NR$^{58}$R$^{59}$, —SiR$^{70}$R$^{71}$R$^{72}$, —P(O)R$^{60}$R$^{61}$, —PR$^{62}$R$^{63}$, —S(O)$_2$R$^{64}$, —S(O)R$^{65}$, —SR$^{66}$ or —OR$^{67}$;
R$^{55}$, R$^{56}$ are each independently alkyl, cycloalkyl, heterocycloalkyl, aryl, heteroaryl, SiR$^{70}$R$^{71}$R$^{72}$, a Q' group or a group with donor or acceptor action;
a" is 0, 1, 2, 3 or 4;
b' is 0, 1, 2 or 3;
R$^{58}$,R$^{59}$ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action, and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl and a group with donor or acceptor action; and $R^{70}$, $R^{71}$, $R^{72}$, $R^{60}$, $R^{61}$, $R^{62}$, $R^{63}$, $R^{64}$, $R^{65}$, $R^{66}$, $R^{67}$ are each independently aryl, heteroaryl, alkyl, cycloalkyl or heterocycloalkyl, or two units of the general formula (X) are optionally bridged to one another via a linear or branched, saturated or unsaturated bridge optionally interrupted by at least one heteroatom, via a bond or via O.

10. The organic electronic component according to claim 9, comprising at least one compound of the formula (XI) or (XI*):

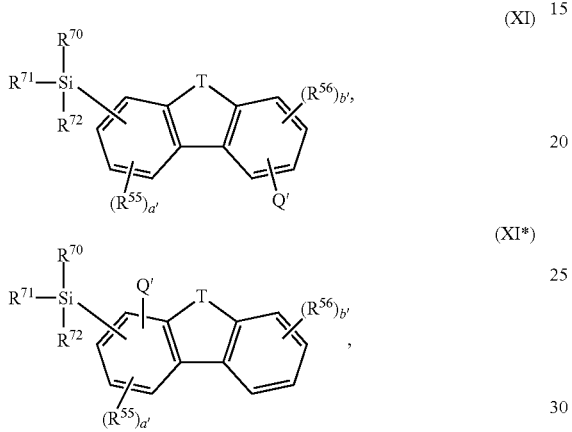

wherein:

T is $NR^{57}$, S, O or $PR^{57}$;

$R^{57}$ is aryl, heteroaryl, alkyl, cycloalkyl or heterocycloalkyl;

Q is $-NR^{58}R^{59}$, $-SiR^{70}R^{71}R^{72}$, $-P(O)R^{60}R^{61}$, $-PR^{62}R^{63}$, $-S(O)_2R^{64}$, $-S(O)R^{65}$, $-SR^{66}$ or $-R^{67}$;

$R^{70}$, $R^{71}$, $R^{72}$ are each independently aryl, heteroaryl, alkyl, cycloalkyl, heterocycloalkyl or $OR^{73}$;

$R^{55}$, $R^{56}$ are each independently alkyl, cycloalkyl, heterocycloalkyl, aryl, heteroaryl, a Q group or a group with donor or acceptor action;

a', b' for the compound of the formula (XI): are each independently 0, 1, 2, 3; for the compound of the formula (XI*), a' is 0, 1, 2 and b' is 0, 1, 2, 3, 4;

$R^{58}$, $R^{59}$ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl and a group with donor or acceptor action;

$R^{73}$ are each independently $SiR^{74}R^{75}R^{76}$, aryl, heteroaryl, alkyl, cycloalkyl or heterocycloalkyl, optionally substituted by an $OR^{77}$ group;

$R^{77}$ are each independently $SiR^{74}R^{75}R^{76}$, aryl, heteroaryl, alkyl, cycloalkyl or heterocycloalkyl; and $R^{60}$, $R^{61}$, $R^{62}$, $R^{63}$, $R^{64}$, $R^{65}$, $R^{66}$, $R^{67}$, $R^{74}$, $R^{75}$, $R^{76}$ are each independently aryl, heteroaryl, alkyl, cycloalkyl or heterocycloalkyl, or two units of the general formulae (XI) and/or (XI*) are optionally bridged to one another via a linear or branched, saturated or unsaturated bridge optionally interrupted by at least one heteroatom or via O, where this bridge in the general formulae (XI) and/or (XI*) is in each case attached to the silicon atoms in place of $R^{71}$.

11. The organic electronic component according to claim 10, wherein the organic electronic component is an OLED comprising an emission layer comprising the metal-carbene complex and at least one matrix material of the formula (X) and/or (XI) or (XI*).

12. The organic electronic component according to claim 8, wherein the organic electronic component is an OLED comprising an emission layer consisting of the metal-carbene complex.

13. A device selected from the group consisting of a stationary visual display unit, a mobile visual display unit, and an illuminator, comprising at least one OLED according to claim 7.

14. An OLED, comprising the metal-carbene complex according to claim 1.

15. The OLED according to claim 14, wherein the metal-carbene complex is adapted to function as an emitter, matrix material, charge transport material, charge blocker, or a combination thereof.

16. An OLED, comprising the metal-carbene complex according to claim 1, wherein the metal-carbene complex is adapted to function as a hole transport material, a charge blocker, or both.

* * * * *